US011913009B2

(12) United States Patent
Messier

(10) Patent No.: US 11,913,009 B2
(45) Date of Patent: Feb. 27, 2024

(54) IDENTIFICATION OF RESISTANCE GENES FROM WILD RELATIVES OF BANANA AND THEIR USES IN CONTROLLING PANAMA DISEASE

(71) Applicant: EG Crop Science, Inc., Longmont, CO (US)

(72) Inventor: Walter Messier, Longmont, CO (US)

(73) Assignee: EG Crop Science, Inc., Longmont, CO (US)

( * ) Notice: Subject to any disclaimer, the term of this patent is extended or adjusted under 35 U.S.C. 154(b) by 0 days.

(21) Appl. No.: 17/733,561

(22) Filed: Apr. 29, 2022

(65) Prior Publication Data

US 2022/0267790 A1 Aug. 25, 2022

Related U.S. Application Data

(62) Division of application No. 16/896,682, filed on Jun. 9, 2020, now abandoned.

(60) Provisional application No. 62/912,010, filed on Oct. 7, 2019, provisional application No. 62/866,872, filed on Jun. 26, 2019.

(51) Int. Cl.
*C12N 15/82* (2006.01)
*C07K 14/415* (2006.01)

(52) U.S. Cl.
CPC ........ *C12N 15/8282* (2013.01); *C07K 14/415* (2013.01)

(58) Field of Classification Search
None
See application file for complete search history.

(56) References Cited

U.S. PATENT DOCUMENTS

| 6,133,035 A | 10/2000 | Engler et al. |
| 7,381,556 B2 | 6/2008 | Alibhai et al. |
| 7,534,930 B2 | 5/2009 | Vishnevetsky et al. |
| 2005/0153399 A1* | 7/2005 | De Nobel .............. C12N 15/80 435/484 |
| 2018/0355363 A1 | 12/2018 | Schmuelling et al. |
| 2021/0332379 A9* | 10/2021 | Messier ............. C12N 15/8213 |

FOREIGN PATENT DOCUMENTS

| WO | 2018220581 A1 | 12/2018 |
| WO | 2020263561 A1 | 12/2020 |

OTHER PUBLICATIONS

Van Den Berg et al (Tolerance in banana to Fusarium wilt is associated with early up-regulation of cell wall-strengthening genes in the roots. Molecular Plant Pathology, 333-341, 2007) (Year: 2007).*

D'Hont et al (The banana (*Musa acuminata*) genome and the evolution of monocotyledonous plants. Nature. 488:213-217, 2012) (Year: 2012).*
Qu et al (Molecular Cloning and Functional Analysis of a Novel Type of Bowman-Birk Inhibitor Gene Family in Rice. Plant Physiology, vol. 133, pp. 560-570, 2003) (Year: 2003).*
May et al (Generation of Transgenic Banana (*Musa acuminata*) Plants via Agrobacterium-Mediated Transformation. Nature Biotechnology 13:486-492, 1995) (Year: 1995).*
Pekkarinen et al (Kinetics of the Inhibition of Fusarium Serine Proteinases by Barley (*Hordeum vulgare* L.) Inhibitors. J. Agric. Food Chem. 2007, 55, 2736-2742, 2007). (Year: 2007).*
Accesswire, Press Release, "Evolutionary Genomics Announces Partnership with Dole Food Company to Save Cavendish Bananas," 2 pages (Aug. 19, 2020).
Bai et al., "Transcriptome and Expression Profile Analysis of Highly Resistant and Susceptible Banana Roots Challenged with *Fusarium oxysporum* f. sp. *cubense* Tropical Race 4," PLOS One, Published Sep. 23, 2013, vol. 8; Issue 9; e73945, 11 pages.
Becker et al., "Genetic transformation of Cavendish banana (*Musa* spp. AAA group) cv.'Grand Nain' via microprojectile bombardment," Plant Cell Reports, 2000, 19, pp. 229-234.
Chen et al., "Assessing Variations in Host Resistance to *Fusarium oxysporum* f sp. *cubense* Race 4 in *Musa* Species, With a Focus on the Subtropical Race 4," Frontiers in Microbiology, vol. 10, Article 1062, 13 pages (May 15, 2019).
Chong-Perez, B. et al., "Excision of a selectable marker gene in transgenic banana using a Cre/lox system controlled by an embryo specific promoter," Plant Molecular Biology, vol. 83, pp. 143-152 (Apr. 17, 2013).
Chong-Perez, B. et al., "Heat shock induced excision of selectable marker genes in transgenic banana by the Cre-lox site-specific recombination system," Journal of Biotechnology, vol. 159, Iss. 4, pp. 265-273 (Jun. 30, 2012).
Cote et al., "Embryogenic cell suspensions from the male flower of *Musa* AAA cv. Grand Nain," Physiologia Plantarum, 97, 1996, pp. 285-290.
Dale et al., "Transgenic Cavendish bananas with resistance to Fusarium wilt tropical race 4," XP093063451, Nature Communications, vol. 8, No. 1, 8 pages (Nov. 14, 2017).
Database EMBL [Online] X, "Musa acuminata clone 2-35 trypsin inhibitor mRNA, complete cds.", XP002809734, retrieved from EBI accession No. EM_STD:DQ531617, Database accession No. DQ531617 (Jun. 26, 2006).

(Continued)

*Primary Examiner* — Charles Logsdon
*Assistant Examiner* — Wayne Zhong
(74) *Attorney, Agent, or Firm* — Weatherly IP Solutions, LLC; James M. Weatherly

(57) ABSTRACT

The present disclosure provides compositions and methods for providing broad-based resistance to fungal pathogens, such as a *Fusarium* fungi, and plants derived therefrom.

22 Claims, 9 Drawing Sheets
Specification includes a Sequence Listing.

(56) References Cited

OTHER PUBLICATIONS

De Jesus Rocha et al., "Improvements in the Resistance of the Banana Species to Fusarium Wilt: A Systematic Review of Methods and Perspectives," Journal of Fungi, vol. 7, Article 249, 35 pages Mar. 25, 2021).
Dhed'A et al., "Plant regeneration in cell suspension cultures of the cooking banana cv. Bluggoe (*Musa* spp, ABB group)," Fruits, 1991, vol. 46, No. 2, p. 125~135.
Dugdale et al., Promoter activity associated with the Intergenic regions of banana bunchy top virus DNA-1 to -6 in transgenic tobacco and banana cells, Journal of General Virology, vol. 79, Issue 10, pp. 2301-2311, (Oct. 1, 1998).
Escalant and Jain, Chapter 30, "Banana improvement with cellular and molecular biology, and induced mutations: future and perspectives," 8 pages, In Jain and Swennan, editors, Banana Improvement: Cellular, Molecular Biology, and Induced Mutations, 2004, Food and Agriculture Organization of the United Nations, Science Publishers, Inc.
Escalant et al., "Amplified somatic embryogenesis from male flowers of triploid banana and plantain cultivars (*Musa* spp.)," In Vitro Cellular & Developmental Biology—Plant, Oct. 1994, 30(4), 181-186.
Extended European Search Report for EP Patent Application No. 20832496.2 dated Jul. 26, 2023, 8 pages.
Garcia-Bastidas, F. et al., "An Improved Phenotyping Protocol for Panama Disease in Banana," Front. Plant. Sci., vol. 10, Article 1006 (Aug. 6, 2019).
Garcia-Bastidas, F., "*Fusarium oxysporum* f.sp. *cubense* Tropical race 4 (Foc TR4)," CABI, 17 pages (Jun. 6, 2022).
Garcia-Bastidas, Fernando A., et al., "Induced resistance to Fusarium wilt of banana caused by Tropical Race 4 in Cavendish cv Grand Naine bananas after challenging with avirulent *Fusarium* spp.," Plos One, 19 pages (Sep. 21, 2022).
GenBank accession NC_025206.1, "*Musa acuminata* subsp. malaccensis chromosome 6, ASM31385v2, whole genome shotgun sequence," Oct. 25, 2016, 2 pages.
GenBank: DQ531617.1 "Musa acuminata Clone 2-35 Trypsin Inhibitor mRNA, Complete Cds," Jun. 26, 2006 [online] [Retrieved on Sep. 4, 2020], Retrieved from the internet URL: https://www.nobl.nlm.nih.gov/nuccore/DQ531617.1.
Genpept: "Predicted: Bowman-Birk Type Proteinase Inhibitor-Like Isoform X2 [*Musa acuminata* Subsp. *malaccensis*]," Oct. 2016, Retrieved from the Internet: URL: https://www.ncbi.nim.nih.gov/protein/XP_009400399.1.
Gentzbittel, et al., "Cloning of molecular markers for disease resistance in sunflower, *Helianthus annuus* L," Theor Appl Genet, vol. 96, pp. 519-525 (1998).
Gitlin-Domagalska, Agata, et al., "Bowman-Birk Inhibitors: Insights into Family of Multifunctional Proteins and Peptides with Potential Therapeutical Applications," Pharmaceuticals, vol. 13, No. 421 (2020).
Grapin et al., "Somatic embryogenesis in plantain banana," in Vitro Cell Dev. Biol. Plant., 1996, 32: pp. 66-71.
Hellinger and Gruber, "Peptide-based protease inhibitors from plants," Drug Discov Today, vol. 24, Issue 9, pp. 1877-1889; (Jun. 3, 2019).
Heslop-Harrison et al., "Domestication, Genomics and the Future for Banana," Annals of Botany, vol. 100, Issue 5, pp. 1073-1084 (Oct. 2007).
Heslop-Harrison, J.S., Genomics, Banana Breeding and Superdomestication, Proceedings International ISHS-ProMusa Symposium on Global Perspectives on Asian Challenges, Acta Hort., vol. 897, pp. 55-62 (2011).
Hu, C-H et al., "An efficient protocol for the production of chit42 transgenic Furenzhi banana (*Musa* spp. AA group) resistant to Fusarium oxysporum," In Vitro Cellular & Developmental Biology Plant, vol. 49, pp. 584-592 (2013).

International Search Report and Written Opinion for International Application No. PCTUS2020036828 dated Nov. 4, 2020, 13 pages.
Jones, David R. et al., ed. Handbook of Diseases of Banana, Abaca, and Enset, Boston MA: CABI, 2018, pp. 80-82.
Khanna, H. et al., "Centrifugation Assisted Agrobacterium tumefaciens-mediated Transformation (CAAT) of embryogenic cell suspensions of banana (*Musa* spp. *cavendish* AAA and Lady finger AAB)," Molecular Breeding, vol. 14, pp. 239-252 (Oct. 2004).
Li et al., "Transcriptome profiling of resistant and susceptible Cavendish banana roots following inoculation with *Fusarium oxysporum* f. sp. *cubense* tropical race 4," BMC Genomics, vol. 13, Issue 374, 11 pages (2012).
Li, W.M. et al., "Resistance sources to *Fusarium oxysporum* f. sp. *cubense* tropical race 4 in banana wild relatives," XP093063408, Plant Pathology, vol. 64, No. 5, pp. 1061-1067 (Feb. 17, 2015).
Liu, J. et al., "Efficient regeneration and genetic transformation platform applicable to five Musa varieties," Electronic Journal of Biotechnology, vol. 25, pp. 33-38 (2017).
Marroquin et al., "Somatic Embryogenesis and Plant Regeneration through Cell Suspensions in Musa acuminata," In Vivo Cell. Div. Biol., 1993, 29P, pp. 43-46.
Martinez et al., "The Advance of Fusarium Wilt Tropical Race 4 In Musaceae of Latin America and the Caribbean: Current Situation," Pathogens, vol. 12, Article 277, 24 pages (Feb. 8, 2023).
Mintoff et al., "Banana Cultivar Field Screening for Resisance to *Fusarium oxysporum* f.sp. *cubense* Tropical Race 4 in the Northern Territory," Journal of Fungi, vol. 7, No. 8, Article 627, 16 pages (Aug. 1, 2021).
NCBI (XM_009402124, published Oct. 25, 2016).
Niu et al., "Comparative digital gene expression analysis of tissue-cultured plantlets of highly resistant and susceptible banana cultivars in response to Fusarium oxysporum," Int. Journal of Molecular Sciences, vol. 19, Article 350, 8 pages (2018).
Non-Final Office Action for U.S. Appl. No. 16/896,682 dated Nov. 1, 2021, 32 pages.
Ntui et al., "Robust CRISPR/Cas9 mediated genome editing tool for banana and plantain (*Musa* spp.)," Current Plant Biology, Jan. 2020, vol. 21, 10 pages.
Paul et al., "Apoptosis-related genes confer resistance to Fusarium wilt in transgenic 'Lady Finger' bananas," Plant Biotechnology Journal, 2011, vol. 9, pp. 1141-1148.
Peraza-Echeverria et al.. "Molecular cloning and in silico analysis of potential Fusarium resistance genes in banana," Mol. Breeding, 2009, vol. 23, Issue No. 3, pp. 431-443.
Ploetz, "Fusarium Wilt of Banana Is Caused by Several Pathogens Referred to as *Fusarium oxysporum* f. sp. *cubense*," Phytopathology, vol. 96, No. 6, pp. 653-656 (Jun. 2006).
Ploetz, "Fusarium Wilt of banana," Phytopathology, vol. 105, pp. 1512-1621 (Jun. 1, 2015).
Ploetz, "Management of Fusarium wilt of banana: A review with special ference to tropical race 4," Crop Protection, 2015, vol. 73, pp. 7-15, 9 pages.
Remy et al., "Genetically modified bananas: Past, present and future," Proceedings 2nd Genetically Modified Organisms in Horticulture Symposium, ISHS Acta Horticulturae 974, pp. 71-80 (2013).
Ribeiro et al., "Sources of resistance to *Fusarium oxysporum* f. sp. *cubense* in banana germplasm," Rev. Bras. Frutic., Jaboticabal, vol. 40, No. 1, 8 pages (2018).
Sagi et al., "Genetic transformation of banana and plantain (*Musa* spp.) via particle bombardment," Nature Bio Technology, vol. 13, Issue 5, pp. 481-485 (May 1, 1996).
Sagi et al., "Transient gene expression in electroporated banana (*musa* spp., cv. "Bluggoe", ABB group) protoplasts isolated from regenerable embryogenetic cell suspensions," Plant Cell Reports, vol. 13, pp. 262-266 (1994).
Mohandas, S. et al., "Banana: Genomics and Transgenic Approaches for Genetic Improvement," Springer Nature, Book (2016).
Ssali et al., "Inheritance of resistance to *Fusarium oxysporum* f. sp. *cubense* race 1 in bananas," Euphytica, Jul. 9, 2013, 194: 425, 6 pages.

(56) References Cited

OTHER PUBLICATIONS

Tripathi et al., "CRISPR/Cas9 editing of endogenous banana streak virus in the B genome of *Musa* spp. overcomes a major challenge in banana breeding," Communications Biology, vol. 2, Article No. 46, 11 pages (Jan. 31, 2019).
United Nations, UN News, Global perspective Human stories, "FAO plants new efforts to protect bananas under disease threat," 7 pages (Oct. 3, 2019).
Vishnevetsky et al., "Improved tolerance toward fungal diseases in transgenic Cavendish banana (*Musa* spp. AAA group) cv. Grand Nain," Transgenic Res., 2011, 20(1), pp. 61-72.
Wang et al., "Differential gene expression in banana roots in response to Fusarium wilt," Canadian Journal of Plant Pathology, Jun. 20, 2017, 39(2), pp. 163-175.
Wu et al., "Whole genome sequencing of a banana wild relative *Musa* Itinerans provides insights into lineage-specific diversification of the *Musa* genus," Scientific Reports, vol. 6: Article No. 31586, 11 pages (Aug. 17, 2016).
Zhang et al., "Identification and evaluation of resistance to *Fusarium oxysporum* f. sp. *cubense* tropical race 4 in Musa acuminata Pahang," Euphytica, vol. 214: 106, 12 pages (2018).
Zhong et al., "The Competence of Maize Shoot Meristems for Integrative Transformation and Inherited Expression of Transgenes," Plant Physiol., vol. 110, Issue 4, pp. 1097-1107 (Apr. 1996).
Zhou et al., "Disentangling the resistant mechanism of Fusarium wilt TR4 interactions with different cultivars and its elicitor application," Frontiers in Plant Science, vol. 14, 16 pages (Mar. 2, 2023).
Zuo et al., "Germplasm screening of *Musa* spp. for resistance to *Fusarium oxysporum* f. sp. *cubense* tropical race 4 (Foc-TR4)," Eur J Plant Pathol, 2018, 151, pp. 723-734.

\* cited by examiner

FIG. 1

M. itinerans allele 1 (SEQ ID NO 2)                atggctggaggaggcaaaagaggtgaagcgtcgtctcttctacttgtgac
M. acuminata resistant allele 1 (SEQ ID NO 9)      atggctggaggaggcaaaagaggtgaagcgtcgtctcttctacttgtgac
M. acuminata sensitive allele (SEQ ID NO 14)       atggctggaggaggcaaaagaggtgaagcgtcgtctcttctacttgtgac
M. balbisiana Acc. ITC1016 (SEQ ID NO 27)          atggctggaggaggcaaaagagggtgaagcgtcgtctcttctacttgtgac
M. basjoo allele 1 (SEQ ID NO 18)                  atggctggaggaggcaaaagaggtgaagcgtcgtctcttctacttgtgac M. itinerans allele 1 (SEQ ID NO 2)                gctgctcgtgatgttgttggccttcttcgccaccgactcctcggcgGCCC
M. acuminata resistant allele 1 (SEQ ID NO 9)      gctgctcgtgacgttgttggccttcttcgccaccaactcctcggcaGCCC
M. acuminata sensitive allele (SEQ ID NO 14)       gctgctcgtgacgttgttggccttcttcgccaccaactcctcggcaGCCC
M. balbisiana Acc. ITC1016 (SEQ ID NO 27)          gctgctcgtgacgttgttggccttcttcgccaccgactcctcggcaGCCC
M. basjoo allele 1 (SEQ ID NO 18)                  gctgctcgtgacgttgttggccttcttcgccaccaactcctcagcaGCCC
                                                                                            *

M. itinerans allele 1 (SEQ ID NO 2)                GTGTCACACCCGTCCGCACTCCCTCGCACTGAGAGCGGTACTGAGTGCGTTG
M. acuminata resistant allele 1 (SEQ ID NO 9)      GTGTCACACCCGTCCGCAATCCCTCGCACTGAGAGCGGCACTGAGTGCGGTG
M. acuminata sensitive allele (SEQ ID NO 14)       GTGTCACACCCGTCCGCAATCCCTCGCACTGAGAGCGGCACTGAGTGCGGTG
M. balbisiana Acc. ITC1016 (SEQ ID NO 27)          GTGTCGCACCCGTCCGCACTCCCTCGCACTGAGAGCGGCACTGAGTGCGTTG
M. basjoo allele 1 (SEQ ID NO 18)                  GTGTCACACCCGTCCGCAATCCCTCGCACTGAGAGCGGCACTGAGTGCGGTG
                                                             *

M. itinerans allele 1 (SEQ ID NO 2)                GAGGCAAGGGCAGATGGGCCGTGTTGCAGATGCATCTGTCCTCTCATTTA
M. acuminata resistant allele 1 (SEQ ID NO 9)      GGGGCAAGGCAAGATGAGCCGTGCTGCAGATGCGCGTGTCCTCTCATTTA
M. acuminata sensitive allele (SEQ ID NO 14)       GGGGCAAGGCAAGATGAGCCGTGCTGCAGATGCGCGTGTCCTCTCATTTA
M. balbisiana Acc. ITC1016 (SEQ ID NO 27)          GGGGTAAGGCAAGATGCGCCGTGCTGCACATGCGTGTGTCCTCTCATTTA
M. basjoo allele 1 (SEQ ID NO 18)                  GGGGCAAGGCAAGATGAGCCGTGCTGCAGATGCGCGTGTCCTCTCATTTA
                                                   *    *   **   *           *     *    ***

FIG. 1 Continued

```
M. itinerans allele 1 (SEQ ID NO 2)              CCCACCTACTTGGTGCGTTTGCAGCGGCGTATGGCAAGGCTCCTGCCCTT
M. acuminata resistant allele 1 (SEQ ID   NO 9)  CCCACCTACTTGGTGCATTTGCGGCGGCATATGGCAAGGCTCCTGCCCTT
M. acuminata sensitive allele (SEQ ID NO 14)     CCCACCTACTTGGTGCATTTGCGGCGGCATATGGCAAGGCTCCTGCCCTT
M. balbisiana Acc. ITC1016 (SEQ ID NO 27)        CCCACCTCCTTTTTGCTTTTGCGGCGGCGTATGGCAAGGCTCCTGCCCGT
M. basjoo allele 1 (SEQ ID NO 18)                CCCACCTACTTGGTGCATTTGCGGCGGCATATGGCAAGGCTCCTGCCCTT
                                                        *   **   *     *     *                   .

M. itinerans allele 1 (SEQ ID NO 2)              CCGCCTGCACCAACTGCGAGTGTCTCCTCAACGAGTGCACTTGCCTCGAT
M. acuminata resistant allele 1 (SEQ ID   NO 9)  CCGCCTGCAACAACTGCCAGTGTGTCCTCAACGAGTGCACTTGCCTCGAT
M. acuminata sensitive allele (SEQ ID NO 14)     CCGCCTGCAACAACTGCCAGTGTGTCCTCAACGAGTGCACTTGCCTCGAT
M. balbisiana Acc. ITC1016 (SEQ ID NO 27)        CCGCCTGCACCAACTGCGAGTGTGTCCTCAACGAGTGCACTTGCATCGAT
M. basjoo allele 1 (SEQ ID NO 18)                CCGCCTGCAACAACTGCCAGTGTGTCCTCAACGAGTGCACTTGCCTCGAT
                                                          *       *     *                    *

M. itinerans allele 1 (SEQ ID NO 2)              CACGTGGACTACAAGGCCTGCCAGGCCGACTCCTGTGGCTGGCTTGATGG
M. acuminata resistant allele 1 (SEQ ID   NO 9)  CTTATGGACCCCAAGGTCTGCGAGGCCAACTCCTGTCCCTGGCCTGTTGC
M. acuminata sensitive allele (SEQ ID NO 14)     CTTATGGACCCCAAGGTCTGCGTGGCCAACTCCTGTCCCTGGCGTGATGC
M. balbisiana Acc. ITC1016 (SEQ ID NO 27)        CGTGTGGACCCCAAGGCCTGCGAGGCCGACTCCTGTGCC-GGCTCGATGC
M. basjoo allele 1 (SEQ ID NO 18)                CTTATGGACCCCAAGGTCTGCGAGGCCAACTCCTGTCCCTGGCCTGTTGC
                                                  *•*      **      *    **    *        ** *   *. *  *

M. itinerans allele 1 (SEQ ID NO 2)              CGTCCCCAAACTAGAGCCGTCGCAGCAGTGGGCGATCGAAGAAACCGGTG
M. acuminata resistant allele 1 (SEQ ID   NO 9)  AGCCCCCAAAGTAGAGCCGGCGCAGCAGTGGGCTATCGAAGAAACCGGTG
M. acuminata sensitive allele (SEQ ID NO 14)     AGCCCCCAAAGTAGAGCCGGCGCAGCAGTGGGCGATCGAAGAAACCGGTG
M. balbisiana Acc. ITC1016 (SEQ ID NO 27)        AGCCCCCAAAGtag
M. basjoo allele 1 (SEQ ID NO 18)                AGCCCCCAAAGTAGAGCCGGCGCAGCAGTGGGCTATCGAAGAAACCGGTG
                                                 . *       *        *             .
```

FIG. 1 Continued

M. itinerans allele 1 (SEQ ID NO 2)                    GGAAATTAGCGATGATGATGGTGTGA M. acuminata resistant allele 1 (SEQ ID NO 9)          GGAAATTAGCGATGATGATGGTGTGA M. acuminata sensitive allele (SEQ ID NO 14)           GGAAATTAGCGATGATGATGGTGTGA M. balbisiana Acc. ITC1016 (SEQ ID NO 27)

M. basjoo allele 1 (SEQ ID NO 18)                      GGAAATTAGCGATGATGATGGTGTGA

FIG. 2

```
M. itinerans 1          (SEQ ID NO: 3)   magggkrgeasslllvtllvtllvmllaffatdssaARVTPRPH
M. itinerans 2          (SEQ ID NO: 6)   magggkrgeasslllvtllvtllvmllaffatdssaARVTPRPH
M. acuminata resistant  (SEQ ID NO: 12)  magggkrgeasslllvtllvtllaffatnssaARVTPRPQ
M. basjoo               (SEQ ID NO: 19)  magggkrgeasslllvtllvtllaffatnssaARVTPRPQ
M. acuminata sensitive  (SEQ ID NO: 15)  magggkrgeasslllvtllvtllaffatnssaARVTPRPQ
M. balbisiana           (SEQ ID NO: 32)  magggkrgeasslllvtllvtllaffatdssaARVAPRPH
Musella lasiocarpa      (SEQ ID NO: 25)  magggkrgeasslllvtllvtllaffatdssaARVTPRPQ M. itinerans 1          (SEQ ID NO: 3)   SLARAVLSALEARADGPCCRCICPLIYPPTWCVCSGVW
M. itinerans 2          (SEQ ID NO: 6)   SLARAVLSALEGRADGPCCRCICPLIYPPTWCICSGVW
M. acuminata resistant  (SEQ ID NO: 12)  SLARAALSAVGARQDEPCCRCACPLIYPPTWCICGGIW
M. basjoo               (SEQ ID NO: 19)  SLARAALSAVGARQDEPCCRCACPLIYPPTWCICGGIW
M. acuminata sensitive  (SEQ ID NO: 15)  SLARAALSALGARQDEPCCRCACPLIYPPTWCICGGIW
M. balbisiana           (SEQ ID NO: 32)  SLARAALSALGVRQDAPCCTCVCPLIYPPPFCFCGGVW
Musella lasiocarpa      (SEQ ID NO: 25)  SLARVALSALGVRQDEPCCRCICPRIYPTAWCICSGAW
                                                                         *

M. itinerans 1          (SEQ ID NO: 3)   SCFSACTNCECLMECTCIDHVDYKACQADSCGWLDG-VP
M. itinerans 2          (SEQ ID NO: 6)   SCFSACTNCECLMECTCIDHVDYKACEADSCGWLDG-VP
M. acuminata resistant  (SEQ ID NO: 12)  SCFSACTNCCCLMECTCIDLMDPKVCANSCPWPVA-AP
M. basjoo               (SEQ ID NO: 19)  SCFSACTNCCCLMECTCIDLMDPKVCEANSCPWPVA-AP
M. acuminata sensitive  (SEQ ID NO: 15)  SCFSACTNCCCLMECTCIDLMDPKVCANSCPWPVA-AP
M. balbisiana           (SEQ ID NO: 32)  SCFSACTNCEVMNECTCIDRVDPKACEADSCAGSMQ-PP
Musella lasiocarpa      (SEQ ID NO: 25)  SCFSACTTCKCLMECTCDDIVDYNACLADSCPWLDAAAP
                                                        *

M. itinerans 1          (SEQ ID NO: 3)   KLEPSQQWAIEETGGKLAMMV
M. itinerans 2          (SEQ ID NO: 6)   KLEPSQQWAIEETGGKLAAMV
M. acuminata resistant  (SEQ ID NO: 12)  KVEPAQQWAIEETGGKLAMMV
M. basjoo               (SEQ ID NO: 19)  KVEPAQQWAIEETGGKLAMMV
M. acuminata sensitive  (SEQ ID NO: 15)  KVEPAQQWAIEETGGKLAMMV
M. balbisiana           (SEQ ID NO: 32)  K
Musella lasiocarpa      (SEQ ID NO: 25)  KVEPSQQWAIEETGGKLATMV
```

FIG. 5

| | | |
|---|---|---|
| M. balbisiana Acc. ITC1016 (SEQ ID NO 26) | atgGCTGGAGGAGGCAAAAGGGTGAAGCGTCGTCTCTTACTTGTGAC |
| M. balbisiana Acc. ITC0545 (SEQ ID NO 28) | atgGCTGGAGGAGGCAAAAGGGTGAAGCGTCGTCTCTTACTTGTGAC |
| M. balbisiana Acc. ITC0080 (SEQ ID NO 29) | atgGCTGGAGGAGGCAAAAGGGTGAAGCGTCGTCTCTTACTTGTGAC |
| M. balbisiana Acc. ITC1527 (SEQ ID NO 30) | atgGCTGGAGGAGGCAAAAGGGTGAAGCGTCGTCTCTTACTTGTGAC |
| M. balbisiana Acc. ITC1016 (SEQ ID NO 26) | GCTGCTCGTGACGTTGTTGGCCTTCTTCGCCACCGACTCCTCGGCAGCCC |
| M. balbisiana Acc. ITC0545 (SEQ ID NO 28) | GCTGCTCGTGACGTTGTTGGCCTTCTTCGCCACCGACTCCTCGGCAGCCC |
| M. balbisiana Acc. ITC0080 (SEQ ID NO 29) | GCTGCTCGTGACGTTGTTGGCCTTCTTCGCCACCGACTCCTCGGCAGCCC |
| M. balbisiana Acc. ITC1527 (SEQ ID NO 30) | GCTGCTCGTGACGTTGTTGGCCTTCTTCGCCACCGACTCCTCGGCAGCCC |
| M. balbisiana Acc. ITC1016 (SEQ ID NO 26) | GTGTCGCACCCCGTCCGCACTCCCTCGCCAGAGGTAGGTAGATAAATATG |
| M. balbisiana Acc. ITC0545 (SEQ ID NO 28) | GTGTCGCACCCCGTCCGCACTCCCTCGCCAGAGGTAGGTAGATAAATATG |
| M. balbisiana Acc. ITC0080 (SEQ ID NO 29) | GTGTCGCACCCCGTCCGCACTCCCTCGCCAGAGGTAGGTAGATAAATATG |
| M. balbisiana Acc. ITC1527 (SEQ ID NO 30) | GTGTCGCACCCCGTCCGCACTCCCTCGCCAGAGGTAGGTAGATAAATATG |
| M. balbisiana Acc. ITC1016 (SEQ ID NO 26) | CATGCGAACTTGTATAT--GATTGGGCTGGAGATCGAGGCATCGTTAATT |
| M. balbisiana Acc. ITC0545 (SEQ ID NO 28) | CATGCGAACTTGTATAT--GATTGGGCTGGAGATCGAGGCATCGTTAATC |
| M. balbisiana Acc. ITC0080 (SEQ ID NO 29) | CATGCGAACATGTATATATATGATTGGGCTGGAGATCGAGGCATCGTTAATC |
| M. balbisiana Acc. ITC1527 (SEQ ID NO 30) | CATGCGAACTTGTATAT--GATTGGGCTGGAGATCGAGGCATCGTTAATC |

FIG. 5 Continued

```
M. balbisiana Acc. ITC1016 (SEQ ID NO 26)  CCGTCTTCATGCTGCAGCGGCACTGAGTGCGTTGGGGTAAGGCAAGATG
M. balbisiana Acc. ITC0545 (SEQ ID NO 28)  CCGTCTTCATGCTGCAGCGGCACTGAGTGCGTTGGGGTAAAGC::::::
M. balbisiana Acc. ITC0080 (SEQ ID NO 29)  CCGTCTTCATGCTGCAGCGGCACTGAGTGCGTTGGGGTAAGGCAAGATG
M. balbisiana Acc. ITC1527 (SEQ ID NO 30)  CCGTCTTCATGCTGCAGCGGCACTGAGTGCGTTGGGGTAAGGCAAGATG M. balbisiana Acc. ITC1016 (SEQ ID NO 26)  CGCCGTGCTGCACATGCGTCTGTCCTCTCATTTACCCACCTCCTTTTGC
M. balbisiana Acc. ITC0545 (SEQ ID NO 28)  ::::::::::::::::::::::::::::::::::::::::::::::::
M. balbisiana Acc. ITC0080 (SEQ ID NO 29)  CGCCGTGCTGCACATGCGTCTGTCCTCTCATTTACCCACCTCCTTTTTGC
M. balbisiana Acc. ITC1527 (SEQ ID NO 30)  CGCCGTGCTGCACATGCGTCTGTCCTCTCATTTACCCACCTCCTTTTTGC M. balbisiana Acc. ITC1016 (SEQ ID NO 26)  TTTTGCGGCGGCGTATGGCAAGGCTCCTGCCCGTCCGCCTGCACCAACTG
M. balbisiana Acc. ITC0545 (SEQ ID NO 28)  ::::::::::::::::::::::CCCTTCCGCCTGCACCAACTG
M. balbisiana Acc. ITC0080 (SEQ ID NO 29)  TTTTGCGGCGGCGTATGGCAAGGCTCCTGCCCGTCCGCCTGCACCAACTG
M. balbisiana Acc. ITC1527 (SEQ ID NO 30)  TTTTGCGGCGGCGTMTGGCAAGGCTCCTGCCCGTCCGCCTGCACCAACTG M. balbisiana Acc. ITC1016 (SEQ ID NO 26)  CGAGTGTGTCCTCAACGAGTGCACTTGCATCGATCGTGTGGACCCCAAGG
M. balbisiana Acc. ITC0545 (SEQ ID NO 28)  CGAGTGTGTCCTCAACGAGTGCACTTGCATCGATCGTGTGGACCCCAAGG
M. balbisiana Acc. ITC0080 (SEQ ID NO 29)  CGAGTGTGTCCTCAACGAGTGCACTTGCATCGATCGTGGACCCCAAGG
M. balbisiana Acc. ITC1527 (SEQ ID NO 30)  CGAGTGTGTCCTCAACGAGTGCACTTGCATCGATCGTGTGGACCCCAAGG
```

FIG. 5 Continued

| | | |
|---|---|---|
| M. balbisiana Acc. ITC1016 | (SEQ ID NO 26) | CCTGCGAGGCCGACTCCTGTG:CCGGCT----CGATGCAGCAGCCCCCAAAGT |
| M. balbisiana Acc. ITC0545 | (SEQ ID NO 28) | CCTGCGAGGCCGACTCCTGTG:CCGGCTGGCTCGATGCAGCCCCCAAAGT |
| M. balbisiana Acc. ITC0080 | (SEQ ID NO 29) | CCTGCGTGCCGACTCCTGTG:CCGGCT----CGATGCAGCAGCCCCCAAAGT |
| M. balbisiana Acc. ITC1527 | (SEQ ID NO 30) | CCTGCGAGGCCGACTCCTGTG:CCGGCTGGCTCGATGCAGCCCCCAAAGT |
| M. balbisiana Acc. ITC1016 | (SEQ ID NO 26) | AGAGCCGTCGCAGCAGTGGGCGACCGAAGAAACCGTGGGAAATTAGGGA |
| M. balbisiana Acc. ITC0545 | (SEQ ID NO 28) | AGAGCCGTCGCAGCAGTGGGCGACCGAAGAAACCGTGGGAAATTAGGGA |
| M. balbisiana Acc. ITC0080 | (SEQ ID NO 29) | AGAGCCGTCGCAGCAGTGGGCGACCGAAGAAACCGTGGGAAATTAGGGA |
| M. balbisiana Acc. ITC1527 | (SEQ ID NO 30) | AGAGCCGTCGCAGCAGTGGGCGACCGAAGAAACCGTGGGAAATTAGGGA |
| M. balbisiana Acc. ITC1016 | (SEQ ID NO 26) | CGATGGTGtgaTCCAATTGTGTTTGTGA |
| M. balbisiana Acc. ITC0545 | (SEQ ID NO 28) | CGATGGTGtgaTCCAA |
| M. balbisiana Acc. ITC0080 | (SEQ ID NO 29) | CGATGGTGtgaTCCAATTGTGTTTGTGA |
| M. balbisiana Acc. ITC1527 | (SEQ ID NO 30) | CGATGGTGtgaTCCAATTGTGTTTGT |

IDENTIFICATION OF RESISTANCE GENES FROM WILD RELATIVES OF BANANA AND THEIR USES IN CONTROLLING PANAMA DISEASE

CROSS REFERENCE TO RELATED APPLICATIONS

This application is a divisional application of U.S. patent application Ser. No. 16/896,682 filed on Jun. 9, 2020, which claims the benefit of U.S. Provisional Patent Application No. 62/866,872, filed on Jun. 26, 2019, and of U.S. Provisional Patent Application No. 62/912,010, filed on Oct. 7, 2019, the entire contents of each of which are herein incorporated by reference.

FIELD

The present disclosure generally relates to the field of agricultural industry, especially production of consumer crops with pathogenic resistance. More particularly, the present disclosure relates to compositions and methods for generating plants that possess traits resistant to fungal pathogens such as the soil-born *Fusarium* fungi and/or that show resistance to diseases caused by said fungal pathogens.

DESCRIPTION OF THE TEXT FILE SUBMITTED ELECTRONICALLY

The Sequence Listing associated with this application is provided in text format in lieu of a paper copy. The contents of the text file submitted electronically herewith are incorporated herein by reference in their entirety: A computer readable format copy of the Sequence Listing (filename: EVOL_009_03US_SeqList_ST25.txt, date recorded: Apr. 29, 2022; file size: 27.0 kilobytes).

BACKGROUND OF THE DISCLOSURE

Bananas are one of the world's biggest fruit crops, totaling over 100 million metric tons. Bananas are the most popular fruit in developed countries, and are an important food and income source for a large percentage of the world, providing food security in many tropical and subtropical nations. In fact, bananas are the fourth most important food crop in developing nations where the vast majority of bananas are produced and consumed locally. The major producing countries are India, China, Ecuador, Brazil, and some African countries.

About 15 percent of banana production is traded on the global market, generating about $8 Billion annually. The top exporting countries are Ecuador, Philippines, Costa Rica, and Columbia.

However, this important crop is now severely threatened by Fusarium Wilt, also known as Panama Disease, caused by the fungus *Fusarium oxysporum* f sp. *cubense* (Foc).

Half of the commercial banana crop world-wide and even up to 90% of banana exports in some countries consist of a single group of cultivars, the Cavendish genotypes, which are propagated clonally. Also, most of the commercially traded bananas and many of the locally consumed bananas are clonally cultivated with a single crop in a given area, known as 'monoculture.' The monoculture has been widely practiced by farmers to mass-produce highly demanded crops such as banana, which is easily affected by a range of fungal, viral, bacterial and nematode diseases. Clearly, the current expansion of the Panama disease epidemic is particularly destructive due to the massive monoculture of susceptible Cavendish bananas.

Cavendish bananas are the fruits of one of a number of banana cultivars belonging to the Cavendish subgroup of the AAA banana cultivar group. The same term is also used to describe the plants on which the bananas grow. They include commercially important cultivars like 'Dwarf Cavendish' (1888) and 'Grand Nain' (the "Chiquita banana"). 'Williams' is a cultivar of the 'Giant Cavendish' type in the Cavendish subgroup. It is one of the most widely grown cultivars in commercial plantations. 'Formosana' is another name for the somaclonal variant 'GCTCV-218,' which has some resistance to Fusarium wilt TR4. Other representative commercial cultivars include 'Masak Hijau' and 'Robusta.' Since the 1950s, these cultivars have been the most internationally traded bananas. They replaced the Gros Michel banana (commonly known as Kampala banana in Kenya and Bogoya in Uganda) after it was devastated by Panama disease.

Thus, there is an urgent need in the art for bananas that are resistant to Fusarium Wilt or Panama Disease.

SUMMARY OF THE DISCLOSURE

The present disclosure solves the aforementioned Panama Disease problem by identifying the underlying genetic architecture giving rise to resistance. Furthermore, the disclosure teaches methodology by which this resistance genetic architecture can be imported into disease susceptible bananas and thus render these bananas disease resistant. The importation of this genetic architecture can take many forms, as elaborated upon herein, including: traditional plant breeding, transgenic genetic engineering, next generation plant breeding (CRISPR, base editing, MAS, etc.), and other methods.

In some embodiments as provided herein are isolated nucleic acid molecules comprising nucleic acid sequence SEQ ID NO: 14 coding for susceptibility to *Fusarium oxysporum* race 4 when expressed in a plant, wherein SEQ ID NO: 14 is modified by one, two, three or four nucleic acid substitutions so that the resulting nucleic acid sequence codes for resistance to *Fusarium oxysporum* race 4 when expressed in a plant. In some embodiments, the isolated nucleic acid molecule includes nucleic acid substitutions comprising replacing a T corresponding to position 148 of SEQ ID NO: 14 with a G (148T>G). In some embodiments, the isolated nucleic acid molecule includes nucleic acid substitutions comprising replacing a T corresponding to position 323 of SEQ ID NO: 14 with an A (323T>A). In some embodiments, the isolated nucleic acid molecule includes nucleic acid substitutions comprising replacing a G corresponding to position 344 of SEQ ID NO: 14 with a C (344G>C). In some embodiments, the isolated nucleic acid molecule includes nucleic acid substitutions comprising replacing an A corresponding to position 347 of SEQ ID NO: 14 with a T (347A>T). In some embodiments, the isolated nucleic acid molecule includes nucleic acid substitutions comprising replacing a T corresponding to position 323 with an A (323T>A), replacing a G corresponding to position 344 with a C (344G>C), and replacing an A corresponding to position 347 with a T (347A>T), and wherein all positions are based on SEQ ID NO: 14. In some embodiments the isolated nucleic acid molecule of SEQ ID NO: 14 codes for an amino acid sequence of SEQ ID NO: 15 and wherein the nucleic acid substitutions result in replacing a Leucine corresponding to position 50 of SEQ ID NO: 15 with a Valine (50L>V). In some embodiments, the isolated nucleic acid molecule includes SEQ ID NO: 14 which codes for an amino acid sequence of SEQ ID NO: 15 and wherein the nucleic acid substitutions result in replacing a Valine corresponding to position 108 of SEQ ID NO: 15 with a Glutamic Acid (108V>E). In some embodiments, the isolated nucleic acid includes a SEQ ID NO: 14 which codes for an amino acid sequence of SEQ ID NO: 15 and wherein the nucleic acid substitutions result in replacing an Arginine corresponding to position 115 of SEQ ID NO: 15 with a Proline (115R>P). In some embodiments, the isolated nucleic acid molecule includes a SEQ ID NO: 14 which codes for an amino acid sequence of SEQ ID NO: 15 and wherein the nucleic acid substitutions result in replacing an Aspartic Acid corresponding to position 116 of SEQ ID NO: 15 with a Valine (116D>V). In some embodiments, the isolated nucleic acid molecule includes a SEQ ID NO: 14 which codes for an amino acid sequence of SEQ ID NO: 15 and wherein the nucleic acid substitutions result in replacing a Valine corresponding to position 108 of SEQ ID NO: 15 with a Glutamic Acid (108V>E), an Arginine corresponding to position 115 of SEQ ID NO: 15 with a Proline (115R>P), and an Aspartic Acid corresponding to position 116 of SEQ ID NO: 15 with a Valine (116D>V).

In some embodiments, the expression occurs in a plant cell, plant tissue, plant cell culture, plant tissue culture, or whole plant. In some embodiments the expression occurs in a *Musa* cell, tissue, cell culture, tissue culture, or whole plant. In some embodiments, the expression occurs in a *Musa acuminata* cell, tissue, cell culture, tissue culture or whole plant.

In some embodiments, a nucleic acid construct comprises the nucleic acid sequences of the present invention which are operably linked to a promoter capable of driving expression of the nucleic acid sequence. In some embodiments, the promoter is a plant promoter. In some embodiments, the promoter is a 35S promoter. In some embodiments, the promoter is coded by SEQ ID NO: 31.

In some embodiments, a transformation vector comprises the nucleic acid constructs of the present invention.

In some embodiments, provided herein is a method of transforming a plant cell comprising introducing the transformation vectors of the present invention into a plant cell, whereby the transformed plant cell expresses the nucleic acid sequence coding for resistance to *Fusarium oxysporum* race 4. In some embodiments, the method uses a plant cell which is a *Musa* plant cell. In some embodiments, the method uses a plant cell which is a *Musa acuminata* plant cell.

In some embodiments, the transformed plant tissue is produced from the transformed plant cell. In some embodiments, a transformed plantlet is produced from the transformed plant tissue. In some embodiments, a clone is produced from the transformed plantlet. In some embodiments, the method comprises growing the transformed plantlet or clone of the transformed plantlet into a mature transformed plant. In some embodiments, the mature transformed plant is a *Musa* plant and the mature transformed *Musa* plant is capable of producing fruit. In some embodiments, the methods of the present invention include further producing clones of the mature transformed *Musa* plant. In some embodiments, the mature transformed *Musa* plant or clone of the mature transformed *Musa* plant are used in breeding methods.

In some embodiments, the present invention provides an isolated amino acid molecule comprising an amino acid sequence of SEQ ID NO: 15 coding for a protein that when produced in a plant results in susceptibility to *Fusarium oxysporum* race 4, wherein SEQ ID NO: 15 is modified by one, two, three or four amino acid substitutions so that it codes for a protein which when produced in a plant results in resistance to *Fusarium oxysporum* race 4. In some embodiments, the amino acid substitutions comprise replacing a Leucine corresponding to position 50 of SEQ ID NO: 15 with a Valine (50L>V). In some embodiments, the amino acid substitutions comprise replacing a Valine corresponding to position 108 of SEQ ID NO: 15 with a Glutamic Acid (108V>E). In some embodiments, the amino acid substitutions comprise replacing an Arginine corresponding to position 115 of SEQ ID NO: 15 with a Proline (115R>P). In some embodiments, the amino acid substitutions comprise replacing an Aspartic Acid corresponding to position 116 of SEQ ID NO: 15 with a Valine (116D>V). In some embodiments, the amino acid substitutions comprise replacing a Valine corresponding to position 108 of SEQ ID NO: 15 with a Glutamic Acid (108V>E), an Arginine corresponding to position 115 of SEQ ID NO: 15 with a Proline (115R>P), and an Aspartic Acid corresponding to position 116 of SEQ ID NO: 15 with a Valine (116D>V). In some embodiments, the protein production occurs in a plant cell, plant tissue, plant cell culture, plant tissue culture, or whole plant. In some embodiments, the protein production occurs in a *Musa* cell, tissue, cell culture, tissue culture, or whole plant. In some embodiments, the protein production occurs in a *Musa acuminata* cell, tissue, cell culture, tissue culture or whole plant.

In some embodiments, the nucleic acid constructs of the present invention comprise a nucleic acid sequence coding for resistance to *Fusarium oxysporum* race 4 when expressed in a plant, wherein said nucleic acid sequence is selected from the group consisting of SEQ ID NO: 2, SEQ ID NO: 5, SEQ ID NO: 9, SEQ ID NO: 11, SEQ ID NO: 18, SEQ ID NO: 21, SEQ ID NO: 24 and SEQ ID NO: 29, and wherein the nucleic acid sequence is operably linked to a promoter capable of driving expression of the nucleic acid sequence. In some embodiments, the promoter is a plant promoter. In some embodiments, the promoter is a 35S promoter. In some embodiments, the promoter is coded by SEQ ID NO: 31. In some embodiments, a transformation vector comprises the nucleic acid constructs of the present invention. In some embodiments, the present invention provides methods of transforming a plant cell comprising introducing the transformation vector into a plant cell, whereby the transformed plant cell expresses the nucleic acid sequence coding for resistance to *Fusarium oxysporum* race 4. In some embodiments, the plant cell is a *Musa* plant cell. In some embodiments, the plant cell is a *Musa acuminata* plant cell. In some embodiments, the methods further comprise producing transformed plant tissue from the transformed plant cell. In some embodiments, a transformed plantlet is produced from the transformed plant tissue. In some embodiments, the methods further comprise producing a clone of the transformed plantlet. In some embodiments, the methods further comprise growing the transformed plantlet or clone of the transformed plantlet into a mature transformed plant. In some embodiments, the mature transformed plant is a *Musa* plant and the mature transformed *Musa* plant is capable of producing fruit. In some embodiments, the methods further comprise producing clones of the mature transformed *Musa* plant. In some embodiments, the mature transformed *Musa* plant or clone of the mature transformed *Musa* plant is used in a breeding method.

In some embodiments, the invention provides a banana breeding method comprising crossing a first *Musa* plant comprising a nucleic acid sequence coding for resistance to *Fusarium oxysporum* race 4 with a second *Musa* plant that is susceptible to *Fusarium oxysporum* race 4 and selecting resultant progeny of the cross based on their resistance to *Fusarium oxysporum* race 4, wherein said nucleic acid sequence coding for resistance to *Fusarium oxysporum* race 4 is selected from the group consisting of SEQ ID NO: 2, SEQ ID NO: 5, SEQ ID NO: 9, SEQ ID NO: 11, SEQ ID NO: 18, SEQ ID NO: 21, SEQ ID NO: 24 and SEQ ID NO: 29. In some embodiments, the banana breeding methods further comprise producing clones of the resultant progeny of the cross wherein the clones are selected based on their resistance to *Fusarium oxysporum* race 4. In some embodiments, the first and second *Musa* plants are from different *Musa* species. In some embodiments, the first and second *Musa* plants are from the same *Musa* species. In some embodiments, the first and/or second *Musa* plant is a *Musa acuminata* plant. In some embodiments, the progeny of the cross that display resistance to *Fusarium oxysporum* race 4 are selected using molecular markers that are designed based on the nucleic acid sequence coding for resistance to *Fusarium oxysporum* race 4 that is present in the first *Musa* plant used in the cross.

In some embodiments, the present invention provides methods for obtaining a *Musa acuminata* plant cell with a silenced endogenous gene coding for susceptibility to *Fusarium oxysporum* race 4, the method comprising introducing a double-strand break to at least one site in an endogenous gene coded by SEQ ID NO: 14 to produce a *Musa acuminata* plant cell with a silenced endogenous gene coding for susceptibility to *Fusarium oxysporum* race 4. In some embodiments, the methods further comprise generating a *Musa acuminata* plant from the *Musa acuminata* plant cell with a silenced endogenous gene coding for susceptibility to *Fusarium oxysporum* race 4 to produce a *Musa acuminata* plant with a silenced endogenous gene coding for susceptibility to *Fusarium oxysporum* race 4. In some embodiments, the methods further comprise using the *Musa acuminata* plant with a silenced endogenous gene coding for susceptibility to *Fusarium oxysporum* race 4 in a banana breeding program. In some embodiments, the methods of the present invention utilize a plant cell that is the *Musa acuminata* plant cell with a silenced endogenous gene coding for susceptibility to *Fusarium oxysporum* race 4. In some embodiments, the double-strand break is induced by a nuclease selected from the group consisting of a TALEN, a meganuclease, a zinc finger nuclease, and a CRISPR-associated nuclease. In some embodiments, the double-strand break is induced by a CRISPR-associated nuclease and where a guide RNA is provided.

In some embodiments, the present invention provides methods for producing a plant cell resistant to *Fusarium oxysporum* race 4 comprising introducing at least one genetic modification into one or more endogenous nucleic acid sequences coding for susceptibility to *Fusarium oxysporum* race 4, wherein the genetic modification confers resistance to *Fusarium oxysporum* race 4 to the plant cell. In some embodiments, at least one genetic modification is introduced by a TALEN, a meganuclease, a zinc finger nuclease or a CRISPR-associated nuclease. In some embodiments, the at least one genetic modification is introduced by a CRISPR-associated nuclease and an associated guide RNA. In some embodiments, the at least one genetic modification is selected from the list consisting of replacing a T corresponding to position 148 of SEQ ID NO: 14 with a G (148T>G), replacing a T corresponding to position 323 of SEQ ID NO: 14 with an A (323T>A), replacing a G corresponding to position 344 of SEQ ID NO: 14 with a C (344G>C), and replacing an A corresponding to position 347 of SEQ ID NO: 14 with a T (347A>T). In some embodiments, the at least one genetic modification results in a change in an amino acid selected from the group consisting of replacing a Leucine corresponding to position 50 of SEQ ID NO: 15 with a Valine (50L>V), replacing a Valine corresponding to position 108 of SEQ ID NO: 15 with a Glutamic Acid (108V>E), replacing an Arginine corresponding to position 115 of SEQ ID NO: 15 with a Proline (115R>P), and replacing an Aspartic Acid corresponding to position 116 of SEQ ID NO: 15 with a Valine (116D>V). In some embodiments, the plant cell is a *Musa* plant cell. In some embodiments, the plant cell is a *Musa acuminata* plant cell. In some embodiments, the methods further comprise producing transformed plant tissue from the transformed plant cell. In some embodiments, the methods further comprise producing a transformed plantlet from the transformed plant tissue. In some embodiments, the methods further comprise producing a clone of the transformed plantlet. In some embodiments, the methods further comprise growing the transformed plantlet or clone of the transformed plantlet into a mature transformed plant. In some embodiments, the mature transformed plant is a *Musa* plant and the mature transformed *Musa* plant is capable of producing fruit. In some embodiments, the methods further comprise producing clones of the mature transformed *Musa* plant. In some embodiments, the methods further comprise using the mature transformed *Musa* plant or clone of the mature transformed *Musa* plant in a breeding method.

BRIEF DESCRIPTION OF THE DRAWINGS

FIG. 1 illustrates banana FusR1 coding sequences aligned. Initiation (start) and termination (stop) codons are underlined.

Figure 3:
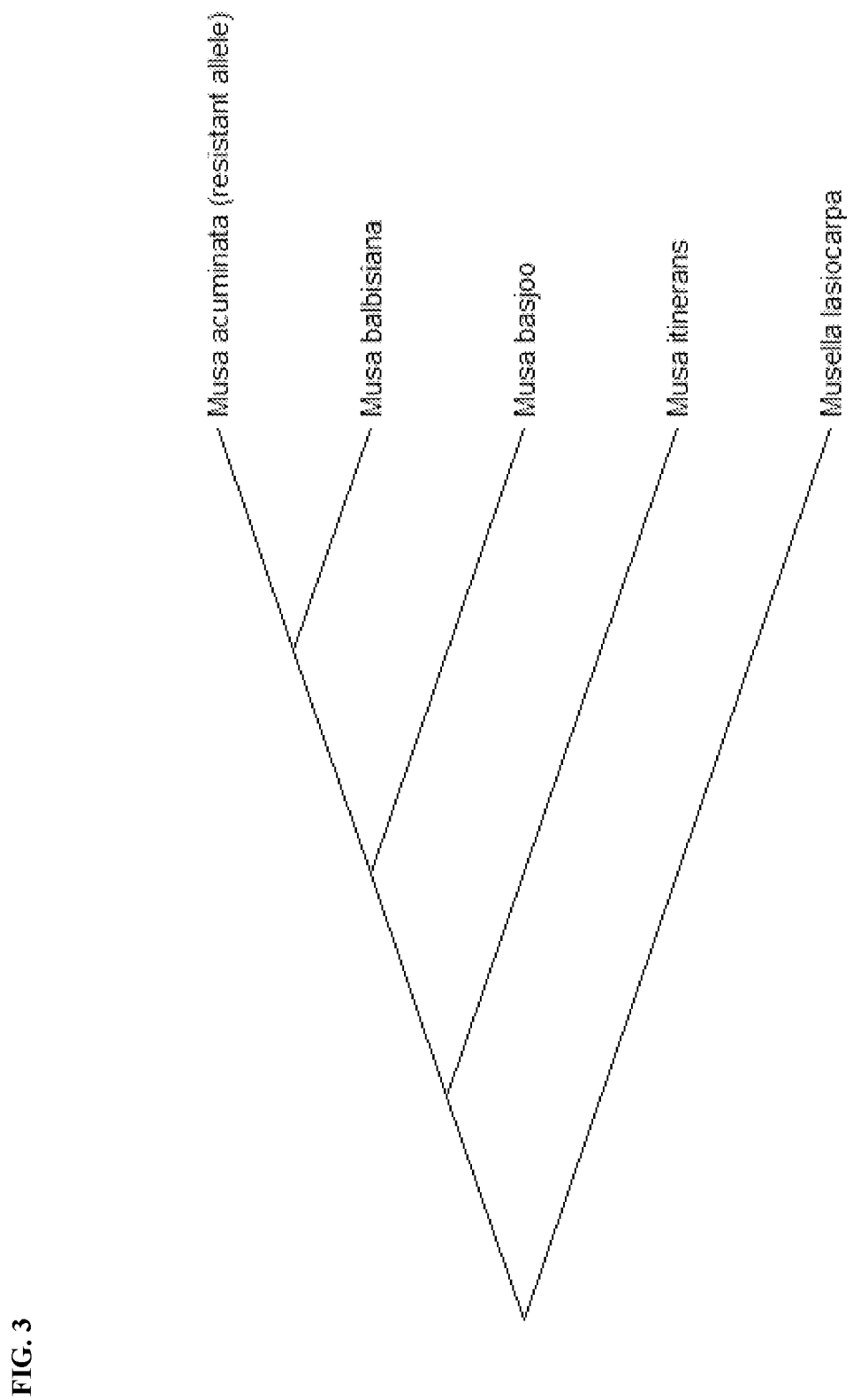
Figure 4:
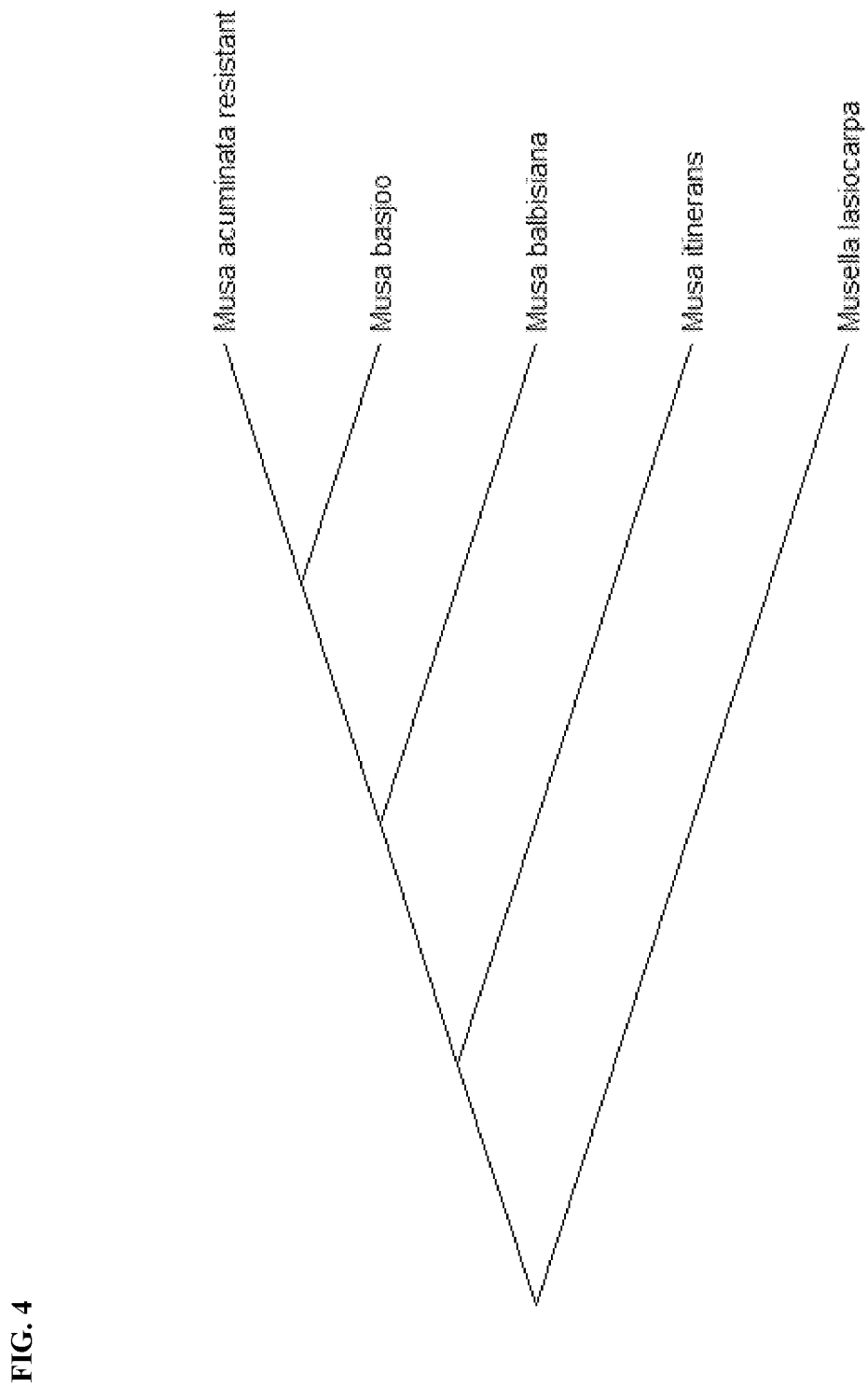

FusR1 nucleotide base substitutions between *Musa* species are bolded. Substitutions that code for replacement amino acid residues (i.e., are nonsynonymous) are shown in bolded font with an asterisk (*); silent substitutions are shown in bolded font with a dot (•). The first 96 bases code for a leader peptide (shown in lower case) that is cleaved from the mature protein. This is known to be common for Bowman-Birk proteins (Barbosa et al., 2007). Inventor confirmed the extent of the leader sequence using two different bioinformatics tools, SignalP-5.0 (Armenteros et al, 2019), and PrediSi (Hiller et al., 2004), which both identified the same leader peptide. Using the bioinformatics tool DeepLoc-1.0 (Armenteros et al., 2017), inventor then established that the mature FUSR1 protein is localized to the cell cytoplasm (likelihood of 0.9732).

Bases shown in UPPER CASE code for the mature protein.

A missing base, shown as a dash (-), in the *M. balbisiana* FusR1 sequence results in a premature stop codon (shown in *italicized, underlined lower case*), relative to the other FusR1 sequences. As described in the text, FusR1 mRNAs from all *M. balbisiana* accessions inventor examined have an unspliced (i.e., expressed) intron; for clarity in the Figure and to focus on sequence similarities/differences in FusR1 coding sequences from different banana species, the intron sequence has been removed here from *M. balbisiana*, even though inventor has not seen that happen. Thus SEQ ID NO: 27 is a 'hypothetical'' coding sequence.

The *M. itinerans* FusR1 sequence was obtained from multiple accessions (ITC1526, ITC1571, and PT-BA-00223), all of which are FW-resistant. The *M. acuminata* FusR1 sequence labeled 'FW-resistant' was obtained from multiple FW-resistant accessions, including ITC0896 (*M. a.* subspecies *banksii*) and PT-BA-00281 (Pisang Bangkahulu). The *M. acuminata* sequence labeled 'sensitive' is from FW-sensitive accessions ITC0507, ITC0685, PT-BA-00304, PT-BA-00310, and PT-BA-00315. These accessions include multiple samples from banana cultivars such as Pisang Madu, Pisang Pipit, and Pisang Rojo Uter, all of which have been well-characterized as FW-sensitive (Chen et al, 2019). The *M. balbisiana* sequence included here was obtained from ITC1016. FusR1 from *M. basjoo* is from FW-resistant accessions (ITC0061 and PD #3064).

Examination of FIG. 1 reveals that our FusR1 banana sequences are well-conserved in the region that codes for the leader peptide, as is expected. However, the FusR1 sequence that codes for the mature FUSR1 protein shows an unusually high number of nonsynonymous substitutions. This is the result of severe selective pressure on these proteins, which is reflected in the elevated Ka/Ks ratios seen for these genes. (See below.) Inventor found 2 FW-resistant alleles for FusR1 from *M. itinerans*. These differ very slightly and for simplicity, only Allele 1 (SEQ ID NO: 2) from *M. itinerans* is shown in FIG. 1. The Allele 2 coding sequence from *M. itinerans* is included in the Sequence Listing as SEQ ID NO: 5. Similarly, inventor found 2 FusR1 FW-resistant alleles in *M. acuminata*. These differ only by a single silent base substitution. Again, for simplicity, FIG. 1 shows only one of these alleles (SEQ ID NO: 9). The second allele, not shown in FIG. 1, is recorded in the Sequence Listing as SEQ ID NO: 11.

FIG. 2 illustrates banana FUSR1 protein sequences aligned. Amino acid residues that differ between the banana FUSR1 protein sequences are underlined. The first 32 residues constitute a leader peptide which is cleaved from the mature protein. Leader sequence residues are shown in lower case, and mature protein residues in UPPER CASE.

The functional folded banana FUSR1 protein consists of two subdomains: Subdomain 1 is indicated by light grey shading; Subdomain 2 is indicated by dark grey shading. As in other Bowman-Birk proteins, banana FUSR1 structure is maintained by 14 disulfide bonds. The cysteine residues that form these disulfide bonds are shown in bold. Each subdomain contains a reactive site, shown in italics. Residues that are specific for trypsin (Subdomain 1) and chymotrypsin (Subdomain 2) are indicated by an asterisk (*). For *M. acuminata*, residues that differ between the Foc4-sensitive FusR1 allele and the Foc-4 resistant alleles are shown by a dot (•), with the arginine residue (number 115) that explains Foc4 sensitivity shown in bold font with a dot (•).

FIG. 3 provides a phylogenetic tree for several banana species, based on nucleotide sequences of the C2H2 gene.

The tree topology shown here was recovered from analysis of our banana C2H2 nucleotide sequences. This topology is identical to that recovered from analysis of the C2H2 protein sequence. The same tree was recovered from our TOPO6 nucleotide and protein sequences. The topology shown here is also similar to that in references.

It is important note that in contrast, topologies recovered from the FusR1 protein sequences and the protein-coding regions of the FusR1 gene give a different topology, which is clearly the result of the selective pressures imposed on FusR1 during adaptation due to challenge by *Fusarium*. The non-coding regions of FusR1 have the same topology as the phylogenetic trees for C2H2 and TOPO6.

The evolutionary history was inferred using the Maximum Parsimony method. The single most parsimonious tree is shown. The consistency index is 1.000000, the retention index is 1.000000, and the composite index is 1.000000 for all sites. The MP tree was obtained using the Subtree-Pruning-Regrafting (SPR) algorithm with search level 0 in which the initial trees were obtained by the random addition of sequences (10 replicates). This analysis involved 5 nucleotide sequences. Codon positions included were 1st+2nd+3rd+Noncoding. All positions with less than 95% site coverage were eliminated, i.e., fewer than 5% alignment gaps, missing data, and ambiguous bases were allowed at any position (partial deletion option). There were a total of 218 positions in the final dataset. Evolutionary analyses were conducted in MEGA X (Kumar et al. 2018).

FIG. 4 provides a phylogenetic tree for several banana species, based on FUSR1 protein sequences. Note that this tree unites *Musa acuminata* and *M. basjoo*, in contrast to their actual phylogenetic relationship. *M. acuminata* is most closely related to *M. balbisiana*, with *M. basjoo* as a sister taxon to these 2 species. However, because of the severe effects of positive selection, the FusR1 protein sequence of *M. acuminata* and *M. basjoo* cluster together. (In fact, these protein sequences are identical.)

The evolutionary history was inferred using the Maximum Parsimony method. The single most parsimonious tree with length=55 is shown. The consistency index is 0.963636, the retention index is 0.875000, and the composite index is 0.843182 for all sites. The MP tree was obtained using the Subtree-Pruning-Regrafting (SPR) algorithm with search level 0 in which the initial trees were obtained by the random addition of sequences (10 replicates). Evolutionary analyses were conducted in MEGA X.

FIG. 5 provides the alignment of FusR1 mRNA sequences from FW-sensitive *Musa balbisiana* accessions. The sequences included here were obtained from many *M. balbisiana* accessions, including ITC1016, ITC0545, ITC0080, ITC1527, ITC0565, ITC1781, ITC1580, and several others.

FusR1 nucleotide base substitutions between *Musa balbisiana* accessions are in italics. Start and termination (stop) codons are shown in lower case. Insertions, relative to other *M. balbisiana* accessions (as well as to FusR1 sequences from all other plants inventor analyzed), are bolded. Nucleotide deletions are shown by the colon symbol (:). The 85 base pair deletion in FusR1 from accessions ITC0545 and ITC1781 is unique to *M. balbisiana*. As the sequence of FusR1 from ITC1781 is identical to that from ITC0545, ITC1781 is not presented in FIG. 5. Similarly, the single base pair deletion found in these FW-sensitive *M. balbisiana* accessions has not been found in any other FusR1 sequence. However it exists in all *M. balbisiana* accessions inventor analyzed. This single base pair deletion results in a premature termination codon relative to the FusR1 sequences from FW-resistant banana accessions.

All *M. balbisiana* accessions inventor examined had one of the 4 allele types shown here. Several accessions shared identical FusR1 alleles. Thus, for simplicity, only 4 accessions are shown in this figure. These 4 FusR1 alleles are all very similar in nucleotide sequence. There are transcriptional variants between accessions but all these variants have the expressed, non-spliced intron. All accessions also have the single base pair base pair deletion. Three accessions also have an 85 base pair deletion, and several have a 4 base pair insertion.

Thus all these FusR1 sequences are 'broken' and they all code for non-functional FusR1 proteins. Significantly, all these *M. balbisiana* accessions are FW-sensitive.

DETAILED DESCRIPTION OF THE DISCLOSURE

The present disclosure provides a solution of fungal, viral, bacterial and/or nematode diseases by inducing a defense response to many invading pathogens. The present disclosure provides methods of identifying genetic materials that can drive disease resistance and/or fungal resistance in plants including banana and in plants and plant parts. Also, the present disclosure provides methods of transferring genetic materials to susceptible banana cultivars in order to give rise to traits of disease and/or fungal resistance. Furthermore, the present disclosure teaches newly-identified genetic components and methods of generating genetically modified plants, plant cells, tissues and seeds, having modified disease resistance.

I. Definitions

Unless stated otherwise, all technical and scientific terms used herein have the same meaning as commonly understood by those of ordinary skill in the art to which the disclosure belongs. While the following terms are believed to be well understood by one of ordinary skill in the art, the following definitions are set forth to facilitate explanation of the presently disclosed subject matter. Although any methods and materials similar or equivalent to those described herein can be used in the practice or testing of the present disclosure, preferred methods and materials are described. The following terms are defined below. These definitions are for illustrative purposes and are not intended to limit the common meaning in the art of the defined terms.

The term "a" or "an" refers to one or more of that entity, i.e., can refer to a plural referent. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used in this specification, the term "and/or" is used in this disclosure to mean either "and" or "or" unless indicated otherwise.

Throughout this specification, unless the context requires otherwise, the words "comprise", or variations such as "comprises" or "comprising", will be understood to imply the inclusion of a stated element or integer or group of elements or integers but not the exclusion of any other element or integer or group of elements or integers.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids. In some embodiments, a fragment of a polypeptide or polynucleotide comprises at least 10%, 20%, 30%, 40%, 50%, 60%, 70%, 80%, 90%, 95%, 96%, 97%, 98%, or 99% of the entire length of the reference polypeptide or polynucleotide. In some embodiments, a polypeptide or polynucleotide fragment may contain 5, 10, 15, 20, 25, 30, 35, 40, 45, 50, 60, 70, 80, 90, 100, 200, 300, 400, 500, 600, 700, 800, 900, 1000, 2000 or more nucleotides or amino acids.

As used herein, the term "codon optimization" implies that the codon usage of a DNA or RNA is adapted to that of a cell or organism of interest to improve the transcription rate of said recombinant nucleic acid in the cell or organism of interest. The skilled person is well aware of the fact that a target nucleic acid can be modified at one position due to the codon degeneracy, whereas this modification will still lead to the same amino acid sequence at that position after translation, which is achieved by codon optimization to take into consideration the species-specific codon usage of a target cell or organism.

As used herein, the term "endogenous" or "endogenous gene," refers to the naturally occurring gene, in the location in which it is naturally found within the host cell genome. "Endogenous gene" is synonymous with "native gene" as used herein. An endogenous gene as described herein can include alleles of naturally occurring genes that have been mutated according to any of the methods of the present disclosure, i.e. an endogenous gene could have been modified at some point by traditional plant breeding methods and/or next generation plant breeding methods.

As used herein, the term "exogenous" refers to a substance coming from some source other than its native source. For example, the terms "exogenous protein," or "exogenous gene" refer to a protein or gene from a non-native source, and that has been artificially supplied to a biological system. As used herein, the term "exogenous" is used interchangeably with the term "heterologous," and refers to a substance coming from some source other than its native source.

The terms "genetically engineered host cell," "recombinant host cell," and "recombinant strain" are used interchangeably herein and refer to host cells that have been genetically engineered by the methods of the present disclosure. Thus, the terms include a host cell (e.g., bacteria, yeast cell, fungal cell, CHO, human cell, plant cell, protoplast derived from plant, callus, etc.) that has been genetically altered, modified, or engineered, such that it exhibits an altered, modified, or different genotype and/or phenotype (e.g., when the genetic modification affects coding nucleic acid sequences), as compared to the naturally-occurring host cell from which it was derived. It is understood that the terms refer not only to the particular recombinant host cell in question, but also to the progeny or potential progeny of such a host cell.

As used herein, the term "heterologous" refers to a substance coming from some source or location other than its native source or location. In some embodiments, the term "heterologous nucleic acid" refers to a nucleic acid sequence that is not naturally found in the particular organism. For example, the term "heterologous promoter" may refer to a promoter that has been taken from one source organism and utilized in another organism, in which the promoter is not naturally found. However, the term "heterologous promoter" may also refer to a promoter that is from within the same source organism, but has merely been moved to a novel location, in which said promoter is not normally located.

Heterologous gene sequences can be introduced into a target cell by using an "expression vector," which can be a eukaryotic expression vector, for example a plant expression vector. Methods used to construct vectors are well known to a person skilled in the art and described in various publications. In particular, techniques for constructing suitable vectors, including a description of the functional components such as promoters, enhancers, termination and polyadenylation signals, selection markers, origins of replication, and splicing signals, are reviewed in the prior art. Vectors may include but are not limited to plasmid vectors, phagemids, cosmids, artificial/mini-chromosomes (e.g. ACE), or viral vectors such as baculovirus, retrovirus, adenovirus, adeno-associated virus, herpes simplex virus, retroviruses, bacteriophages. The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operatively linked, are well known in the art and some are commercially available from companies such as Stratagene, La Jolla, Calif; Invitrogen, Carlsbad, Calif.; Promega, Madison, Wis. or BD Biosciences Clontech, Palo Alto, Calif. In one embodiment the expression vector comprises at least one nucleic acid sequence which is a regulatory sequence necessary for transcription and translation of nucleotide sequences that encode for a peptide/polypeptide/protein of interest.

As used herein, the term "naturally occurring" as applied to a nucleic acid, a polypeptide, a cell, or an organism, refers to a nucleic acid, polypeptide, cell, or organism that is found in nature. The term "naturally occurring" may refer to a gene or sequence derived from a naturally occurring source. Thus, for the purposes of this disclosure, a "non-naturally occurring" sequence is a sequence that has been synthesized, mutated, engineered, edited, or otherwise modified to have a different sequence from known natural sequences. In some embodiments, the modification may be at the protein level (e.g., amino acid substitutions). In other embodiments, the modification may be at the DNA level (e.g., nucleotide substitutions).

As used herein, the term "nucleotide change" or "nucleotide modification" refers to, e.g., nucleotide substitution, deletion, and/or insertion, as is well understood in the art. For example, such nucleotide changes/modifications include mutations containing alterations that produce silent substitutions, additions, or deletions, but do not alter the properties or activities of the encoded protein or how the proteins are made. As another example, such nucleotide changes/modifications include mutations containing alterations that produce replacement substitutions, additions, or deletions, that alter the properties or activities of the encoded protein or how the proteins are made.

As used herein, the term "protein modification" refers to, e.g., amino acid substitution, amino acid modification, deletion, and/or insertion, as is well understood in the art.

The term "next generation plant breeding" refers to a host of plant breeding tools and methodologies that are available to today's breeder. A key distinguishing feature of next generation plant breeding is that the breeder is no longer confined to relying upon observed phenotypic variation, in order to infer underlying genetic causes for a given trait. Rather, next generation plant breeding may include the utilization of molecular markers and marker assisted selection (MAS), such that the breeder can directly observe movement of alleles and genetic elements of interest from one plant in the breeding population to another, and is not confined to merely observing phenotype. Further, next generation plant breeding methods are not confined to utilizing natural genetic variation found within a plant population. Rather, the breeder utilizing next generation plant breeding methodology can access a host of modern genetic engineering tools that directly alter/change/edit the plant's underlying genetic architecture in a targeted manner, in order to bring about a phenotypic trait of interest. In aspects, the plants bred with a next generation plant breeding methodology are indistinguishable from a plant that was bred in a traditional manner, as the resulting end product plant could theoretically be developed by either method. In particular aspects, a next generation plant breeding methodology may result in a plant that comprises: a genetic modification that is a deletion or insertion of any size; a genetic modification that is one or more base pair substitution; a genetic modification that is an introduction of nucleic acid sequences from within the plant's natural gene pool (e.g. any plant that could be crossed or bred with a plant of interest) or from editing of nucleic acid sequences in a plant to correspond to a sequence known to occur in the plant's natural gene pool; and offspring of said plants.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

The terms "polynucleotide," "nucleic acid," and "nucleotide sequence," used interchangeably herein, refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. This term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. It also includes modified nucleic acids such as methylated and/or capped nucleic acids, nucleic acids containing modified bases, backbone modifications, and the like. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" "nucleic acid," and "nucleotide sequence" should be understood to include, as applicable to the embodiments being described, single-stranded (such as sense or antisense) and double-stranded polynucleotides.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

The term "traditional plant breeding" refers to the utilization of natural variation found within a plant population as a source for alleles and genetic variants that impart a trait of interest to a given plant. Traditional breeding methods make use of crossing procedures that rely largely upon observed phenotypic variation to infer causative allele association. That is, traditional plant breeding relies upon observations of expressed phenotype of a given plant to infer underlying genetic cause. These observations are utilized to inform the breeding procedure in order to move allelic variation into germplasm of interest. Further, traditional plant breeding has also been characterized as comprising random mutagenesis techniques, which can be used to introduce genetic variation into a given germplasm. These random mutagenesis techniques may include chemical and/or radiation-based mutagenesis procedures. Consequently, one key feature of traditional plant breeding, is that the breeder does not utilize a genetic engineering tool that directly alters/changes/edits the plant's underlying genetic architecture in a targeted manner, in order to introduce genetic diversity and bring about a phenotypic trait of interest.

A "CRISPR-associated effector" as used herein can thus be defined as any nuclease, nickase, or recombinase associated with the CRISPR (Clustered Regularly Interspaced Short Palindromic Repeats), having the capacity to introduce a single- or double-strand cleavage into a genomic target site, or having the capacity to introduce a targeted modification, including a point mutation, an insertion, or a deletion, into a genomic target site of interest. At least one CRISPR-associated effector can act on its own, or in combination with other molecules as part of a molecular complex. The CRISPR-associated effector can be present as fusion molecule, or as individual molecules associating by or being associated by at least one of a covalent or non-covalent interaction with gRNA and/or target site so that the components of the CRISPR-associated complex are brought into close physical proximity.

A "base editor" as used herein refers to a protein or a fragment thereof having the same catalytic activity as the protein it is derived from, which protein or fragment thereof, alone or when provided as molecular complex, referred to as base editing complex herein, has the capacity to mediate a targeted base modification, i.e., the conversion of a base of interest resulting in a point mutation of interest, which in turn can result in a targeted mutation, if the base conversion does not cause a silent mutation, but rather a conversion of an amino acid encoded by the codon comprising the position to be converted with the base editor. At least one base editor according to the present disclosure temporarily or permanently linked to at least one CRISPR-associated effector, or optionally to a component of at least one CRISPR-associated effector complex.

The term "Cas9 nuclease" and "Cas9" can be used interchangeably herein, which refer to a RNA-guided DNA endonuclease enzyme associated with the CRISPR (Clustered Regularly Interspaced Short Palindromic Repeats), including the Cas9 protein or fragments thereof (such as a protein comprising an active DNA cleavage domain of Cas9 and/or a gRNA binding domain of Cas9). Cas9 is a component of the CRISPR/Cas genome editing system, which targets and cleaves a DNA target sequence to form a DNA double strand breaks (DSB) under the guidance of a guide RNA.

The term "CRISPR RNA" or "crRNA" refers to the RNA strand responsible for hybridizing with target DNA sequences, and recruiting CRISPR endonucleases and/or CRISPR-associated effectors. crRNAs may be naturally occurring, or may be synthesized according to any known method of producing RNA.

The term "tracrRNA" refers to a small trans-encoded RNA. TracrRNA is complementary to and base pairs with crRNA to form a crRNA/tracrRNA hybrid, capable of recruiting CRISPR endonucleases and/or CRISPR-associated effectors to target sequences.

The term "Guide RNA" or "gRNA" as used herein refers to an RNA sequence or combination of sequences capable of recruiting a CRISPR endonuclease and/or CRISPR-associated effectors to a target sequence. Typically gRNA is composed of crRNA and tracrRNA molecules forming complexes through partial complement, wherein crRNA comprises a sequence that is sufficiently complementary to a target sequence for hybridization and directs the CRISPR complex (i.e. Cas9-crRNA/tracrRNA hybrid) to specifically bind to the target sequence. Also, single guide RNA (sgRNA) can be designed, which comprises the characteristics of both crRNA and tracrRNA. Therefore, as used herein, a guide RNA can be a natural or synthetic crRNA (e.g., for Cpf1), a natural or synthetic crRNA/tracrRNA hybrid (e.g., for Cas9), or a single-guide RNA (sgRNA).

The term "guide sequence" or "spacer sequence" refers to the portion of a crRNA or guide RNA (gRNA) that is responsible for hybridizing with the target DNA.

The term "protospacer" refers to the DNA sequence targeted by a guide sequence of crRNA or gRNA. In some embodiments, the protospacer sequence hybridizes with the crRNA or gRNA guide (spacer) sequence of a CRISPR complex.

The term "CRISPR landing site" as used herein, refers to a DNA sequence capable of being targeted by a CRISPR-Cas complex. In some embodiments, a CRISPR landing site comprises a proximately placed protospacer/Protospacer Adjacent Motif combination sequence that is capable of being cleaved by a CRISPR complex.

The term "CRISPR complex", "CRISPR endonuclease complex", "CRISPR Cas complex", or "CRISPR-gRNA complex" are used interchangeably herein. "CRISPR complex" refers to a Cas9 nuclease and/or a CRISPR-associated effectors complexed with a guide RNA (gRNA). The term "CRISPR complex" thus refers to a combination of CRISPR endonuclease and guide RNA capable of inducing a double stranded break at a CRISPR landing site. In some embodiments, "CRISPR complex" of the present disclosure refers to a combination of catalytically dead Cas9 protein and guide RNA capable of targeting a target sequence, but not capable of inducing a double stranded break at a CRISPR landing site because it loses a nuclease activity. In other embodiments, "CRISPR complex" of the present disclosure refers to a combination of Cas9 nickase and guide RNA capable of introducing gRNA-targeted single-strand breaks in DNA instead of the double-strand breaks created by wild type Cas enzymes.

As used herein, the term "directing sequence-specific binding" in the context of CRISPR complexes refers to a guide RNA's ability to recruit a CRISPR endonuclease and/or a CRISPR-associated effectors to a CRISPR landing site.

As used herein, the term "deaminase" refers to an enzyme that catalyzes the deamination reaction. In some embodiments of the present disclosure, the deaminase refers to a cytidine deaminase, which catalyzes the deamination of a cytidine or a deoxycytidine to a uracil or a deoxyuridine, respectively. In other embodiments of the present disclosure, the deaminase refers to an adenosine deaminase, which catalyzes the deamination of an adenine to form hypoxanthine (in the form of its nucleoside inosine), which is read as guanine by DNA polymerase.

As used herein, the term "glycosylase" refers to a family of enzymes involved in base excision repair, classified under EC number EC 3.2.2. Base excision repair is the mechanism by which damaged bases in DNA are removed and replaced. DNA glycosylases catalyze the first step of this process. They remove the damaged nitrogenous base while leaving the sugar-phosphate backbone intact, creating an apurinic/apyrimidinic site, commonly referred to as an AP site. This is accomplished by flipping the damaged base out of the double helix followed by cleavage of the N-glycosidic bond. In some embodiments of the present disclosure, in an expectation of affording a mutation introduction tendency different from that of deaminase and the like, a base excision reaction by hydrolysis of N-glycosidic bond of DNA, and then inducing mutation introduction in a repair process of cells is used. In aspects, an enzyme having cytosine-DNA glycosylase (CDG) activity or thymine-DNA glycosylase (TDG) activity is used. In aspects, a mutant of yeast mitochondrial uracil-DNA glycosylase (UNG 1), is used as an enzyme that performs such base excision reaction. Nishida et al., US 2017/0321210 A1, published on Nov. 9, 2017, is incorporated by reference herein.

As used herein the term "targeted" refers to the expectation that one item or molecule will interact with another item or molecule with a degree of specificity, so as to exclude non-targeted items or molecules. For example, a first polynucleotide that is targeted to a second polynucleotide, according to the present disclosure has been designed to hybridize with the second polynucleotide in a sequence specific manner (e.g., via Watson-Crick base pairing). In some embodiments, the selected region of hybridization is designed so as to render the hybridization unique to the one, or more targeted regions. A second polynucleotide can cease to be a target of a first targeting polynucleotide, if its targeting sequence (region of hybridization) is mutated, or is otherwise removed/separated from the second polynucleotide. Furthermore, "targeted" can be interchangeably used with "site-specific" or "site-directed," which refers to an action of molecular biology which uses information on the sequence of a genomic region of interest to be modified, and which further relies on information of the mechanism of action of molecular tools, e.g., nucleases, including CRISPR nucleases and variants thereof, TALENs, ZFNs, meganucleases or recombinases, DNA-modifying enzymes, including base modifying enzymes like cytidine deaminase enzymes, histone modifying enzymes and the like, DNA-binding proteins, cr/tracr RNAs, guide RNAs and the like.

The term "seed region" refers to the critical portion of a crRNA's or guide RNA's guide sequence that is most susceptible to mismatches with their targets. In some embodiments, a single mismatch in the seed region of a crRNA/gRNA can render a CRISPR complex inactive at that binding site. In some embodiments, the seed regions for Cas9 endonucleases are located along the last ~12 nts of the 3' portion of the guide sequence, which correspond (hybridize) to the portion of the protospacer target sequence that is adjacent to the PAM. In some embodiments, the seed regions for Cpf1 endonucleases are located along the first ~5 nts of the 5' portion of the guide sequence, which correspond (hybridize) to the portion of the protospacer target sequence adjacent to the PAM.

The term "sequence identity" refers to the percentage of bases or amino acids between two polynucleotide or polypeptide sequences that are the same, and in the same relative position. As such one polynucleotide or polypeptide sequence has a certain percentage of sequence identity compared to another polynucleotide or polypeptide sequence. For sequence comparison, typically one sequence acts as a reference sequence, to which test sequences are compared. The term "reference sequence" refers to a molecule to which a test sequence is compared. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988).

"Complementary" refers to the capacity for pairing, through base stacking and specific hydrogen bonding, between two sequences comprising naturally or non-naturally occurring bases or analogs thereof. For example, if a base at one position of a nucleic acid is capable of hydrogen bonding with a base at the corresponding position of a target, then the bases are considered to be complementary to each other at that position. Nucleic acids can comprise universal bases, or inert abasic spacers that provide no positive or negative contribution to hydrogen bonding. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and Santa Lucia, Nucl. Acids Research, 2005; 33 (19): 6258-6267.

As referred to herein, a "complementary nucleic acid sequence" is a nucleic acid sequence comprising a sequence of nucleotides that enables it to non-covalently bind to another nucleic acid in a sequence-specific, antiparallel, manner (i.e., a nucleic acid specifically binds to a complementary nucleic acid) under the appropriate in vitro and/or in vivo conditions of temperature and solution ionic strength.

Methods of sequence alignment for comparison and determination of percent sequence identity and percent complementarity are well known in the art. Optimal alignment of sequences for comparison can be conducted, e.g., by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), by manual alignment and visual inspection (see, e.g., Brent et al., (2003) Current Protocols in Molecular Biology), by use of algorithms know in the art including the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Michigan), using default parameters, and MUSCLE (Multiple Sequence Comparison by Log-Expection; a computer software licensed as public domain).

Herein, the term "hybridize" refers to pairing between complementary nucleotide bases (e.g., adenine (A) forms a base pair with thymine (T) in a DNA molecule and with uracil (U) in an RNA molecule, and guanine (G) forms a base pair with cytosine (C) in both DNA and RNA molecules) to form a double-stranded nucleic acid molecule. (See, e.g., Wahl and Berger (1987) Methods Enzymol. 152:399; Kimmel, (1987) Methods Enzymol. 152:507). In addition, it is also known in the art that for hybridization between two RNA molecules (e.g., dsRNA), guanine (G) base pairs with uracil (U). For example, G/U base-pairing is partially responsible for the degeneracy (i.e., redundancy) of the genetic code in the context of tRNA anti-codon base-pairing with codons in mRNA. In the context of this disclosure, a guanine (G) of a protein-binding segment (dsRNA duplex) of a guide RNA molecule is considered complementary to a uracil (U), and vice versa. As such, when a G/U base-pair can be made at a given nucleotide position a protein-binding segment (dsRNA duplex) of a guide RNA molecule, the position is not considered to be non-complementary, but is instead considered to be complementary. It is understood in the art that the sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted.

The term "modified" refers to a substance or compound (e.g., a cell, a polynucleotide sequence, and/or a polypeptide sequence) that has been altered or changed as compared to the corresponding unmodified substance or compound.

"Isolated" refers to a material that is free to varying degrees from components which normally accompany it as found in its native state.

The term "gene edited plant, part or cell" as used herein refers to a plant, part or cell that comprises one or more endogenous genes that are edited by a gene editing system. The gene editing system of the present disclosure comprises a targeting element and/or an editing element. The targeting element is capable of recognizing a target genomic sequence. The editing element is capable of modifying the target genomic sequence, e.g., by substitution or insertion of one or more nucleotides in the genomic sequence, deletion of one or more nucleotides in the genomic sequence, alteration of genomic sequences to include regulatory sequences, insertion of transgenes at a safe harbor genomic site or other specific location in the genome, or any combination thereof. The targeting element and the editing element can be on the same nucleic acid molecule or different nucleic acid molecules. In some embodiments, the editing element is capable of precise genome editing by substitution of a single nucleotide using a base editor, such cytosine base editor (CBE) and/or adenine base editor (ABE), which is directly or indirectly fused to a CRISPR-associated effector protein.

The term "plant" refers to whole plants. The term "plant part" include differentiated and undifferentiated tissues including, but not limited to: plant organs, plant tissues, roots, stems, shoots, rootstocks, scions, stipules, petals, leaves, flowers, ovules, pollens, bracts, petioles, internodes, bark, pubescence, tillers, rhizomes, fronds, blades, stamens, fruits, seeds, tumor tissue and plant cells (e.g., single cells, protoplasts, embryos, and callus tissue). Plant cells include, without limitation, cells from seeds, suspension cultures, embryos, meristematic regions, callus tissue, leaves, roots, shoots, gametophytes, sporophytes, pollen and microspores. The plant tissue may be in a plant or in a plant organ, tissue or cell culture.

As used herein when discussing plants, the term "ovule" refers to the female gametophyte, whereas the term "pollen" means the male gametophyte.

As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

As used herein, the term "phenotype" refers to the observable characters of an individual cell, cell culture, organism (e.g., a plant), or group of organisms which results from the interaction between that individual's genetic makeup (i.e., genotype) and the environment.

The terms "transgene" or "transgenic" as used herein refer to at least one nucleic acid sequence that is taken from the genome of one organism, or produced synthetically, and which is then introduced into a host cell or organism or tissue of interest and which is subsequently integrated into the host's genome by means of "stable" transformation or transfection approaches. In contrast, the term "transient" transformation or transfection or introduction refers to a way of introducing molecular tools including at least one nucleic acid (DNA, RNA, single-stranded or double-stranded or a mixture thereof) and/or at least one amino acid sequence, optionally comprising suitable chemical or biological agents, to achieve a transfer into at least one compartment of interest of a cell, including, but not restricted to, the cytoplasm, an organelle, including the nucleus, a mitochondrion, a vacuole, a chloroplast, or into a membrane, resulting in transcription and/or translation and/or association and/or activity of the at least one molecule introduced without achieving a stable integration or incorporation and thus inheritance of the respective at least one molecule introduced into the genome of a cell. The terms "transgene-free" refers to a condition that transgene is not present or found in the genome of a host cell or tissue or organism of interest.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, leaves, stems, roots, root tips, anthers, pistils, meristematic cells, axillary buds, ovaries, seed coat, endosperm, hypocotyls, cotyledons and the like. The term "plant organ" refers to plant tissue or a group of tissues that constitute a morphologically and functionally distinct part of a plant. "Progeny" comprises any subsequent generation of a plant.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

As used herein, the term "AGAMOUS Clade Transcription Factor" or "AG Glade transcription factor" is a member of the AGAMOUS (AG) subfamily of MIKC-type MADS-box genes. "MIKC-type" proteins represent a class of MADS-domain transcription factors and are defined by a unique domain structure: (1) 'M'—a highly conserved DNA-binding MADS-domain, (2) 'I'—an intervening domain, (3) 'K'—a keratin-like K-domain, and (4) 'C'—a C-terminal domain. In some embodiments, "AGAMOUS Clade Transcription Factor" or "AG Glade transcription factor" further comprises an N-terminal region. In further embodiments, "AGAMOUS Clade Transcription Factor" or "AG Glade transcription factor" comprises AG, SHP1, SHP2, and STK genes in plants of the present disclosure, each of which has a NN motif in the M domain, a YQQ motif in the K domain, and/or a R/Q (R or Q) in the C domain.

By "biologically active portion" is meant a portion of a full-length parent peptide or polypeptide which portion retains an activity of the parent molecule. For example, a biologically active portion of polypeptide of the disclosure will retain the ability to confer disease resistance, especially resistance to fungal pathogens such as Fusarium. As used herein, the term "biologically active portion" includes deletion mutants and peptides, for example of at least about 8, 9, 10, 11, 12, 13, 14, 15, 16, 17, 18, 19, 20, 21, 22, 23, 24, 25, 30, 40, 50, 60, 70, 80, 90, 100, 120, 150, 300, 400, 500, 600, 700, 800, 900 or 1000 contiguous amino acids, which comprise an activity of a parent molecule. Portions of this type may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "Peptide Synthesis" by Atherton and Shephard which is included in a publication entitled "Synthetic Vaccines" edited by Nicholson and published by Blackwell Scientific Publications. Alternatively, peptides can be produced by digestion of a peptide or polypeptide of the disclosure with proteinases such as endoLys-C, endoArg-C, endoGlu-C and staphylococcus V8-protease. The digested fragments can be purified by, for example, high performance liquid chromatographic (HPLC) techniques. Recombinant nucleic acid techniques can also be used to produce such portions.

By "corresponds to" or "corresponding to" is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein.

The terms "growing" or "regeneration" as used herein mean growing a whole, differentiated plant from a plant cell, a group of plant cells, a plant part (including seeds), or a plant piece (e.g., from a protoplast, callus, or tissue part).

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

By "obtained from" is meant that a sample such as, for example, a nucleic acid extract or polypeptide extract is isolated from, or derived from, a particular source. For example, the extract may be isolated directly from plants, especially monocotyledonous plants and more especially non-graminaceous monocotyledonous plants such as banana.

The term "pathogen" is used herein in its broadest sense to refer to an organism or an infectious agent whose infection of cells of viable plant tissue elicits a disease response.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present disclosure are biologically active, that is they continue to possess the desired biological activity of the native protein, that is, modulating or regulatory activity as described herein. Such variants may result from, for example, genetic polymorphism or from human manipulation. Biologically active variants of a native R protein of the disclosure will have at least 40%, 50%, 60%, 70%, generally at least 75%, 80%, 85%, preferably about 90% to 95% or more, and more preferably about 98% or more sequence identity to the amino acid sequence for the native protein as determined by sequence alignment programs described elsewhere herein using default parameters. A biologically active variant of a protein of the disclosure may differ from that protein by as few as 1-15 amino acid residues, as few as 1-10, such as 6-10, as few as 5, as few as 4, 3, 2, or even 1 amino acid residue.

The proteins of the disclosure may be altered in various ways including amino acid substitutions, deletions, truncations, and insertions. Methods for such manipulations are generally known in the art. For example, amino acid sequence variants of the R proteins can be prepared by mutations in the DNA. Methods for mutagenesis and nucleotide sequence alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be preferable.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another, Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine I, Lysine (K), Histidine (H); Acidic: Aspartic acid (D), Glutamic acid (E), Asparagine (N), Glutamine (Q). See also, Creighton, 1984. In addition, individual substitutions, deletions or additions which alter, add or delete a single amino acid or a small percentage of amino acids in an encoded sequence are also "conservatively modified variations."

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development in animal and/or plant including banana species.

As used herein, the term "vector", "plasmid", or "construct" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, recombinant plant viruses. Non-limiting examples of plant viruses include, TMV-mediated (transient) transfection into tobacco (Tuipe, T-H et al (1993), J. Virology Meth, 42: 227-239), ssDNA genomes viruses (e.g., family Geminiviridae), reverse transcribing viruses (e.g., families Caulimoviridae, Pseudoviridae, and Metaviridae), dsNRA viruses (e.g., families Reoviridae and Partitiviridae), (−) ssRNA viruses (e.g., families Rhabdoviridae and Bunyaviridae), (+) ssRNA viruses (e.g., families Bromoviridae, Closteroviridae, Comoviridae, Luteoviridae, Potyviridae, Sequiviridae and Tombusviridae) and viroids (e.g., families Pospiviroldae and Avsunviroidae). Detailed classification information of plant viruses can be found in Fauquet et al (2008, "Geminivirus strain demarcation and nomenclature". Archives of Virology 153:783-821, incorporated herein by reference in its entirety), and Khan et al. (Plant viruses as molecular pathogens; Publisher Routledge, 2002, ISBN 1560228954, 9781560228950). Examples of non-viral vectors include, but are not limited to, liposomes, polyamine derivatives of DNA, and the like.

Also, "vector" is defined to include, inter alia, any plasmid, cosmid, phage or Agrobacterium binary vector in double or single stranded linear or circular form which may or may not be self-transmissible or mobilizable, and which can transform prokaryotic or eukaryotic host either by integration into the cellular genome or exist extrachromosomally (e.g. autonomous replicating plasmid with an origin of replication).

Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

As used herein, the term "resistant", or "resistance", describes a plant, line or cultivar that shows fewer or reduced symptoms to a biotic pest or pathogen than a susceptible (or more susceptible) plant, line or variety to that biotic pest or pathogen. These terms are variously applied to describe plants that show no symptoms as well as plants showing some symptoms but that are still able to produce marketable product with an acceptable yield. Some lines that are referred to as resistant are only so in the sense that they may still produce a crop, even though the plants may appear visually stunted and the yield is reduced compared to uninfected plants. As defined by the International Seed Federation (ISF), a non-governmental, non-profit organization representing the seed industry (see "Definition of the Terms Describing the Reaction of Plants to Pests or Pathogens and to Abiotic Stresses for the Vegetable Seed Industry", May 2005), the recognition of whether a plant is affected by or subject to a pest or pathogen can depend on the analytical method employed. Resistance is defined by the ISF as the ability of plant types to restrict the growth and development of a specified pest or pathogen and/or the damage they cause when compared to susceptible plant varieties under similar environmental conditions and pest or pathogen pressure. Resistant plant types may still exhibit some disease symptoms or damage. Two levels of resistance are defined. The term "high/standard resistance" is used for plant varieties that highly restrict the growth and development of the specified pest or pathogen under normal pest or pathogen pressure when compared to susceptible varieties. "Moderate/intermediate resistance" is applied to plant types that restrict the growth and development of the specified pest or pathogen, but exhibit a greater range of symptoms or damage compared to plant types with high resistance. Plant types with intermediate resistance will show less severe symptoms than susceptible plant varieties, when grown under similar field conditions and pathogen pressure. Methods of evaluating resistance are well known to one skilled in the art. Such evaluation may be performed by visual observation of a plant or a plant part (e.g., leaves, roots, flowers, fruits et. al) in determining the severity of symptoms. For example, when each plant is given a resistance score on a scale of 1 to 5 based on the severity of the reaction or symptoms, with 1 being the resistance score applied to the most resistant plants (e.g., no symptoms, or with the least symptoms), and 5 the score applied to the plants with the most severe symptoms, then a line is rated as being resistant when at least 75% of the plants have a resistance score at a 1, 2, or 3 level, while susceptible lines are those having more than 25% of the plants scoring at a 4 or 5 level. If a more detailed visual evaluation is possible, then one can use a scale from 1 to 10 so as to broaden out the range of scores and thereby hopefully provide a greater scoring spread among the plants being evaluated.

Another scoring system is a root inoculation test based on the development of the necrosis after inoculation and its position towards the cotyledon (such as one derived from Bosland et al., 1991), wherein 0 stands for no symptom after infection; 1 stands for a small necrosis at the hypocotyl after infection; 2 stands a necrosis under the cotyledons after infection; 3 stands for necrosis above the cotyledons after infection; 4 stands for a necrosis above the cotyledons together with a wilt of the plant after infection, while eventually, 5 stands for a dead plant.

In addition to such visual evaluations, disease evaluations can be performed by determining the pathogen bio-density in a plant or plant part using electron microscopy and/or through molecular biological methods, such as protein hybridization (e.g., ELISA, measuring pathogen protein density) and/or nucleic acid hybridization (e.g., RT-PCR, measuring pathogen RNA density). Depending on the particular pathogen/plant combination, a plant may be determined resistant to the pathogen, for example, if it has a pathogen RNA/DNA and/or protein density that is about 50%, or about 40%, or about 30%, or about 20%, or about 10%, or about 5%, or about 2%, or about 1%, or about 0.1%, or about 0.01%, or about 0.001%, or about 0.0001% of the RNA/DNA and/or protein density in a susceptible plant.

Methods used in breeding plants for disease resistance are similar to those used in breeding for other characters. It is necessary to know as much as possible about the nature of inheritance of the resistant characters in the host plant and the existence of physiological races or strains of the pathogen.

As used herein, the term "full resistance" is referred to as complete failure of the pathogen to develop after infection, and may either be the result of failure of the pathogen to enter the cell (no initial infection) or may be the result of failure of the pathogen to multiply in the cell and infect subsequent cells (no subliminal infection, no spread). The presence of full resistance may be determined by establishing the absence of pathogen protein or pathogen RNA in cells of the plant, as well as the absence of any disease symptoms in said plant, upon exposure of said plant to an infective dosage of pathogen (i.e. after 'infection'). Among breeders, this phenotype is often referred to as "immune". "Immunity" as used herein thus refers to a form of resistance characterized by absence of pathogen replication even when the pathogen is actively transferred into cells by e.g. electroporation.

As used herein, the term "partial resistance" is referred to as reduced multiplication of the pathogen in the cell, as reduced (systemic) movement of the pathogen, and/or as reduced symptom development after infection. The presence of partial resistance may be determined by establishing the systemic presence of low concentration of pathogen protein or pathogen RNA in the plant and the presence of decreased or delayed disease-symptoms in said plant upon exposure of said plant to an infective dosage of pathogen. Protein concentration may be determined by using a quantitative detection method (e.g. an ELISA method or a quantitative reverse transcriptase-polymerase chain reaction (RT-PCR)). Among breeders, this phenotype is often referred to as "intermediate resistant."

As used herein, the term "tolerant" is used herein to indicate a phenotype of a plant wherein disease-symptoms remain absent upon exposure of said plant to an infective dosage of pathogen, whereby the presence of a systemic or local pathogen infection, pathogen multiplication, at least the presence of pathogen genomic sequences in cells of said plant and/or genomic integration thereof can be established. Tolerant plants are therefore resistant for symptom expression but symptomless carriers of the pathogen. Sometimes, pathogen sequences may be present or even multiply in plants without causing disease symptoms. This phenomenon is also known as "latent infection". In latent infections, the pathogen may exist in a truly latent non-infectious occult form, possibly as an integrated genome or an episomal agent (so that pathogen protein cannot be found in the cytoplasm, while PCR protocols may indicate the present of pathogen nucleic acid sequences) or as an infectious and continuously replicating agent. A reactivated pathogen may spread and initiate an epidemic among susceptible contacts. The presence of a "latent infection" is indistinguishable from the presence of a "tolerant" phenotype in a plant.

As used herein, the term "susceptible" is used herein to refer to a plant having no or virtually no resistance to the pathogen resulting in entry of the pathogen into the plant and multiplication and systemic spread of the pathogen, resulting in disease symptoms. The term "susceptible" is therefore equivalent to "non-resistant".

As used herein, the term "offspring" refers to any plant resulting as progeny from a vegetative or sexual reproduction from one or more parent plants or descendants thereof. For instance an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

As used herein, the terms "dicotyledon," "dicot" and "dicotyledonous" refer to a flowering plant having an embryo containing two seed halves or cotyledons. Examples include tobacco; tomato; the legumes, including peas, alfalfa, clover and soybeans; oaks; maples; roses; mints; squashes; daisies; walnuts; cacti; violets and buttercups.

As used herein, the term "monocotyledon," "monocot" or "monocotyledonous" refer to any of a subclass (Monocotyledoneae) of flowering plants having an embryo containing only one seed leaf and usually having parallel-veined leaves, flower parts in multiples of three, and no secondary growth in stems and roots. Examples include banana, daffodils, sugarcane, ginger, lily, orchid, rice, corn, grasses, such as tall fescue, goat grass, and Kentucky bluegrass; grains, such as wheat, oats and barley, irises; onion and palm.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present disclosure relates to QTLs, i.e. genomic regions that may comprise one or more genes or regulatory sequences, it is in some instances more accurate to refer to "haplotype" (i.e. an allele of a chromosomal segment) instead of "allele", however, in those instances, the term "allele" should be understood to comprise the term "haplotype". Alleles are considered identical when they express a similar phenotype. Differences in sequence are possible but not important as long as they do not influence phenotype.

As used herein, the term "locus" (plural: "loci") refers to any site that has been defined genetically. A locus may be a gene, or part of a gene, or a DNA sequence that has some regulatory role, and may be occupied by different sequences.

As used herein, the term "molecular marker" or "genetic marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Mapping of molecular markers in the vicinity of an allele is a procedure which can be performed quite easily by the average person skilled in molecular-biological techniques which techniques are for instance described in Lefebvre and Chevre, 1995; Lorez and Wenzel, 2007, Srivastava and Narula, 2004, Meksem and Kahl, 2005, Phillips and Vasil, 2001. General information concerning AFLP technology can be found in Vos et al. (1995, AFLP: a new technique for DNA fingerprinting, Nucleic Acids Res. 1995 Nov. 11; 23(21): 4407-4414).

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the term "heterozygote" refers to a diploid or polyploid individual cell or plant having different alleles (forms of a given gene) present at least at one locus.

As used herein, the term "heterozygous" refers to the presence of different alleles (forms of a given gene) at a particular gene locus.

As used herein, the term "homozygote" refers to an individual cell or plant having the same alleles at one or more loci.

As used herein, the term "homozygous" refers to the presence of identical alleles at one or more loci in homologous chromosomal segments.

As used herein, the term "homologous" or "homolog" is known in the art and refers to related sequences that share a common ancestor or family member and are determined based on the degree of sequence identity. The terms "homology", "homologous", "substantially similar" and "corresponding substantially" are used interchangeably herein. Homologs usually control, mediate, or influence the same or similar biochemical pathways, yet particular homologs may give rise to differing phenotypes. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared.

The term "homolog" is sometimes used to apply to the relationship between genes separated by the event of speciation (see "ortholog") or to the relationship between genes separated by the event of genetic duplication (see "paralog").

The term "homeolog" refers to a homeologous gene or chromosome, resulting from polyploidy or chromosomal duplication events. This contrasts with the more common 'homolog', which is defined immediately above.

The term "ortholog" refers to genes in different species that evolved from a common ancestral gene by speciation. Normally, orthologs retain the same function in the course of evolution. Identification of orthologs is critical for reliable prediction of gene function in newly sequenced genomes.

The term "paralog" refers to genes related by duplication within a genome. While orthologs generally retain the same function in the course of evolution, paralogs can evolve new functions, even if these are related to the original one.

"Homologous sequences" or "homologs" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in *Current Protocols in Molecular Biology* (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Michigan), AlignX, and Vector NTI (Invitrogen, Carlsbad, CA).

As used herein, the term "hybrid" refers to any individual cell, tissue or plant resulting from a cross between parents that differ in one or more genes.

As used herein, the term "inbred" or "inbred line" refers to a relatively true-breeding strain.

The term "single allele converted plant" as used herein refers to those plants which are developed by a plant breeding technique called backcrossing wherein essentially all of the desired morphological and physiological characteristics of an inbred are recovered in addition to the single allele transferred into the inbred via the backcrossing technique.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (TO) plant regenerated from material of that line; (b) has a pedigree comprised of a TO plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

As used herein, the terms "introgression", "introgressed" and "introgressing" refer to the process whereby genes of one species, variety or cultivar are moved into the genome of another species, variety or cultivar, by crossing those species. The crossing may be natural or artificial. The process may optionally be completed by backcrossing to the recurrent parent, in which case introgression refers to infiltration of the genes of one species into the gene pool of another through repeated backcrossing of an interspecific hybrid with one of its parents. An introgression may also be described as a heterologous genetic material stably integrated in the genome of a recipient plant.

As used herein, the term "population" means a genetically homogeneous or heterogeneous collection of plants sharing a common genetic derivation.

As used herein, the term "variety" or "cultivar" means a group of similar plants that by structural features and performance can be identified from other varieties within the same species. The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

As used herein, the term "mass selection" refers to a form of selection in which individual plants are selected and the next generation propagated from the aggregate of their seeds. More details of mass selection are described herein in the specification.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein, the term "self-crossing", "self pollinated" or "self-pollination" means the pollen of one flower on one plant is applied (artificially or naturally) to the ovule (stigma) of the same or a different flower on the same plant.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T and G/C content) of primer. A pair of bi-directional primers consists of one forward and one reverse primer as commonly used in the art of DNA amplification such as in PCR amplification.

A probe comprises an identifiable, isolated nucleic acid that recognizes a target nucleic acid sequence. A probe includes a nucleic acid that is attached to an addressable location, a detectable label or other reporter molecule and that hybridizes to a target sequence. Typical labels include radioactive isotopes, enzyme substrates, co-factors, ligands, chemiluminescent or fluorescent agents, haptens, and enzymes. Methods for labelling and guidance in the choice of labels appropriate for various purposes are discussed, for example, in Sambrook et al. (ed.), *Molecular Cloning: A Laboratory Manual*, $2^{nd}$ ed., vol. 1-3, Cold Spring Harbor Laboratory Press, Cold Spring Harbor, NY, 1989 and Ausubel et al. *Short Protocols in Molecular Biology*, $4^{th}$ ed., John Wiley & Sons, Inc., 1999.

Methods for preparing and using nucleic acid probes and primers are described, for example, in Sambrook et al. (ed.), *Molecular Cloning: A Laboratory Manual*, $2^{nd}$ ed., vol. 1-3, Cold Spring Harbor Laboratory Press, Cold Spring Harbor, NY, 1989; Ausubel et al. *Short Protocols in Molecular Biology*, $4^{th}$ ed., John Wiley & Sons, Inc., 1999; and Innis et al. *PCR Protocols, A Guide to Methods and Applications*, Academic Press, Inc., San Diego, CA, 1990. Amplification primer pairs can be derived from a known sequence, for example, by using computer programs intended for that purpose such as PRIMER (Version 0.5, 1991, Whitehead Institute for Biomedical Research, Cambridge, MA). One of ordinary skill in the art will appreciate that the specificity of a particular probe or primer increases with its length. Thus, in order to obtain greater specificity, probes and primers can be selected that comprise at least 20, 25, 30, 35, 40, 45, 50 or more consecutive nucleotides of a target nucleotide sequences.

For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (2001) Molecular Cloning: A Laboratory Manual (3rd ed., Cold Spring Harbor Laboratory Press, Plainview, New York). See also Innis et al. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The present disclosure provides an isolated nucleic acid sequence comprising a sequence selected from the group consisting of FusR1, homologs of FusR1, orthologs of FusR1, paralogs of FusR1, and fragments and variations thereof. In one embodiment, the present disclosure provides an isolated polynucleotide encoding a protein produced by the nucleic acid sequence for FusR1, comprising a nucleic acid sequence that shares at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to FusR1.

Methods of alignment of sequences for comparison are well known in the art. Various programs and alignment algorithms are described in: Smith and Waterman (*Adv. Appl. Math.*, 2:482, 1981); Needleman and Wunsch (*J. Mol. Biol.*, 48:443, 1970); Pearson and Lipman (*Proc. Natl. Acad. Sci* 85:2444, 1988); Higgins and Sharp (*Gene*, 73:237-44, 1988); Higgins and Sharp (*CABIOS*, 5:151-53, 1989); Corpet et al. (*Nuc. Acids Res.*, 16:10881-90, 1988); Huang et al. (*Comp. Appls Biosci.*, 8:155-65, 1992); and Pearson et al. (*Meth. Mol. Biol.*, 24:307-31, 1994). Altschul et al. (*Nature Genet.*, 6:119-29, 1994) presents a detailed consideration of sequence alignment methods and homology calculations.

The present disclosure also provides a chimeric gene comprising the isolated nucleic acid sequence of any one of the polynucleotides described above operably linked to suitable regulatory sequences.

The present disclosure also provides a recombinant construct comprising the chimeric gene as described above. In one embodiment, said recombinant construct is a gene silencing construct, such as used in RNAi gene silencing. In another embodiment, said recombinant construct is a gene editing construct, such as used in CRISPR-Cas gene editing system.

The expression vectors of the present disclosure may include at least one selectable marker. Such markers include dihydrofolate reductase, G418 or neomycin resistance for eukaryotic cell culture and tetracycline, kanamycin or ampicillin resistance genes for culturing in *E. coli* and other bacteria.

The present disclosure also provides a transformed host cell comprising the chimeric gene as described above. In one embodiment, said host cell is selected from the group consisting of bacteria, yeasts, filamentous fungi, algae, animals, and plants including, but not limited to *Musa* genus.

These sequences allow the design of gene-specific primers and probes for FusR1, homologs of FusR1, orthologs of FusR1, homeologs of FusR1, paralogs of FusR1, and fragments and variations thereof.

II. Modulation of Disease Resistance

The present disclosure is drawn to polynucleotides and/or polypeptides of newly-identified FusR1 (*Fusarium* Resistant 1) and methods for modulating, stimulating or enhancing disease resistance in plants, caused by pathogens. Pathogens of the disclosure include, but are not limited to, bacteria, fungi, viruses or viroids, nematodes, insects, and the like.

Bacterial pathogens include but are not limited to *Pseudomonas avenae* subsp. *avenae, Xanthomonas campestris* pv. *holcicola, Enterobacter dissolvens, Envinia dissolvens, Ervinia carotovora* subsp. *carotovora, Envinia chrysanthemi* pv. *zeae, Pseudomonas andropogonis, Pseudomonas syringae* pv. *coronafaciens, Clavibacter michiganensis* subsp., *Corynebacterium michiganense* pv. *nebraskense, Pseudomonas syringae* pv. *syringae, Herniparasitic* bacteria (see under fungi), *Bacillus subtilis, Erwinia stewartii*, and *Spiroplasma kunkelii.*

Fungal pathogens include but are not limited to *Collelotrichum graminicola, Glomerella graminicola Politis, Glomerella lucumanensis, Aspergillus flavus, Rhizoctonia solani* Kuhn, *Thanatephorus cucumeris, Acremonium strictum* W. Gams, *Cephalosporium acremonium Auct. non Corda Black Lasiodiplodia theobromae=Bolr odiplodia y theobromas Borde blanco Marasmiellus* sp., *Physoderma maydis, Cephalosporium Corticium sasakii, Curvularia clavata, C. maculans, Cochhobolus eragrostidis, Curvularia inaequahs, C. intermedia* (teleomorph *Cochhobolus intermedius*), *Curvularia lunata* (teleomorph: *Cochliobolus lunatus*), *Curvularia pallescens* (teleomorph *Cochliobolus pallescens*), *Curvularia senegalensis, C. luberculata* (teleomorph: *Cochliobolus tuberculatus*), *Didymella exitalis Diplodiafiumenti* (teleomorph *Botryosphaeriafestucae*), *Diplodia maydis=Stenocarpella maydis, Stenocarpella macrospora=Diplodia macrospora, Sclerophthora rayssiae* var. *zeae, Sclerophthora macrospora=Sclerospora macrospora, Sclerospora graminicola, Peronosclerospora maydis=Sclerospora maydis, Peronosclerospora philippinensis, Sclerospora philippinensis, Peronosclerospora sorghi=Sclerospora sorghi, Peronosclerospora spontanea=Sclerospora spontanea, Peronosclerospora sacchari=Sclerospora sacchari, Nigrospora oryzae* (teleomorph: *Khuskia oryzae*) *A. Iternaria alternala=A. tenuis, Aspergillus glaucus, A. niger, Aspergillus* spp., *Botrytis cinerea, Cunninghamella* sp., *Curvulariapallescens, Doratomyces slemonitis=Cephalotrichum slemonitis, Fusarium culmorum, Gonatobotrys simplex, Pithomyces maydicus, Rhizopus microsporus Tiegh., R. stolonifer=R. nigricans, Scopulariopsis brumptii, Claviceps gigantea* (anamorph: *Sphacelia* sp) *Aureobasidium zeae=Kabatiella zeae, Fusarium subglutinans=F. moniliforme* var. *subglutinans, Fusarium moniliforme, Fusarium avenaceum* (teleomorph *Gibberella avenacea*), *Botryosphaeria zeae=Physalospora zeae* (anamorph: *Allacrophoma zeae*), *Cercospora sorghi=C. sorghi* var. *maydis, Helminthosporium pedicellatum* (teleomorph: *Selosphaeriapedicellata*), *Cladosporium cladosporioides=Hormodendrum cladosporioides, C. herbarum* (teleomorph *Mycosphaerella tassiana*), *Cephalosporium maydis, A. Iternaria alternata, A. scochyta maydis, A. tritici, A. zeicola, Bipolaris victoriae, Helminthosporium victoriae* (teleomorph *Cochhoholus victoriae*), *C. sativus* (anamorph: *Bipolaris sorokiniana=H. sorokinianum=H. sativum*), *Epicoccum nigrum, Exserohilum prolatum=Drechslera prolata* (teleomorph: *Setosphaeriaprolata*), *Graphium penicillioides, Leptosphaeria maydis, Leptothyrium zeae, Ophiosphaerella herpotricha* (anamorph *Scolecosporiella* sp.), *Pataphaeosphaeria michotii, Phoma* sp., *Septoria zeae, S. zeicola, S. zeina Setosphaeria turcica, Exserohilzim turcicum=Helminthosporium furcicum, Cochhoholus carbonum, Bipolaris zeicola=Helminthosporium carhonum, Penicilhum* spp., *P. chrysogenum, P. expansum, P. oxalicum, Phaeocytostroma ambiguum, Phaeocylosporella zeae, Phaeosphaeria maydis=Sphaerulina nmaydis, Botryosphaeriafestucae=Physalospora zeicola* (anamorph: *Diplodiaftumenfi*), *Herniparasitic* bacteria and fungi *Pyrenochaeta Phoma terrestris=Pyrenochaeta terrestris, Pythiumn* spp., *P. arrhenomanes, P. graminicola, Pythium aphanidermatum=P. hutleri L., Rhizoctonia zeae* (teleomorph: *Waitea circinata*), *Rhizoctonia solani, minor A Iternaria alternala, Cercospora sorghi, Dictochaetaftrtilis, Fusarium acuminatum* (teleomorph *Gihherella acuminata*), *E. equiseti* (teleomorph: *G. intricans*), *E. oxysporum, E. pallidoroseum, E. poae, E. roseum, G. cyanogena* (anamorph: *E. sulphureum*), *Microdochium holleyi, Mucor* sp., *Periconia circinata, Phytophthora cactorum, P. drechsleri, P. nicotianae* var. *parasitica, Phytophthora* spp., *Rhizopus arrhizus, Setosphaeria rostrata, Exserohilum rostratum=Helminthosporium rostratum, Puccinia sorghi, Physopella pallescens, P. zeae, Sclerotium* rofsii Sacc. (teleomorph *Athelia rotfsii*), *Bipolaris sorokiniana, B. zeicola=Helminthosporium carbonum, Diplodia maydis, Exserohilum pedicillatum, Exserohilum furcicum=Helminthosporium turcicum, Fusarium avenaceum, E. culmorum, E. moniliforme, Gibberella zeae* (anamorph *E. graminearum*), *Macrophominaphaseolina, Penicillium* spp., *Phomopsis* sp., *Pythium* spp., *Rhizoctonia solani, R. zeae, Sclerotium rolfsfi, Spicaria* sp., *Selenophoma* sp., *Gaeumannomyces graminis, Myrothecium gramineum, Monascus purpureus, M. ruber* Smut, *Ustilago zeae=U. maydis* Smut, *Ustilaginoidea virens* Smut, *Sphacelotheca reiliana=Sporisorium holci, Cochliobolus heterostrophus* (anamorph: *Bipolaris maydis=Helminthosporium maydis*), *Stenocarpella macrospora=Diplodia macrospora, Cercospora sorghi, Fusarium episphaeria, E. merismoides, F. oxysporum Schlechtend, Fusarium oxysporum* f. sp. *cubense* (Foc), *Fusarium* spp., *E. poae, E. roseum, E. solani* (teleomorph: *Nectria haematococca*), *F. tricincturn, Mariannaea elegans, Mucor* sp., *Rhopographus zeae, Spicaria* sp., *Aspergillus* spp., *Penicillium* spp., *Trichoderma viride=T. lignorum* teleomorph: *Hypocrea* sp., *Stenocarpella maydis=Diplodia zeae, Ascochyta ischaemi, Phyllosticta maydis* (teleomorph: *Mycosphaerella zeae-maydis*), *Mycosphaerella fijiensis, Pseudocercospora* (*Paracercospora*) *fijiensi* and *Gloeocercospora sorghi.*

Virus or viroids include but are not limited to American wheat striate mosaic virus mosaic (AWSMV), barley stripe mosaic virus (BSMV), barley yellow dwarf virus (BYDV), banana bunchy top virus, Brome mosaic virus (BMV), cereal chlorotic mottle virus (CCMV), corn chlorotic vein banding virus (CCVBV), maize chlorotic mottle virus (MCMV), maize dwarf mosaic virus (MDMV), A or B, wheat streak mosaic virus (WSMV), cucumber mosaic virus (CMV), cynodon chlorotic streak virus (CCSV), Johnsongrass mosaic virus (JGMV), maize bushy stunt or mycoplasma-like organism (NILO), maize chlorotic dwarf virus (MCDV), maize chlorotic mottle virus (MCMV), maize dwarf mosaic virus (MDMV) strains A, D, E and F, maize leaf fleck virus (MLFV), maize line virus (NELV), maize mosaic virus (MMV), maize mottle and chlorotic stunt virus, maize pellucid ringspot virus (MPRV), maize raya gruesa virus (MRGV), maize rayado fino virus (MRFV), maize red leaf and red stripe virus (MRSV), maize ring mottle virus (MRMV), maize rio cuarto virus (MRCV), maize rough dwarf virus (MRDV), maize sterile stunt virus (strains of barley yellow striate virus), maize streak virus (MSV), maize chlorotic stripe, maize hoja Maize stripe virus blanca, maize stunting virus, maize tassel abortion virus (MTAV), maize vein enation virus (MVEV), maize wallaby ear virus (MAVEV), maize white leaf virus, maize white line mosaic virus (NTVVLMV), millet red leaf virus (NMV), viruses of the family Nanoviridae, Northern cereal mosaic virus (NCMV), oat pseudorosette virus, oat sterile dwarf virus (OSDV), rice black-streaked dwarf virus (RBSDV), rice stripe virus (RSV), sorghum mosaic virus (SrMV), formerly sugarcane mosaic virus (SCMV) stains H, I and M, sugarcane Fiji disease virus (FDV), sugarcane mosaic virus (SCMV) strains *A, B*, D, E, SC, BC, Sabi and NM vein enation virus, and wheat spot mosaic virus (WSMV).

Parasitic nematodes include but are not limited to Awl *Dolichodorus* spp., *D. heterocephalus* Bulb and stem (Europe), *Ditylenchus dipsaci* Burrowing *Radopholus similis* Cyst *Heterodera avenae, H. zeae, Punctodera chalcoensis* Dagger *Xiphinema* spp., *X. americanum, X. mediterraneum* False root-knot *Nacobbus dorsalis* Lance, Columbia *Hoplolaimus columbus* Lance *Hoplolaimus* spp., *H. galeatus* Lesion *Pratylenchus* spp., *P. brachyurus, P. crenalus, P. hexincisus, P. neglectus, P. penetrans, P. scribneri, P. thornei, P. zeae* Needle *Longidorus* spp., *L. breviannulatus* Ring *Criconemella* spp., *Cornata* Root-knot *Meloidogyne* spp., *M. chitwoodi, M. incognita, M. javanica* Spiral *Helicotylenchus* spp., *Belonolaimus* spp., *B. longicaudatus* Stubby-root *Paratrichodorus* spp., *P. christiei, P. minor, Ouinisulcius aculus*, and *Trichodorus* spp.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera.

In some embodiments, the plant pathogen is selected from fungi, especially soil borne fungi such as *Fusarium oxysporum*, water and air-borne viruses such as *Mycosphaerella fijiensis* (Morelet), *Mycosphaerella musicola* (Leach ex Mulder), *Pseudocercospora (Paracercospora) fijiensi, Verticillium dahliae, Cladosporium* and *Ralstona Solanaceum*.

In some embodiments, said disease is Fusarium wilt, also known as Panama disease, which is a lethal fungal disease caused by the soil-borne fungus *Fusarium oxysporum* f. sp. *cubense* (Foc). Said disease can also be known as Panama Disease TR4, Foc, Panama Disease Tropical Race 4, or TR4. In some embodiments, resistance to TR4 is combined within a single cultivar with genetic resistances or tolerances to one or more additional diseases, such as resistance to diseases caused by bacteria, other fungi, viruses, nematodes, insects and the like.

Fusarium wilt is one of the most destructive and notorious diseases of banana. It is also known as Panama disease, in recognition of the extensive damage it caused in export plantations in this Central American country. By 1960, Fusarium wilt had destroyed an estimated 40,000 ha of 'Gros Michel' (AAA), causing the export industry to convert to cultivars in the Cavendish subgroup (AAA) (Ploetz and Pegg, 2000). Fusarium wilt is caused by the soil-borne hyphomycete, *Fusarium oxysporum* Schlect. f sp. *cubense*. It is one of more than 120 formae speciales (special forms) of *F. oxysporum* that cause vascular wilts of flowering plants. This pathogen affects species of *Musa* and *Heliconia*, and strains have been classified into four physiological races based on pathogenicity to host cultivars in the field (race 1, 'Gros Michel'; race 2, 'Bluggoe'; race 3, *Heliconia* spp.; and race 4, Cavendish cultivars and all cultivars susceptible to race 1 and 2). Four *Fusarium oxysporum* races have been named, Race 1 through Race 4. Race 1 is a critical pathogen of many banana cultivars. Race 2 attacks cooking bananas. Race 3 affects banana relatives in the Americas, but doesn't seem to affect bananas. The current threat stems from the expansion of *Fusarium oxysporum* race 4, also known as TR4 (Tropical Race 4), which is designated as 'Foc-TR4'. Race 4 has two subgroups, TR4 and SR4 (subtropical race 4). Until recently, race 4 had only been recorded to cause serious losses in the subtropical regions of Australia, South Africa, the Canary Islands, and Taiwan. Banana growers and banana companies have repeatedly stated that if this race were to become established in the Americas, the world export industries would be severely affected, as there is no widely accepted replacement for Cavendish cultivars (Bentley et al., 1998).

Very recently, (Stokstad, 2019), Panama Disease Race 4 (Fusarium wilt) has now been detected in the Western Hemisphere. The disease was found in four plantations in Columbia. These four plantations were immediately quarantined. However, a substantial part of the banana market consists of exports from Central and South America to the United States. This market is now critically imperiled, making a swift solution to the crisis even more urgent. The recent emergence of Panama Disease TR4 in the Western Hemisphere makes a swift solution to the crisis even more urgent.

In some embodiments, 'Fusarium Wilt" or 'FW' can be used interchangeably, which designates the disease as displayed in infected banana plants.

In the 1950s and 1960s, a single variety, Gros Michel, was grown widely. It was highly sensitive to the easily spread fungus *Fusarium oxysporum* f sp. *cubense*. In particular, it was Fusarium Tropical Race 1 (Foc-TR1) which caused a fatal wilt disease, and the global banana industry was nearly destroyed. The Cavendish variety was found to be highly resistant to Foc-TR1, and replaced Gros Michel for global banana production. In the 1990s, growers began to find banana plants infected with Foc-TR4, a newly emerging race. Foc-TR4 is also easily spread and has been found in banana plantations in Asia, the Middle East, and Africa, again threatening the global banana crop. Great concern has been provoked by the recent identification of Foc-TR4 in the Caribbean, which means that the fungus now has a beachhead in the Western Hemisphere, thus threatening Latin America banana production. In some embodiments, the present disclosure provide a solution to serious problems on bananas caused by Foc-TR4. In some embodiments, the solution is drawn to identification of disease-resistant genetic materials and/or architecture and importation of said genetic materials and architecture to banana varieties that are susceptible to pathogenic fungi (e.g. Foc-TR4).

Bananas are also susceptible to other pathogenic fungi, particularly *Mycosphaerella fijiensis* (Morelet) which causes black leaf streak disease (also known as Black Sigatoka and Black Sig) and *M. musicola*, which causes Yellow Sigatoka leaf spot disease. It is known that these fungi (*M. fijiensis* and *M. musicola*) are controlled with fungicides, but fungicides are ineffective against Foc-TR4.

The present disclosure teaches method of modulating, stimulating, or enhancing disease resistance in plants, caused by pathogens such as Foc-TR4 using next generation plant breeding techniques, also known as new breeding techniques.

New breeding techniques (NBTs) refer to various new technologies developed and/or used to create new characteristics in plants through genetic variation, the aim being targeted mutagenesis, targeted introduction of new genes or gene silencing (RdDM). The following breeding techniques are within the scope of NBTs: targeted sequence changes facilitated through the use of Zinc finger nuclease (ZFN) technology (ZFN-1, ZFN-2 and ZFN-3, see U.S. Pat. No. 9,145,565, incorporated by reference in its entirety), Oligonucleotide directed mutagenesis (ODM, a.k.a., site-directed mutagenesis), Cisgenesis and intragenesis, epigenetic approaches such as RNA-dependent DNA methylation (RdDM, which does not necessarily change nucleotide sequence but can change the biological activity of the sequence), Grafting (on GM rootstock), Reverse breeding, Agro-infiltration for transient gene expression (agro-infiltration "sensu stricto", agro-inoculation, floral dip), Transcription Activator-Like Effector Nucleases (TALEN5, see U.S. Pat. Nos. 8,586,363 and 9,181,535, incorporated by reference in their entireties), the CRISPR/Cas system (see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, which are all hereby incorporated by reference), engineered meganuclease, re-engineered homing endonucleases, DNA guided genome editing (Gao et al., Nature Biotechnology (2016), doi: 10.1038/nbt.3547, incorporated by reference in its entirety), and Synthetic genomics. A major part of today's targeted genome editing, another designation for New Breeding Techniques, is the applications to induce a DNA double strand break (DSB) at a selected location in the genome where the modification is intended. Directed repair of the DSB allows for targeted genome editing. Such applications can be utilized to generate mutations (e.g., targeted mutations or precise native gene editing) as well as precise insertion of genes (e.g., cisgenes, intragenes, or transgenes). The applications leading to mutations are often identified as site-directed nuclease (SDN) technology, such as SDN1, SDN2 and SDN3. For SDN1, the outcome is a targeted, non-specific genetic deletion mutation: the position of the DNA DSB is precisely selected, but the DNA repair by the host cell is random and results in small nucleotide deletions, additions or substitutions. For SDN2, a SDN is used to generate a targeted DSB and a DNA repair template (a short DNA sequence identical to the targeted DSB DNA sequence except for one or a few nucleotide changes) is used to repair the DSB: this results in a targeted and predetermined point mutation in the desired gene of interest. As to the SDN3, the SDN is used along with a DNA repair template that contains new DNA sequence (e.g. gene). The outcome of the technology would be the integration of that DNA sequence into the plant genome. The most likely application illustrating the use of SDN3 would be the insertion of cisgenic, intragenic, or transgenic expression cassettes at a selected genome location. *A* complete description of each of these techniques can be found in the report made by the Joint Research Center (JRC) Institute for Prospective Technological Studies of the European Commission in 2011 and titled "New plant breeding techniques—State-of-the-art and prospects for commercial development", which is incorporated by reference in its entirety.

In some embodiments, various approaches have been taken to prevent or treat Foc-TR4 infection. The present disclosure teaches that a key approach to prevent or treat Foc-TR4 is to (1) find resistant banana cultivars, (2) to identify resistance genes and/or traits from the selected banana cultivars, and (3) breed/introduce the resistance genes and/or traits into sensitive banana cultivars.

Zuo et al. (2018) evaluated 129 banana accessions and found 10 that are highly resistant to Foc-TR4—thus providing naturally existing resistant cultivars for study.

Li et al. (2012) looked at the transcriptomes and expression profiles of roots of a resistant mutant and compared these to sensitive wild type Brazilian Cavendish bananas at two time points after challenge with Foc-TR4. They found some 88,000 unigenes, with 5,000 related to defense pathways in other plants. They concluded that some 2,600 genes were differentially expressed in the resistant mutant, including some plant cell lignification genes that were expressed at the same or lower levels in the resistant mutant.

In similar fashion, Bai et al. (2013) compared root transcriptomes from the Foc-TR4 sensitive Brazilian cultivar to the Yueyoukangl cultivar that is known to have far lower disease severity. Bai et al. found differential expression for 500 to 2000 different unigenes at different time points, and these could be clustered into 11 different types of metabolic pathways. Bai et al. found genes connected to cell wall lignification that were differentially regulated between the sensitive and resistant cultivars—specifically 4-coumarate: CoA ligase (4CL), glutathione S-transferase (GST), cellulose synthase, Caffeoyl-CoA O-methyltransferase (CCoAM), and cinnamylalcohol dehydrogenase (CAD) were expressed at higher levels in the resistant cultivar and concluded that cell wall lignification could be one of the mechanisms involved in Foc-TR4 resistance. Bai et al. pointed out that this was inconsistent with the result found in Li et al. (2012) and concluded that different plants could have different resistance mechanisms and that more work is required to decipher how banana cultivars are able to resist Foc-TR4.

Wang et al. (2017) also looked at differential root gene expression at the time of flower bud differentiation and found 107 genes differentially expressed in the roots between a susceptible banana cultivar and a sensitive one.

Zhang et al. (2018) showed that Foc-TR4 infection proceeds similarly in the roots of a resistant cultivar (Pahang) and a susceptible cultivar (Brazilian) until reaching the corm, where the fungal biomass and degree of necrosis were significantly less in the Pahang vs. Brazilian. (The banana 'corm' is an underground stem, or rhizome, from which the roots grow.)

Van der Berg et al. (2007) used quantitative RT-PCR to identify genes that are were up-regulated in the FW-tolerant GCTCV-218 banana cultivar after infection with Foc-4. Their control was the FW-sensitive Williams cultivar. They found that a number of genes were up-regulated in FW-tolerant GCTCV-218 as compared to FW-sensitive Williams. As expected, many of the up-regulated genes were homologous to known defense-associated genes, including cell wall-strengthening genes. They reported 13 genes that were up-regulated in roots. While they state that "The results shed light on genes involved in defence and provide a step towards understanding Fusarium wilt of banana and thereby developing an effective disease management strategy", the paper does not suggest that any one of 13 that they deposited in GenBank can be used for controlling Fusarium Wilt. No particular strategy is given for use of these genes to control Fusarium Wilt.

Vishnevetsky et al. (2009) (U.S. Pat. No. 7,534,930) described a method to genetically engineer banana plants to confer exogenous disease resistance traits, including resistance to Black and Yellow *Sigatoka* and *Botrytis cinerea*. Vishnevetsky et al. manipulated three polynucleotides into banana plants, including genes encoding endochitinase, stilbene synthase, and superoxide dismutase.

Paul et al (2011) isolated a gene from the nematode *C. elegans* that, when stably transformed into the 'Lady finger' banana cultivar, appeared in greenhouse trials to confer resistance to Race 1 of Panama Disease.

Although transformation of bananas with a gene derived from a nematode is unlikely to be accepted by consumers, follow-up work by Dale's group with a gene derived from bananas does show promise for achieving *Fusarium* resistance in GMO-transformed bananas. For example, Peraza-Echeverria et al (2009) isolated a resistance gene analog (RGA2) gene from a wild banana, *Musa acuminata malaccensis*. This gene is a member of the large NB-LRR-type resistance gene family. When transformed into FW-sensitive Cavendish plants (Dale et al, 2017), the gene appears to confer resistance to *Fusarium*. Dale et al (2017) conducted field trials of transgenic banana plants for 3 years. At the trial's conclusion, some 67% to 100% of FW-sensitive control plants were dead or infected. However, in four lines of bananas transfected with their candidate gene, fewer than 30% of the transformed bananas showed signs of severe infection (i.e., >70% showed some tolerance or resistance). One line transformed with RGA2 appeared to be immune to TR4. While this is good evidence that the gene may confer some FW-resistance, the gene was first isolated over a decade ago and it is unclear whether the banana growing industry will ever embrace the RGA2 gene.

It is important to note that it is believed (unpublished communications with banana industry breeders and scientists) that there may be up to four genes in the *Musa* genome that contribute some degree of *Fusarium* resistance so RGA2 alone is unlikely to solve the present crisis, even if it is accepted by growers. Even if RGA2 finds acceptance, that the industry has a dire need for multiple genes to control TR4.

Inventor notes that FusR1 of the present disclosure is completely unrelated to RGA2. The two genes have completely different nucleotide sequences (i.e., they have no sequence identity), they lie on different chromosomes, they have different biochemistries, and they have different mechanisms of action in the plant.

Wu et al. (2016) sequenced a disease-resistant wild banana relative, *Musa itinerans*, found in subtropical China. Ks values were calculated in order to estimate speciation and paleoploidization events in the *Musa* genus. Also Ka/Ks values were calculated to show that as expected, most genes in the *Musa itinerans* genome have undergone purifying selection. It was suggested that *M. itinerans* is known to be disease resistant, thus, its genome could be mined for disease resistance genes.

In some embodiments, the present disclosure provides methods of finding, identifying, and selecting genes resistant to diseases, such as Fusarium wilt from FW-resistant banana cultivars. In other embodiments, the present disclosure provides nucleotide and polypeptide sequences of *Fusarium*-resistant genes (e.g. FusR1 gene) identified from the methods of the present disclosure. In further embodiments, the present disclosure teaches methods of generating and/or producing banana varieties having resistance genes and/or traits by using next generation plant breeding technology, which include but are not limited to CRISPR technology described in the present disclosure.

III. Identification of FusR1 Gene from *Musa* Genus

Cultivated bananas are generally triploid (although a few are diploid) as a result of their complex evolutionary and domestication history which involved a number of interspecific and intraspecific hybridization events, both natural and human-driven. Edible, cultivated bananas are largely the result of hybridization between two wild diploid species, *Musa acuminata* and *Musa balbisiana* (Christelová et al., 2017). Human domestication of bananas began about 7,000 years ago in Southeast Asia (D'Hont et al, 2012). Banana genomes derived from *M. acuminata* are known as "A" genomes, while bananas derived from *M. balbisiana* have "B" genomes (D'Hont et al., 2012). Thus the genome structure of the diploid *M. acuminata* is labeled AA, and the genomic structure of diploid *M. balbisiana* is BB. Edible banana cultivars may thus have triploid AAA genomes (like Cavendish or Gros Michel), AAB genomes (as in many plantains), or ABB genomes (like the Cachaco landrace). *M. acuminata* likely arose in Malaysia or Indonesia (Christelova et al., 2017). In contrast, *M. balbisiana* is believed to have originated in India, Thailand or the Philippines (Christelova et al., 2017). Thus, these two species were originally allopatric and geographic isolation provided an opportunity for each species to develop unique traits. When humans later moved *M. acuminata* cultivars to areas populated by *M. balbisiana*, interspecific hybridization took place.

The economically critical Cavendish cultivar, which accounts for at least 99% of commercial banana export production, exhibits triploid induced sterility. This, combined with parthenocarpy, gives rise to edible fruit without seeds, but severely hampers breeding, so Cavendish bananas are propagated vegetatively (clonally). The Cavendish genotype has three *M. acuminata*-derived "A" genomes.

In some embodiments, inventor identified genes that effectively control Fusarium Wilt in banana. For example, the present disclosure teaches that a gene, which is named FusR1 (*Fusarium* Resistance 1) was identified by using inventor's molecular evolutionary analysis approach. The resent disclosure teaches that the FusR1 gene is a native gene in *Musa* species, including cultivated bananas, *M. itinerans, M. acuminata, M. balbisiana, M. basjoo*, as well as *Musella lasiocarpa*, the sole member of a closely related genus. The ortholog (two alleles) from the wild banana relative, *Musa itinerans*, is given here as SEQ ID NO: 1 and SEQ ID NO: 4. The *M. itinerans* FusR1 sequences were obtained from multiple accessions (including, but not limited to, ITC1526, ITC1571, and PT-BA-00223). All *M. itinerans* accessions are extremely FW-resistant (Li et al., 2015; Wu et al., 2016).

The present disclosure teaches that inventor identified two alleles of FusR1 in *M. itinerans*. SEQ ID NO: 1 gives allele #1 of the FusR1 mRNA sequence. SEQ ID NO: 2 gives the allele #1 coding sequence. SEQ ID NO: 4 gives allele #2 of the FusR1 mRNA sequence. SEQ ID NO: 5 gives the allele #2 coding sequence. Alleles 1 and 2 are very similar in sequence: they code for just four amino acid differences.

A second transcript of FusR1 was identified (SEQ ID NO: 7) from *M. itinerans*; this transcript has an expressed (i.e., unspliced) intron that results in disruption of the proper reading frame. This is expressed at very low levels.

*M. itinerans* is naturally extremely resistant to the effects of Fusarium Wilt (Li et al., 2015; Wu et al., 2016). In some embodiments, the FusR1 gene from *M. itinerans* is responsible for resistance to Fusarium Wilt.

The present disclosure further teaches that inventor identified three alleles of FusR1 in *M. acuminata*. Two of these alleles were isolated from FW-resistant accessions of *M. acuminata*. The third allele was isolated from an FW-sensitive *M. acuminata* accession. The *M. acuminata* FusR1 FW-resistant sequences were obtained from multiple FW-resistant accessions, including ITC0896 (*M. a.* subspecies *banksii*) and PT BA-00281 (Pisang Bangkahulu). The *M. acuminata* FW-sensitive sequence is from the FW-sensitive accessions ITC0507, ITC0685, PT-BA-00304, PT-BA-00310, and PT-BA-00315.

SEQ ID NO: 8 gives the mRNA sequence of allele 1 of the FW-resistant FusR1 gene from *M. acuminata*. SEQ ID NO: 10 gives the mRNA sequence of allele 2 of the FW-resistant FusR1 gene from *M. acuminata*. The coding sequence of FW-resistant allele 1 from *M. acuminata* is given in SEQ ID 9. SEQ ID NO: 11 gives the coding sequence of FW-resistant allele 2 from *M. acuminata*.

SEQ ID NO: 13 gives the mRNA sequence of the FW-sensitive FusR1 allele from *M. acuminata*. (The *M. acuminata* FW-sensitive sequence was identified from accessions ITC0507, ITC0685, PT-BA-00304, PT-BA-00310, and PT-BA-00315. These accessions include multiple samples from banana cultivars such as Pisang Madu, Pisang Pipit, and Pisang Rojo Uter, all of which have been well-characterized as FW-sensitive (Chen et al, 2019).

Inventor identified a putative core promoter for FusR1 from *M. acuminata*. Inventor used two different promoter prediction applications in an attempt to find congruent predictions from different algorithms/software.

As a first step, inventor amplified and sequenced a 753 bp sequence fragment (SEQ ID NO: 31), which begins upstream of the coding region of the FW-resistant-allele of the FusR1 gene derived from *M. acuminata*. This fragment is 100% identical to bp7868911-bp7869210 and bp7869341-bp7869743 of GenBank accession NC 025206 (*Musa acuminata* subsp. *malaccensis* chromosome 5, ASM31385v2, whole genome shotgun sequence), which lies on *M. acuminata* Chromosome 5.

Inventor first analyzed the upstream region of FusR1 using the "Neural Network Promoter Prediction" (NNPP), which is available on the Berkeley *Drosophila* Genome Project (BDGP). BDGP is a consortium of the *Drosophila* Genome Center, funded by the National Human Genome Research Institute, the National Cancer Institute, and the Howard Hughes Medical Institute. The NNPP software was 'trained' on human and *Drosophila melanogaster* promoter sequences, but has proven to be generally effective at identifying promoter sequences, even in plants (Reese, 2001).

NNPP analysis successfully identified a core promoter for FusR1. Analysis results follow. The first 189 bases of SEQ ID NO: 31 (shown in lower case) are non-coding upstream sequence, including the 5' UTR sequence of FusR1; the next 423 bases are coding sequence (shown in UPPER CASE). This coding sequence is identical to SEQ ID NO: 9. The last 141 bases are 3' UTR (shown in lower case). Bases 92-141 of SEQ ID NO: 31 (atcgtggcactataaataggacaagaggagggatgaggtaaaacgcactc) are the NNPP predicted promoter sequence, shown in lower case bold. The transcription start site (TSS) at base pair 132 is shown in lower case underlined bold. NNPP assigns a score of 0.88 (i.e., 88% confidence level) to this promoter.

SEQ ID NO: 31:
gtagagacacttgagttgaattctgaatccattatttcttctcatgaa cgcatacgtcccaccatacacaccaaatcttaatggctcaagcatcgt ggcac tataaataggacaagaggagggatgaggtaaaacgcactccct catacttgcacaggtacgttgtgatagaaagttcagaggtaagcgATG

GCTGGAGGAGGCAAAAGAGGTGAAGCGTCGTCTCTTCTACTTGTGACG

CTGCTCGTGACGTTGTTGGCTTTCTTCGCCACCAACTCCTCGGCAGCC

CGTGTCACACCCCGTCCGCAATCCCTCGCCAGAGCGGCACTGAGTGCG

GTGGGGGCAAGGCAAGATGAGCCGTGCTGCAGATGCGCGTGTCCTCTC

ATTTACCCACCTACTTGGTGCATTTGCGGCGGCATATGGCAAGGCTCC

TGCCCTTCCGCCTGCAACAACTGCCAGTGTGTCCTCAACGAGTGCACT

TGCCTCGATCTTATGGACCCCAAGGTCTGCGAGGCCAACTCCTGTCCC

TGGCCTGTTGCAGCCCCCAAAGTAGAGCCGGCGCAGCAGTGGGCTATC

GAAGAAACCGGTGGGAAATTAGCGATGATGGTGTGAtccaattgtgtt tgtgatcgcctgtcgtcttctctcgctccgtcctatccatctatccat ccatctacttataatctatgtcgtgtaccgtcgtgtggtgttgctttg cttcagtaataaaaataaaatgcttctgcttttt Inventor then analyzed the upstream region of FusR1 from *M. acuminata* using the "Prediction of PLANT Promoters" (TSSP) software, which is targeted specifically at identification of plant promoter sequences (Solovyev and Shahmuradov, 2003). This is a part of a suite of sequence analysis software produced by Softberry, Inc. TSSP identified the transcription start site (TSS) as position 132 in SEQ ID NO: 31, which is identical to the NNPP software results (see above). TSSP located the FusR1 TATA box (shown above in lower case italics) at bases 102-107 of SEQ ID NO: 31. Thus the FusR1 TATA box lies, as expected, 25 base pairs upstream of the TSS.

As these 2 different promoter prediction applications give congruent results, inventor identified the correct promoter sequence for *M. acuminata*.

The present disclosure teaches methods of introducing the newly-identified FusR1 gene and its variants into cultivated bananas, particularly the *Fusarium*-sensitive Cavendish cultivar in order to make these cultivars resistant to Fusarium Wilt. In some embodiments, the present disclosure teaches that traditional plant breeding methods can be used to introduce FusR1 gene/trait from *M. itinerans* into Cavendish and other cultivated bananas. In other embodiments, the present disclosure teaches that next generation plant breeding methods can be used to introduce FusR1 gene/trait from *M. itinerans* into Cavendish and other cultivated bananas. In further embodiments, the present disclosure teaches methods of introducing FusR1 gene/trait from *M. itinerans* into Cavendish and other cultivated bananas using genome editing techniques such as targeted genome editing system using zinc finger nucleases (ZFN), transcription activator like effector nucleases (TALEN) or CRISPR/Cas9 system technology exploiting the endonuclease activity of CRISPR-associated (Cas) proteins with sequence specificity directed by CRISPR RNAs (crRNAs).

Given the threat of likely extinction for Cavendish, the present disclosure provides a rapid, efficient, and precise genome editing approach using CRISPR/Cas9 system adapted for production of minimally genetically-edited bananas having *Fusarium*-resistant gene/trait, which will be accepted especially in developing countries where banana provides critical economic and food security. The present disclosure teaches that the transfer of the native FusR1 gene from *M. itinerans* to cultivated bananas can be best accomplished with CRISPR technology, which allows a targeted, clean, and efficient transfer and which, as compared to more traditional genetic editing techniques, minimizes potential side effects.

In some embodiments, useful alleles of FusR1 (SEQ ID NO: 8 and SEQ ID NO: 10) are identified from naturally FW-resistant *M. acuminata* populations. These alleles confer FW-resistance. The present disclosure teaches that the FusR1 allele derived from *M. acuminata* can be used, in combination with FusR1 alleles derived from *M. itinerans* (SEQ ID NO: 2 and SEQ ID NO: 5), to enhance FW-resistance in cultivated bananas, particularly Cavendish.

The present disclosure teaches gene stacking with at least two FusR1 genes identified by inventor disclosed in the present disclosure.

Both the *M. itinerans* FusR1 ortholog (SEQ ID NO: 2 and SEQ ID NO: 5) and the *M. acuminata* FW-resistant alleles (SEQ ID NO: 8 and SEQ ID NO: 10) can be used in traditional plant breeding and/or new generation plant breeding approaches. The new generation plant breeding approaches include but are not limited to marker-assisted-selection (MAS) and/or genome editing techniques in cultivated bananas.

Some *M. balbisiana* accessions have been rigorously characterized as very resistant to FW, while others are extremely FW-sensitive. While it might be expected that the wild *M. balbisiana* accessions would be resistant to a pathogen like *Fusarium*, it has been difficult for researchers to understand why closely related accessions differ so significantly in terms of FW resistance.

Inventor discovered a structural difference of the nucleotide sequences of FusR1 gene in FW-sensitive *M. balbisiana* accessions as shown in FIG. 5. All the FW-sensitive *M. balbisiana* accessions inventor analyzed contain a 'broken' FusR1 transcript. This analysis is restricted to the 'broken' FusR1 genes found in all FW-sensitive accessions that were examined. FusR1 mRNAs in all *M. balbisiana* accessions inventor examined had an unspliced, expressed intron that disrupts proper reading frame. In addition, inventor found (i) a long 82 or 84 bp deletion in several FusR1 mRNAs (2) in all accessions, a smaller 1 bp deletion, or (ii), in some accessions, a 4 bp insertion, each of which also disrupts the open reading frame, thus coding for a mutated, non-functional FUSR1 protein. All FW-sensitive *M. balbisiana* accessions have one or more of these reading frame disrupters described above, resulting in a non-functional protein. In some embodiments, the present disclosure teaches that some *M. balbisiana* accessions have all four reading frame disrupters. See FIG. 5.

In other embodiments, inventor also discovered another significant difference when studying FW-resistant vs. FW-sensitive *M. acuminata* accessions. In some embodiments, FusR1 in *M. acuminata* give resistance vs. sensitivity depending on FusR1 alleles. The present disclosure teaches that two alleles, which turned out to be "resistant alleles" confer FW-resistance; SEQ ID NO: 8 and SEQ ID NO: 10. These two alleles are very similar in sequence to the FusR1 ortholog derived from the FW-resistant wild banana spaces, *M. basjoo* (SEQ ID NO: 17 and SEQ ID NO: 20. The third allele, the FW-sensitive allele, is found only in FW-sensitive *M. acuminata* accessions (SEQ ID NO: 13).

The *M. balbisiana* FusR1 sequence (SEQ ID NO: 26 and SEQ ID NO: 27) does not confer FW resistance, because this gene is damaged (as it is in all the FW-sensitive *M. balbisiana* accessions examined) by reading-frame disrupting indels and/or expressed unspliced introns that cause loss of FW resistance.

In further embodiments, FusR1 sequences derived from FW-resistant *M. acuminata* accessions (SEQ ID NO: 8 and SEQ ID NO: 10) have a very high sequence similarity to the FusR1 ortholog derived from *M. basjoo* (SEQ ID ID: 17). *M. basjoo* is a wild banana species that is very resistant to FW (Li et al., 2015). In other embodiments, the FusR1 sequence (SEQ ID NO: 13) from FW-sensitive *M. acuminata* accessions differs from the FW-resistant *M. acuminata* alleles (SEQ ID NO: 8 and SEQ ID NO: 10).

The present disclosure teaches that FW-resistance in *M. acuminata* depends upon having the allele found only in FW-resistant accessions. Although *M. acuminata* and *M. balbisiana* are more closely related to each other than either is to *M. itinerans* or *M. basjoo*, the FusR1 sequences that control FW-resistance cluster together in direct contrast to the way the species are actually related. In other embodiments, the FusR1 gene has adapted (i.e., been positively selected) so that FusR1 fails to reflect the actual relationships within *Musa* species. The present disclosure teaches two independent adaptive events (convergent evolution) or perhaps the FW-resistant FusR1 version has been traded between various *Musa* species (gene transfer).

Inventor confirmed the true phylogenetic relationships between these *Musa* species by sequencing two different, conserved, single-copy genes, C2H2 and TOPO6, from several *Musa* species. C2H2-type zinc finger proteins play important roles in plant development and growth as well as abiotic stress resistance, including for fruit ripening in banana (Han et al., Front. Plant Sci., Vol. 11, Article 115: 1-13, 20 Feb. 2020; Han et al., Postharvest Biology and Technology, 116:8-15, June 2016). TOPO6, a nuclear gene-marker region of subunit B of the plant homolog of archaean topoisomerase VI, occurs as single-copy lochs in the haploid genome of most plant groups (Frank R. Blattner, Plant Systematics and Evolution, Vol. 302: 239-244, 2016). These two genes (whose biochemical functions are well-known) have no role in pathogen control, making them ideal as 'controls' for understanding the adaptive changes imposed on banana FusR1 as a result of exposure to *Fusarium*. Thus, the disclosure teaches that the consensus in the literature that *M. acuminata* and *M. balbisiana* are sister species is correct, meaning that significant changes have occurred to our newly-identified gene, FusR1, in these banana species, providing yet more evidence that FusR1 confers FW-resistance. See the phylogenetic trees provided in FIGS. 3 and 4.

The present disclosure teaches the critical sequence differences between the strongly FW-resistant FusR1 alleles from *M. itinerans*, which allows the inventor to determine the exact few nucleotides that make FusR1 capable of controlling FW. Based on the inventor's findings, the present disclosure teaches a method of using CRISPR/Cas system to confer FW-resistance in FW-sensitive Cavendish (as well as all other cultivated bananas), by precisely changing only a few critical nucleotides in FusR1. Also, the present disclosure also teaches a method of using these critical nucleotides to create a novel FusR1 sequence with greater FW-resistance than the native gene.

IV. FusR1 Gene and Variants Thereof

The present disclosure is predicated, in part, on the isolation of novel FusR1 gene from banana varieties and species. The nucleotide sequences of this FusR1 gene and its orthologs sequences are presented in SEQ ID NO: 1-2, 4-5, 7-11, 13-14, 16-18, 20-21, 23-24, and 26-31 respectively.

In some embodiments, SEQ ID NO: 1 is partial mRNA sequence for allele 1 of FusR1 from *Musa itinerans*, the most Fusarium-resistant wild banana species. SEQ ID NO: 4 is partial mRNA sequence for allele 2 of FusR1 from *Musa itinerans*.

The aforementioned FusR1 alleles from *M. itinerans* (SEQ ID NO: 1 and SEQ ID NO: 4) code for slightly different proteins, which are SEQ ID NO: 3 and SEQ ID NO: 6, respectively. The translated polypeptide of SEQ ID NO: 1 is presented as SEQ ID NO: 3. The translated polypeptide of SEQ ID NO: 4 is presented as SEQ ID NO: 6. These are only slightly different, with the few differing amino acid residues all being biochemically conservative. In some embodiments, 5 different *M. itinerans* accessions were sequenced and all accessions had these same two FusR1 alleles.

In some embodiments, SEQ ID NO: 8 and SEQ ID NO: 10 are partial mRNAs (including the full coding sequences). These are the FW-resistant alleles of FusR1 from *Musa acuminata* ssp. *banksia* (Accession No. ITC0896) and PT BA-00281 (Pisang Bankahulu). These two alleles differ at a single silent site. In other embodiments, SEQ ID NO: 13 represents the FW-sensitive allele from *M. acuminata*. In further embodiments, SEQ ID NO: 9 and SEQ ID NO: 11 represent the coding sequence for the FW-resistant alleles from *M. acuminata*. Also, SEQ ID NO: 12 represents the FW-resistant protein sequence from *M. acuminata*, which is a translated polypeptide sequence of SEQ ID NO: 8 and SEQ ID NO: 10.

In some embodiments, SEQ ID NO: 17 and SEQ ID NO: 20 are partial mRNA FusR1 allele sequences from *M. basjoo*, a wild banana species that is resistant to *Fusarium*. In other embodiments, SEQ ID NO: 23 is the FusR1 sequence from another wild banana relative, *Musella lasiocarpa*.

It is noted that all of the mRNA sequences inventor reports herein are technically partial, as they lack a bit of 5'UTR and usually a few bases of the extreme end of the 3'UTR. The vast majority of the mRNAs reported herein are very close to being full sequence.

In some embodiments, SEQ ID NO: 26, and SEQ ID NO: 28-30 are the partial mRNA FusR1 sequences from several different *M. balbisiana* accessions. SEQ ID NO: 27 is the FusR1 coding sequence from *M. balbisiana*. In some embodiments, a large number of FW-sensitive *M. balbisiana* accessions were examined. In all the FusR1 sequences from FW-sensitive *M. balbisiana* accessions, the structure of the FusR1 sequence is broken and/or damaged. All the FW-sensitive *M. balbisiana* accessions had a FusR1 coding sequence with a 1 bp deletion at position 340 in the coding sequence. All FW-sensitive *M. balbisiana* accessions also had a long unspliced, expressed intron in the coding sequence. Several also had a long (82-84 bp) deletion, some had another 4 bp deletion, and in all cases, a one base pair deletion (relative to FusR1 from other plant species, including all other banana accessions While it is true that 84 bp, as a multiple of three, doesn't disrupt the reading frame, it does remove 28 amino acid residues from the protein's primary structure, thus potentially disrupting the folded protein's tertiary structure and thus negatively impacting function. In any case, based on our findings, the ubiquitous 1 bp deletion always results in reading frame disruption.

Inventor included mRNA sequences from *Musa balbisiana* accessions from which inventor sequenced FusR1. These illustrate the various ways in which FusR1 is 'broken' in *M. balbisiana*. Inventor notes herein that EVERY *M. balbisiana* accession inventor analyzed has a broken FusR1 mRNA transcript. FIG. 5 shows these *M. balbisiana* FusR1 sequences aligned.

*M. balbisiana* accession ITC1016 (SEQ ID NO: 26) contains an 82 base pair unspliced, expressed intron. This intron disrupts the reading frame, resulting in a premature termination codon located 8 bp into the intron, which causes a truncated 141 bp coding sequence (as opposed to the proper 423 bp coding sequence). In addition, this accession (and, in fact, all *M. balbisiana* accessions) also has a one base pair deletion, located about 90 bp 5'-ward of the true termination codon, which (even if the intron had been properly spliced out) results in a premature stop codon, giving a truncated coding sequence.

*M. balbisiana* accession ITC0545 (SEQ ID NO: 28) contains the same 82 base pair unspliced, expressed intron. This intron disrupts the reading frame, resulting in a premature stop codon located 8 bp into the intron, causing a truncated 141 bp coding sequence (as opposed to the proper 423 bp coding sequence). Another 27 bp downstream of the expressed intron lies an 85 bp deletion. While this in combination with the 84 bp expressed intron would mathematically restore the correct reading frame, (85 bp−82 bp=3 bp), as explained above, it causes the loss of 28 amino acid residues that lie in a functionally critical region of the folded FusR1 protein. In addition, this accession also has the one base pair deletion, located about 90 bp 5'-ward of the true termination codon, which (even if the intron had been properly spliced out) results in a premature stop codon, giving a truncated coding sequence. Finally, the FusR1 mRNA from this accession also has a frame-disrupting 4 bp insertion farther downstream.

*M. balbisiana* accession ITC0080 (SEQ ID NO: 29) contains the same unspliced, expressed intron as the previous accessions, except that this version of the unspliced intron is 84 bp in length. While this expressed intron doesn't disrupt reading frame, it does introduce 28 extra amino acid residues that lie in a functionally critical region of the folded protein and thus very likely prevents proper folding of the FusR1 protein. In addition, this accession also has the one base pair deletion, located about 90 bp 5'-ward of the true termination codon, which (even if the intron had been properly spliced out) results in a premature stop codon, giving a truncated coding sequence.

*M. balbisiana* accession ITC1527 (SEQ ID NO: 30) contains the same unspliced, expressed intron as the previous accessions, this time 82 bp long. Again, this intron disrupts the reading frame, resulting in a premature stop codon located 8 bp into the intron, causing a truncated 141 bp coding sequence (as opposed to the proper 423 bp coding sequence). In addition, the FusR1 mRNA from this accession has a 4 bp insertion farther downstream. In addition, this accession also has the one base pair deletion, located about 90 bp 5'-ward of the true termination codon, which (even if the intron had been properly spliced out) results in a premature stop codon, giving a truncated coding sequence.

All *M. balbisiana* accessions inventor analyzed have some combination of one or more of these various flaws in their FusR1 mRNA.

Table 1 summarizes sequence information of the present disclosure.

TABLE 1

Summary of Sequence Information

| SEQ ID NO. | Sequence Type | Origin | Brief Description |
| --- | --- | --- | --- |
| SEQ ID NO: 1 | Nucleotide | *Musa itinerans* | Partial mRNA sequence for the FW*-resistant FusR1 transcript 1, allele 1 from *Musa itinerans* |
| SEQ ID NO: 2 | Nucleotide | *Musa itinerans* | FusR1 allele 1 FW-resistant coding sequence from *M. itinerans* |
| SEQ ID NO: 3 | Protein | *Musa itinerans* | Protein sequence of FUSR1 FW-resistant allele 1 from *M. itinerans* |
| SEQ ID NO: 4 | Nucleotide | *Musa itinerans* | Partial mRNA sequence for FusR1 transcript 1 FW-resistant allele 2 from *Musa itinerans* |
| SEQ ID NO: 5 | Nucleotide | *Musa itinerans* | FusR1 FW-resistant allele 2 coding sequence from *M. itinerans* |
| SEQ ID NO: 6 | Protein | *Musa itinerans* | Protein sequence of FUSR1 FW-resistant allele 2 from *M. itinerans* |
| SEQ ID NO: 7 | Nulceotide | *Musa itinerans* | Partial mRNA sequence for FusR1 transcript 2 from *Musa itinerans* |
| SEQ ID NO: 8 | Nucleotide | *Musa acuminata* ssp. *banksii* | Partial mRNA sequence for FW-resistant FusR1 allele 1 from *M. acuminata* |
| SEQ ID NO: 9 | Nucleotide | *Musa acuminata* ssp. *banksii* | Coding sequence of FW-resistant FusR1 allele 1 from *M. acuminata* |
| SEQ ID NO: 10 | Nucleotide | *Musa acuminata* ssp. *banksii* | Partial mRNA sequence for FW-resistant FusR1 allele 2 from *M. acuminata* |
| SEQ ID NO: 11 | Nucleotide | *Musa acuminata* ssp. *banksii* | Coding sequence of FW-resistant FusR1 allele 2 from *M. acuminata* |
| SEQ ID NO: 12 | Protein | *Musa acuminata* ssp. *banksii* | Protein sequence of FW-resistant FUSR1 from *M. acuminata* |
| SEQ ID NO: 13 | Nucleotide | *Musa acuminata* | Partial mRNA sequence for FW-sensitive FusR1 allele from *M. acuminata* |
| SEQ ID NO: 14 | Nucleotide | *Musa acuminata* | Coding sequence of FW-sensitive FusR1 allele from *M. acuminata* |
| SEQ ID NO: 15 | Protein | *Musa acuminata* | Protein sequence of FW-sensitive FusR1 from *M. acuminata* |
| SEQ ID NO: 16 | Nucleotide | *Musa acuminata* | Partial mRNA sequence of FW-sensitive FusR1 transcript 2 from *M. acuminata* |
| SEQ ID NO: 17 | Nulceotide | *Musa basjoo* | Partial mRNA sequence of FusR1 FW-resistant allele 1 from *M. basjoo* |
| SEQ ID NO: 18 | Nucleotide | *Musa basjoo* | Coding sequence of FusR1 FW-resistant allele 1 from *M. basjoo* |
| SEQ ID NO: 19 | Protein | *Musa basjoo* | Protein sequence of FusR1 FW-resistant allele 1 from *Musa basjoo* |
| SEQ ID NO: 20 | Nucleotide | *Musa basjoo* | Partial mRNA sequence of FW-resistant allele 2 of FusR1 from *M. basjoo* |
| SEQ ID NO: 21 | Nucleotide | *M. basjoo* | Partial coding sequence of FusR1 FW-resistant allele 2 from *M. basjoo* |
| SEQ ID NO: 22 | Protein | *M. basjoo* | Partial protein sequence of FW-resistant allele 2 of FusR1 from *M. basjoo* |
| SEQ ID NO: 23 | Nucleotide | *Musella lasiocarpa* | Partial mRNA sequence of FusR1 from *Musella lasiocarpa* |
| SEQ ID NO: 24 | Nucleotide | *Musella lasiocarpa* | Coding sequence of FusR1 from *M. lasiocarpa* |
| SEQ ID NO: 25 | Protein | *Musella lasiocarpa* | Protein sequence of FUSR1 from *M. lasiocarpa* |
| SEQ ID NO: 26 | Nucleotide | *M. balbisiana* | Partial mRNA sequence of FusR1 from *M. balbisiana* Accession ITC1016 |
| SEQ ID NO: 27 | Nucleotide | *M. balbisiana* | "Hypothetical" coding sequence from *M. balbisiana* Accession ITC1016 |
| SEQ ID NO: 28 | Nucleotide | *M. balbisiana* | Partial mRNA sequence of FusR1 from *M. balbisiana* Accession ITC0545 |
| SEQ ID NO: 29 | Nucleotide | *M. balbisiana* | Partial mRNA sequence of FusR1 from *M. balbisiana* Accession ITC0080 |
| SEQ ID NO: 30 | Nucleotide | *M. balbisiana* | Partial mRNA sequence of FusR1 from *M. balbisiana* Accession ITC1527 |

TABLE 1-continued

Summary of Sequence Information

| SEQ ID NO. | Sequence Type | Origin | Brief Description |
|---|---|---|---|
| SEQ ID NO: 31 | Nucleotide | M. acuminata ssp. banskii | Upstream Sequence, including promoter sequence, of the FW-resistant allele 1 of FusR1 from M. acuminata |
| SEQ ID NO: 32 | Protein | M. balbisiana | Protein sequence of FUSR1 from M. balbisiana |

*FW—Fusarium wilt

In accordance with the present disclosure, the novel FusR1 gene and its orthologs will be useful for facilitating the construction of crop plants that are resistant to pathogenic disease, especially disease caused by fungal pathogens, viruses, nematodes, insects and the like. The FusR1 genes of the present disclosure can also be used as markers in genetic mapping as well as in assessing disease resistance in a plant of interest. Thus, the sequences can be used in breeding programs. See, for example, Gentzbittel et al. (1998, Theor. Appl. Genet. 96:519-523). Additional uses for the sequences of the disclosure include using the sequences as bait to isolate other signaling components on defense/resistance pathways and to isolate the corresponding promoter sequences. The sequences may also be used to modulate plant development processes, such as pollen development, regulation of organ shape, differentiation of aleurone and shoot epidermis, embryogenic competence, and cell/cell interactions. See, generally, Sambrook et al. (1989) Molecular Cloning: A Laboratory Manual (2nd ed., Cold Spring Harbor Laboratory Press, Plainview, N.Y.). The sequences of the present disclosure can also be used to generate variants (e.g., by 'domain swapping') for the generation of new resistance specificities.

The disclosure encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified polynucleotide or polypeptide is substantially free of other cellular material or culture medium when produced by recombinant techniques, or substantially free of chemical precursors or other chemicals when chemically synthesized. Suitably, an "isolated" polynucleotide is free of sequences (especially protein encoding sequences) that naturally flank the polynucleotide (i.e., sequences located at the 5' and 3' ends of the polynucleotide) in the genomic DNA of the organism from which the polynucleotide was derived. For example, in various embodiments, the isolated polynucleotide can contain less than about 5 kb, 4 kb, 3 kb, 2 kb, 1 kb, 0.5 kb, or 0.1 kb of nucleotide sequences that naturally flank the polynucleotide in genomic DNA of the cell from which the polynucleotide was derived. A polypeptide that is substantially free of cellular material includes preparations of protein having less than about 30%, 20%, 10%, 5%, (by dry weight) of contaminating protein. When the protein of the disclosure or biologically active portion thereof is recombinantly produced, culture medium suitably represents less than about 30%, 20%, 10%, or 5% (by dry weight) of chemical precursors or non-protein-of-interest chemicals.

A portion of a FusR1 nucleotide sequence that encodes a biologically active portion of a FusR1 polypeptide of the disclosure will encode at least about 5, 6, 7, 8, 9, 10, 11, 12, 13, 14, 15, 16, 17, 18, 19, 20, 21, 22, 23, 24, 25, 30, 40, 50, 60, 70, 80, 90, 100, 120, 150, 300, 400, 500, 600, 700, 800, 900 or 1000 contiguous amino acid residues, or almost up to the total number of amino acids present in a full-length FUSR1 polypeptide of the disclosure (for example, 140 amino acid residues for SEQ ID NO: 3, 6, 12, 19, or 22, respectively). Portions of a FusR1 nucleotide sequence that are useful as hybridization probes or PCR primers generally need not encode a biologically active portion of a FUSR1 polypeptide.

Thus, a portion of a FusR1 nucleotide sequence may encode a biologically active portion of a FUSR1 polypeptide, or it may be a fragment that can be used as a hybridization probe or PCR primer using standard methods known in the art. A biologically active portion of a FUSR1 polypeptide can be prepared by isolating a portion of one of the FusR1 nucleotide sequences of the disclosure, expressing the encoded portion of the FUSR1 polypeptide (e.g., by recombinant expression in vitro), and assessing the activity of the encoded portion of the FUSR1 polypeptide. Nucleic acid molecules that are portions of an FusR1 nucleotide sequence comprise at least about 15, 16, 17, 18, 19, 20, 25, 30, 50, 75, 100, 150, 200, 250, 300, 350, 400, 450, 500, 550, 600, or 650 nucleotides, or almost up to the number of nucleotides present in a full-length FusR1 nucleotide sequence disclosed herein (for example, about from 350 to 650 nucleotides for SEQ ID NO: 1-2, 4-5, 8-10, 17-18, or 20-21, respectively).

The disclosure also contemplates variants of the disclosed nucleotide sequences. Nucleic acid variants can be naturally occurring, such as allelic variants (same locus), homologues (different locus), and orthologues (different organism) or can be non-naturally occurring. Naturally occurring variants such as these can be identified with the use of well-known molecular biology techniques, as, for example, with polymerase chain reaction (PCR) and hybridization techniques as known in the art. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product). For nucleotide sequences, conservative variants include those sequences that, because of the degeneracy of the genetic code, encode the amino acid sequence of one of the FUSR1 polypeptides of the disclosure. Variant nucleotide sequences also include synthetically derived nucleotide sequences, such as those generated, for example, by using site-directed mutagenesis but which still encode a FUSR1 polypeptide of the disclosure. Generally, variants of a particular nucleotide sequence of the disclosure will have at least about 30%, 40% 50%, 55%, 60%, 65%, 70%, generally at least about 75%, 80%, 85%, desirably about 90% to 95% or more, and more suitably about 98% or more sequence identity to that particular nucleotide sequence as determined by sequence alignment programs described elsewhere herein using default parameters.

Variant nucleotide sequences also encompass sequences derived from a mutagenic or recombinant procedures such as 'DNA shuffling' which can be used for swapping domains in a polypeptide of interest with domains of other polypeptides. With DNA shuffling, one or more different FusR1 coding sequences can be manipulated to create a new FusR1 sequence possessing desired properties. In this procedure, libraries of recombinant polynucleotides are generated from a population of related polynucleotides comprising sequence regions that have substantial sequence identity and can be homologously recombined in vitro or in vivo. For example, using this approach, sequence motifs encoding a domain of interest may be shuffled between the FusR1 gene of the disclosure and other known FusR1 genes to obtain a new gene coding for a protein with an improved property of interest, such broadening spectrum of disease resistance. Strategies for DNA shuffling are known in the art. See, for example: Stemmer (1994, Proc. Natl. Acad. Sci. USA 91:10747-10751; 1994, Nature 370:389-391); Crameri et al. (1997, Nature Biotech. 15:436-438); Moore et al. (1997, J. Mol. Biol. 272:336-347); Zlang et al. (1997 Proc. Natl. Acad. Sci. USA 94:450-44509); Crameri et al. (1998, Nature 391:288-291); and U.S. Pat. Nos. 5,605,793 and 5,837,458.

The present disclosure provides nucleotide sequences comprising at least a portion of the isolated proteins encoded by nucleotide sequences for FusR1, homologs of FusR1, orthologs of FusR1, paralogs of FusR1, and fragments and variations thereof.

In some embodiments, the present disclosure provides a nucleotide sequence encoding FUSR1, and/or functional fragments and variations thereof comprising a nucleotide sequence that shares at least about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, about 99.1%, about 99.2%, about 99.3%, about 99.4%, about 99.5%, about 99.6%, about 99.7%, about 99.8%, or about 99.9% sequence identity to SEQ ID NO: 1, SEQ ID NO: 2, SEQ ID NO: 4, SEQ ID NO: 5, SEQ ID NO: 8, SEQ ID NO: 9, SEQ ID NO: 10, SEQ ID NO: 11, SEQ ID NO: 17, or SEQ ID NO: 18. In some embodiments, a nucleotide sequence encoding FUSR1 has the nucleic acid sequence of SEQ ID NO: 1, SEQ ID NO: 2, SEQ ID NO: 4, SEQ ID NO: 5, SEQ ID NO: 8, SEQ ID NO: 9, SEQ ID NO: 10, SEQ ID NO: 11, SEQ ID NO: 17, or SEQ ID NO: 18.

In some embodiments, the present disclosure provides nucleotide sequences for FusR1, homologs of FusR1, orthologs of FusR1, paralogs of FusR1, and fragments and variations thereof comprising nucleotide sequences that share at least about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, about 99.1%, about 99.2%, about 99.3%, about 99.4%, about 99.5%, about 99.6%, about 99.7%, about 99.8%, or about 99.9% sequence identity to SEQ ID NO: 1, SEQ ID NO: 2, SEQ ID NO: 4, SEQ ID NO: 5, SEQ ID NO: 8, SEQ ID NO: 9, SEQ ID NO: 10, SEQ ID NO: 11, SEQ ID NO: 17, or SEQ ID NO: 18. In some embodiments, nucleotide sequences for FusR1, homologs of FusR1, orthologs of FusR1, paralogs of FusR1, and fragments and variations thereof have the nucleic acid sequences of SEQ ID NO: 1, SEQ ID NO: 2, SEQ ID NO: 4, SEQ ID NO: 5, SEQ ID NO: 8, SEQ ID NO: 9, SEQ ID NO: 10, SEQ ID NO: 11, SEQ ID NO: 17, or SEQ ID NO: 18.

In some embodiments, nucleotide sequences for FusR1, homologs of FusR1, orthologs of FusR1, paralogs of FusR1, and fragments and variations thereof can be used to be expressed in plants. In some embodiments, said nucleotide sequences can be used to be incorporated into an expression cassette, which is capable of directing expression of a nucleotide sequence for FusR1, homologs of FusR1, orthologs of FusR1, paralogs of FusR1, and fragments and variations thereof in a plant cell, for example, banana varieties disclosed herein. This expression cassette comprises a promoter operably linked to the nucleotide sequence of interest (i.e. FusR1, orthologs of FusR1, and fragments and variations thereof) which is operably linked to termination signals. It also typically comprises sequences required for proper translation of the nucleotide sequence. The coding region usually codes for a protein of interest, (i.e. FUSR1). In some embodiments, the expression cassette comprising the nucleotide sequence for FusR1, homologs of FusR1, orthologs of FusR1, paralogs of FusR1, and fragments and variations thereof is chimeric so that at least one of its components is heterologous with respect to at least one of its other components.

In other embodiments, the expression cassette is one which is naturally occurring but has been obtained in a recombinant form useful for heterologous expression. The expression of the nucleotide sequence in the expression cassette can be under the control of a constitutive promoter or of an inducible promoter which initiates transcription only when the host cell is exposed to some particular external stimulus. Also, the expression of the nucleotide sequence in the expression cassette can be under the control of a tissue-specific promoter. In the case of a multicellular organism, the promoter can also be specific to a particular tissue or organ or stage of development in animal and/or plant including banana species.

The present disclosure provides polypeptides and amino acid sequences comprising at least a portion of the proteins encoded by nucleotide sequences for FusR1, homologs of FusR1, orthologs of FusR1, paralogs of FusR1, and fragments and variations thereof.

The present disclosure also provides an amino acid sequence encoded by the nucleic acid sequences of FusR1, homologs of FusR1, orthologs of FusR1, paralogs of FusR1, and/or fragments and variations thereof. In some embodiments, the present disclosure provides an isolated polypeptide comprising an amino acid sequence that shares at least about 70%, about 75%, about 80%, about 85%, at least about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to an amino acid sequence encoded by the nucleic acid sequences of FusR1, homologs of FusR1, orthologs of FusR1, paralogs of FusR1, and/or fragments and variations thereof. In one embodiment, the present disclosure provides an isolated polypeptide comprising an amino acid sequence which encodes an amino acid sequence that shares at least about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to an amino acid sequence encoded by the nucleic acid sequences of FusR1, homologs of FusR1, orthologs of FusR1, paralogs of FusR1, and/or fragments and variations thereof.

The disclosure also encompasses variants and fragments of proteins of an amino acid sequence encoded by the nucleic acid sequences of FusR1, homologs of FusR1, orthologs of FusR1 and/or paralogs of FusR1. The variants may contain alterations in the amino acid sequences of the constituent proteins. The term "variant" with respect to a polypeptide refers to an amino acid sequence that is altered by one or more amino acids with respect to a reference sequence. The variant can have "conservative" changes, or "nonconservative" changes, e.g., analogous minor variations can also include amino acid deletions or insertions, or both.

Functional fragments and variants of a polypeptide include those fragments and variants that maintain one or more functions of the parent polypeptide. It is recognized that the gene or cDNA encoding a polypeptide can be considerably mutated without materially altering one or more of the polypeptide's functions. First, the genetic code is well-known to be degenerate, and thus different codons encode the same amino acids. Second, even where an amino acid substitution is introduced, the mutation can be conservative and have no material impact on the essential function(s) of a protein. See, e.g., Stryer Biochemistry 3rd Ed., 1988. Third, part of a polypeptide chain can be deleted without impairing or eliminating all of its functions. Fourth, insertions or additions can be made in the polypeptide chain for example, adding epitope tags, without impairing or eliminating its functions (Ausubel et al. J. Immunol. 159(5): 2502-12, 1997). Other modifications that can be made without materially impairing one or more functions of a polypeptide can include, for example, in vivo or in vitro chemical and biochemical modifications or the incorporation of unusual amino acids. Such modifications include, but are not limited to, for example, acetylation, carboxylation, phosphorylation, glycosylation, ubiquination, labelling, e.g., with radionucleotides, and various enzymatic modifications, as will be readily appreciated by those well skilled in the art. A variety of methods for labelling polypeptides, and labels useful for such purposes, are well known in the art, and include radioactive isotopes such as 32P, ligands which bind to or are bound by labelled specific binding partners (e.g., antibodies), fluorophores, chemiluminescent agents, enzymes, and anti-ligands. Functional fragments and variants can be of varying length. For example, some fragments have at least 10, 25, 50, 75, 100, 200, or even more amino acid residues. These mutations can be natural or purposely changed. In some embodiments, mutations containing alterations that produce silent substitutions, additions, or deletions, but do not alter the properties or activities of the proteins or how the proteins are made are an embodiment of the disclosure.

Conservative amino acid substitutions are those substitutions that, when made, least interfere with the properties of the original protein, that is, the structure and especially the function of the protein is conserved and not significantly changed by such substitutions. Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain. Further information about conservative substitutions can be found, for instance, in Ben Bassat et al. (J. Bacteriol., 169:751 757, 1987), O'Regan et al. (Gene, 77:237 251, 1989), Sahin Toth et al. (Protein Sci., 3:240 247, 1994), Hochuli et al. (Bio/Technology, 6:1321 1325, 1988) and in widely used textbooks of genetics and molecular biology. The Blosum matrices are commonly used for determining the relatedness of polypeptide sequences. The Blosum matrices were created using a large database of trusted alignments (the BLOCKS database), in which pairwise sequence alignments related by less than some threshold percentage identity were counted (Henikoff et al., Proc. Natl. Acad. Sci. USA, 89:10915-10919, 1992). A threshold of 90% identity was used for the highly conserved target frequencies of the BLOSUM90 matrix. A threshold of 65% identity was used for the BLOSUM65 matrix. Scores of zero and above in the Blosum matrices are considered "conservative substitutions" at the percentage identity selected. The following table 2 shows exemplary conservative amino acid substitutions.

TABLE 2

Exemplary conservative amino acid substitutions listed

| Original Residue | Very Highly-Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

In some examples, variants can have no more than 3, 5, 10, 15, 20, 25, 30, 40, 50, or 100 conservative amino acid changes (such as very highly conserved or highly conserved amino acid substitutions). In other examples, one or several hydrophobic residues (such as Leu, Ile, Val, Met, Phe, or Trp) in a variant sequence can be replaced with a different hydrophobic residue (such as Leu, Ile, Val, Met, Phe, or Trp) to create a variant functionally similar to the disclosed an amino acid sequences encoded by the nucleic acid sequences of FusR1, homologs of FusR1, orthologs of FusR1 and/or paralogs of FusR1, and/or fragments and variations thereof.

In some embodiments, variants may differ from the disclosed sequences by alteration of the coding region to fit the codon usage bias of the particular organism into which the molecule is to be introduced. In other embodiments, the coding region may be altered by taking advantage of the degeneracy of the genetic code to alter the coding sequence such that, while the nucleotide sequence is substantially altered, it nevertheless encodes a protein having an amino acid sequence substantially similar to the disclosed an amino acid sequences encoded by the nucleic acid sequences of FusR1, homologs of FusR1, orthologs of FusR1 and/or paralogs of FusR1, and/or fragments and variations thereof.

In some embodiments, functional fragments derived from the FusR1 orthologs of the present disclosure are provided. The functional fragments can still confer resistance to pathogens when expressed in a plant. In some embodiments, the functional fragments contain at least the conserved region or Bowman-Birk inhibitor domain of a wild type FusR1 orthologs, or functional variants thereof. In some embodiments, the functional fragments contain one or more conserved region shared by two or more FusR1 orthologs, shared by two or more FusR1 orthologs in the same plant genus, shared by two or more dicot FUSR1 orthologs, and/or shared by two or more monocot FusR1 orthologs. The conserved regions or Bowman-Birk inhibitor domains can be determined by any suitable computer program, such as NCBI protein BLAST program and NCBI Alignment program, or equivalent programs. In some embodiments, the functional fragments are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids shorter compared to the FusR1 orthologs of the present disclosure. In some embodiments, the functional fragments are made by deleting one or more amino acid of the FusR1 orthologs of the present disclosure. In some embodiments, the functional fragments share at least 80%, 85%, 90%, 95%, 96%, 97%, 98%, 99%, or more identity to the FusR1 orthologs of the present disclosure.

In some embodiments, functional chimeric or synthetic polypeptides derived from the FusR1 orthologs of the present disclosure are provided. The functional chimeric or synthetic polypeptides can still confer resistance to pathogens when expressed in a plant. In some embodiments, the functional chimeric or synthetic polypeptides contain at least the conserved region or Bowman-Birk inhibitor domain of a wild type FUSR1 orthologs, or functional variants thereof. In some embodiments, the functional chimeric or synthetic polypeptides contain one or more conserved region shared by two or more FUSR1 orthologs, shared by two or more FusR1 orthologs in the same plant genus, shared by two or more monocot FusR1 orthologs, and/or shared by two or more dicot FUSR1 orthologs. Non-limiting exemplary conserved regions are shown in FIG. 2. The conserved regions or Bowman-Birk inhibitor domains can be determined by any suitable computer program, such as NCBI protein BLAST program and NCBI Alignment program, or equivalent programs. In some embodiments, the functional chimeric or synthetic polypeptides share at least 80%, 85%, 90%, 95%, 96%, 97%, 98%, 99%, or more identity to the FusR1 orthologs of the present disclosure.

Sequences of conserved regions unique to FW-sensitive alleles can also be used to knock-down the level of one or more FusR1 orthologs. In some embodiments, sequences of conserved regions can be used to make gene silencing molecules to target one or more FusR1 orthologs. In some embodiments, the gene silencing molecules are selected from the group consisting of double-stranded polynucleotides, single-stranded polynucleotides or Mixed Duplex Oligonucleotides. In some embodiments, the gene silencing molecules comprises a DNA/RNA fragment of about 10 bp, 15 bp, 19 bp, 20 bp, 21 bp, 25 bp, 30 bp, 40 bp, 50 bp, 60 bp, 70 bp, 80 bp, 90 bp, 100 bp, 150 bp, 200 pb, 250 bp, 300 bp, 350 bp, 400 bp, 500 bp, 600 bp, 700 bp, 800 bp, 900 bp, 1000 bp, or more polynucleotides, wherein the DNA/RNA fragment share at least 90%, 95%, 99%, or more identity to a conserved region of the FusR1 orthologs sequences of the present disclosure, or complementary sequences thereof.

V. Plant Transformation

The present polynucleotides coding for FUSR1, homologs of FusR1, orthologs of FusR1 and/or paralogs of FusR1, and/or fragments and variations thereof of the present disclosure can be transformed into banana or other plant genera.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and Agrobacterium-mediated transformation. See, for example, U.S. Pat. Nos. 5,405,765; 5,472,869; 5,538,877; 5,538,880; 5,550,318; 5,641,664; 5,736,369 and 5,736,369; International Patent Application Publication Nos. WO2002/038779 and WO/2009/117555; Lu et al., (Plant Cell Reports, 2008, 27:273-278); Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., Bio/Tech. 8:33-38 (1990)), each of which is expressly incorporated herein by reference in their entirety.

Agrobacterium tumefaciens is a naturally occurring bacterium that is capable of inserting its DNA (genetic information) into plants, resulting in a type of injury to the plant known as crown gall. Most species of plants can now be transformed using this method, including cucurbitaceous species.

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method.

The most common method for the introduction of new genetic material into a plant genome involves the use of living cells of the bacterial pathogen Agrobacterium tumefaciens to literally inject a piece of DNA, called transfer or T-DNA, into individual plant cells (usually following wounding of the tissue) where it is targeted to the plant nucleus for chromosomal integration. There are numerous patents governing Agrobacterium mediated transformation and particular DNA delivery plasmids designed specifically for use with Agrobacterium—for example, U.S. Pat. No. 4,536,475, EP0265556, EP0270822, WO8504899, WO8603516, U.S. Pat. No. 5,591,616, EP0604662, EP0672752, WO8603776, WO9209696, WO9419930, WO9967357, U.S. Pat. No. 4,399,216, WO8303259, U.S. Pat. No. 5,731,179, EP068730, WO9516031, U.S. Pat. Nos.

5,693,512, 6,051,757 and EP904362A1. Agrobacterium-mediated plant transformation involves as a first step the placement of DNA fragments cloned on plasmids into living Agrobacterium cells, which are then subsequently used for transformation into individual plant cells. Agrobacterium-mediated plant transformation is thus an indirect plant transformation method. Methods of Agrobacterium-mediated plant transformation that involve using vectors with no T-DNA are also well known to those skilled in the art and can have applicability in the present disclosure. See, for example, U.S. Pat. No. 7,250,554, which utilizes P-DNA instead of T-DNA in the transformation vector.

A transgenic plant formed using *Agrobacterium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

Direct plant transformation methods using DNA have also been reported. The first of these to be reported historically is electroporation, which utilizes an electrical current applied to a solution containing plant cells (M. E. Fromm et al., Nature, 319, 791 (1986); H. Jones et al., Plant Mol. Biol., 13, 501 (1989) and H. Yang et al., Plant Cell Reports, 7, 421 (1988). Another direct method, called "biolistic bombardment", uses ultrafine particles, usually tungsten or gold, that are coated with DNA and then sprayed onto the surface of a plant tissue with sufficient force to cause the particles to penetrate plant cells, including the thick cell wall, membrane and nuclear envelope, but without killing at least some of them (U.S. Pat. Nos. 5,204,253, 5,015,580). A third direct method uses fibrous forms of metal or ceramic consisting of sharp, porous or hollow needle-like projections that literally impale the cells, and also the nuclear envelope of cells. Both silicon carbide and aluminum borate whiskers have been used for plant transformation (Mizuno et al., 2004; Petolino et al., 2000; U.S. Pat. No. 5,302,523 US Application 20040197909) and also for bacterial and animal transformation (Kaepler et al., 1992; Raloff, 1990; Wang, 1995). There are other methods reported, and undoubtedly, additional methods will be developed. However, the efficiencies of each of these indirect or direct methods in introducing foreign DNA into plant cells are invariably extremely low, making it necessary to use some method for selection of only those cells that have been transformed, and further, allowing growth and regeneration into plants of only those cells that have been transformed.

For efficient plant transformation, a selection method must be employed such that whole plants are regenerated from a single transformed cell and every cell of the transformed plant carries the DNA of interest. These methods can employ positive selection, whereby a foreign gene is supplied to a plant cell that allows it to utilize a substrate present in the medium that it otherwise could not use, such as mannose or xylose (for example, refer U.S. Pat. Nos. 5,767, 378; 5,994,629). More typically, however, negative selection is used because it is more efficient, utilizing selective agents such as herbicides or antibiotics that either kill or inhibit the growth of non-transformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptII), which confers resistance to kanamycin and related antibiotics (see, for example, Messing & Vierra, Gene 19: 259-268 (1982); Bevan et al., Nature 304:184-187 (1983)). However, many different antibiotics and antibiotic resistance genes can be used for transformation purposes (refer U.S. Pat. Nos. 5,034,322, 6,174,724 and 6,255,560). In addition, several herbicides and herbicide resistance genes have been used for transformation purposes, including the bar gene, which confers resistance to the herbicide phosphinothricin (White et al., Nucl Acids Res 18: 1062 (1990), Spencer et al., Theor Appl Genet 79: 625-631(1990), U.S. Pat. Nos. 4,795,855, 5,378, 824 and 6,107,549). In addition, the dhfr gene, which confers resistance to the anticancer agent methotrexate, has been used for selection (Bourouis et al., EMBO J. 2(7): 1099-1104 (1983).

The expression control elements used to regulate the expression of a given protein can either be the expression control element that is normally found associated with the coding sequence (homologous expression element) or can be a heterologous expression control element. A variety of homologous and heterologous expression control elements are known in the art and can readily be used to make expression units for use in the present disclosure. Transcription initiation regions, for example, can include any of the various opine initiation regions, such as octopine, mannopine, nopaline and the like that are found in the Ti plasmids of *Agrobacterium tumefaciens*. Alternatively, plant viral promoters can also be used, such as the cauliflower mosaic virus 19S and 35S promoters (CaMV 19S and CaMV 35S promoters, respectively) to control gene expression in a plant (U.S. Pat. Nos. 5,352,605; 5,530,196 and 5,858,742 for example). Enhancer sequences derived from the CaMV can also be utilized (U.S. Pat. Nos. 5,164,316; 5,196,525; 5,322, 938; 5,530,196; 5,352,605; 5,359,142; and 5,858,742 for example). Lastly, plant promoters such as prolifera promoter, fruit specific promoters, Ap3 promoter, heat shock promoters, seed specific promoters, etc. can also be used.

Either a gamete-specific promoter, a constitutive promoter (such as the CaMV or Nos promoter), an organ-specific promoter (such as the E8 promoter from tomato), or an inducible promoter is typically ligated to the protein or antisense encoding region using standard techniques known in the art. The expression unit may be further optimized by employing supplemental elements such as transcription terminators and/or enhancer elements.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a pre-existing vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the *Agrobacterium* octopine synthase signal (Gielen et al., EMBO J 3:835-846 (1984)) or the nopaline synthase signal (Depicker et al., Mol. and Appl. Genet. 1:561-573 (1982)). The resulting expression unit is ligated into or otherwise constructed to be included in a vector that is appropriate for higher plant transformation. One or more expression units may be included in the same vector. The vector will typically contain a selectable marker gene expression unit by which transformed plant cells can be identified in culture. Usually, the marker gene will encode resistance to an antibiotic, such as G418, hygromycin, bleomycin, kanamycin, or gentamicin or to an herbicide, such as glyphosate (Round-Up) or glufosinate (BASTA) or atrazine. Replication sequences, of bacterial or viral origin, are generally also included to allow the vector to be cloned in a bacterial or phage host; preferably a broad host range for prokaryotic origin of replication is included. A selectable marker for bacteria may also be included to allow selection of bacterial cells bearing the desired construct. Suitable prokaryotic selectable markers include resistance to antibiotics such as ampicillin, kanamycin or tetracycline. Other DNA sequences encoding additional functions may also be present in the vector, as is known in the art. For instance, in the case of *Agrobacterium* transformations, T-DNA sequences will also be included for subsequent transfer to plant chromosomes.

To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as improved fatty acid composition, and to introduce these genes into already useful varieties of plants. Once the foreign genes have been introduced into a plant, that plant can then be used in imp plant breeding schemes (e.g., pedigree breeding, single-seed-descent breeding schemes, reciprocal recurrent selection) to produce progeny which also contain the gene of interest.

Genes can be introduced in a site directed fashion using homologous recombination. Homologous recombination permits site-specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451, 513; 5,501,967 and 5,527,695.

According to Ploetz (2015, Phytopathology 105:1512-1521), "Genetic transformation of bananas has become commonplace, and disease resistance is one of the most sought-after traits [citations omitted]." Techniques for transforming and regenerating banana plants are well known in the art. See, for example, U.S. Pat. Nos. 7,534,930; 6,133, 035; Sagi et al., Bio/Technology 13, 481-485, 1995; May et al., Bio/Technology 13, 485-492, 1995; Vishnevetsky et al., Transgenic Res. 20(1):61-71, 2011; Paul et al. (2011); Zhong et al., Plant Physiol. 110, 1097-1107, 1996; and, Dugdale et al., Journal of General Virology 79:2301-2311, 1998, each of which is expressly incorporated herein by reference in their entirety. For overviews and history, see, for example, Mohan and Swennen (editors), 2004, Banana improvement: cellular, molecular biology, and induced mutations, Science Publishers, Inc.; and, Remy et al., 2013, Genetically modified bananas: Past, present and future, Acta Horticulturae 974:71-80, each of which is expressly incorporated herein by reference in their entirety.

While reducing the present invention to practice, the inventor can construct an expression construct which includes nucleotide sequences encoding FUSR1, homologs of FusR1, orthologs of FusR1 and/or paralogs of FusR1, and/or fragments and variations thereof. The expression construct of the present invention can be introduced into embryogenic callus of commercial banana and the resulting transformed cells can be regenerated into plants. The transgenic banana plants is expected to have expression of FW-resistant FUSR1 protein and pathogen resistance.

According to one aspect of the present invention, there is provided a method of producing a disease resistant banana plant. The method is effected by transforming a banana cell with at least one exogenous polynucleotide encoding a polypeptide (such as FW-resistant FusR1) capable of conferring disease resistance to a banana plant.

According to another aspect of the present invention, there is provided a method of producing a disease resistant banana plant. The method is effected by transforming a banana cell with at least one exogenous expression cassette containing polynucleotides encoding a CRISPR-associated effector protein and a guide RNA capable of targeting at least one FW-sensitive FusR1 allele, thereby conferring disease resistance to a banana plant.

The banana cell of the present invention can be any banana variety or cultivar, including, but not limited to, commercially important *M. acuminata* (Cavendish, dwarf Cavendish, Grand Nain etc.). Preferably, the banana cell used for transformation is an embryogenic cell which is capable of forming a whole plant. More preferably, the banana cell is an embryogenic callus cell.

The phrase "embryogenic callus cell" used herein refers to an embryogenic cell contained in a cell mass produced in vitro.

Banana embryogenic callus cells suitable for transformation can be generated using well known methodology. For example, immature male flowers (inflorescences) can be dissected and incubated in M1 medium (see content in Table 1 herein below) under a reduced light intensity (50-100 lux) at 25° C. Following 3-5 months of incubation in M1 medium, yellow embryogenic calli are transferred to M2 medium (see content in Table 1 below) and incubated at 27° C. in the dark for at least four months to promote embryogenesis.

As is mentioned hereinabove, such banana embryogenic callus cells are suitable for transformation with a nucleic acid construct which includes at least one polynucleotide encoding a disease resistance polypeptide.

The phrases "polypeptide capable of conferring disease resistance" and "disease resistance polypeptide" are interchangeably used herein to refer to any peptide, polypeptide or protein which is capable of protecting a banana plant (expressing the polypeptide) from pathogen infection or the harmful effects resultant from pathogen infection.

A suitable disease resistance polypeptide can also be a polypeptide capable of inducing or enhancing resistance in plants such as described, for example in U.S. Pat. Nos. 6,091,004 and 6,316,697.

As is mentioned hereinabove, the method of the present invention is effected by transforming a banana cell with at least one polynucleotide encoding a polypeptide capable of conferring disease resistance to a banana plant.

In some embodiments, the banana cell is transformed with a polynucleotide sequence encoding FUSR1 protein from *Musa itinerans*, an example of which is set forth in SEQ ID NO: 1, SEQ ID NO: 2, SEQ ID NO: 4, and SEQ ID NO: 5.

In some embodiments, the banana cell is transformed with a polynucleotide sequence encoding FUSR1 protein from *Musa acuminata*, an example of which is set forth in SEQ ID NO: 8, SEQ ID NO: 9, SEQ ID NO: 10 and SEQ ID NO: 11

In some embodiments, the banana cell is transformed with a polynucleotide sequence encoding FUSR1 protein from *Musa basjoo*, an example of which is set forth in SEQ ID NO: 17, SEQ ID NO: 18, SEQ ID NO: 20, and SEQ ID NO: 21.

In some embodiments, the banana cell is transformed with a polynucleotide sequence encoding FUSR1 protein from *Musella lasiocarpa*, an example of which is set forth in SEQ ID NO: 23.

In some embodiments, the banana cell is transformed with a polynucleotide sequence encoding FUSR1 protein from *Musa balbisiana*, an example of which is set forth in SEQ ID NO: 26.

In some embodiments, plants transformed with just a single exogenous disease-resistance polypeptide, such as FUSR1, may exhibit only partial and short-lasting protection (see, for example, in Jach et al., Plant J. 8:97-108, 1995). In other embodiments, the banana cell/plant of the present invention preferably expresses a plurality of exogenous disease resistance polypeptides and is thus substantially more disease resistant than unmodified plants.

Several approaches can be utilized to transform and co-express these polynucleotides in plant cells.

Although less preferred, each of the above described polynucleotide sequences can be separately introduced into a banana cell by using three separate nucleic-acid constructs. In some embodiments, the three polynucleotide sequences can be co-introduced and co-expressed in the banana cell using a single nucleic acid construct. Such a construct can be designed with a single promoter sequences co-which can transcribe a polycistronic message including all three polynucleotide sequences. To enable co-translation of the three polypeptides encoded by the polycistronic message, the polynucleotide sequences can be inter-linked via an internal ribosome entry site (IRES) sequence which facilitates translation of polynucleotide sequences positioned downstream of the IRES sequence. In this case, a transcribed polycistronic RNA molecule encoding the three polypeptides described above will be translated from both the capped 5' end and the two internal IRES sequences of the polycistronic RNA molecule to thereby produce in the cell all three polypeptides.

Alternatively, the polynucleotide segments encoding the plurality of polypeptides capable of conferring disease resistance can be translationally fused via a protease recognition site cleavable by a protease expressed by the cell to be transformed with the nucleic acid construct. In this case, a chimeric polypeptide translated will be cleaved by a cell-expressed protease to thereby generate the plurality of polypeptides.

In other embodiments, the present invention utilizes a nucleic acid construct which includes three promoter sequences each capable of directing transcription of a specific polynucleotide sequence of the polynucleotide sequences described above.

Suitable promoters which can be used with the nucleic acid of the present invention include constitutive, inducible, or tissue-specific promoters.

Suitable constitutive promoters include, for example, CaMV 35S promoter (Odell et al., Nature 313:810-812, 1985); maize Ubi 1 (Christensen et al., Plant Sol. Biol. 18:675-689, 1992); rice actin (McElroy et al., Plant Cell 2:163-171, 1990); pEMU (Last et al., Theor. Appl. Genet. 81:581-588, 1991); and Synthetic Super MAS (Ni et al., The Plant Journal 7: 661-76, 1995). Other constitutive promoters include those in U.S. Pat. Nos. 5,659,026, 5,608,149; 5,608, 144; 5,604,121; 5,569,597: 5,466,785; 5,399,680; 5,268, 463; and 5,608,142.

Suitable inducible promoters can be pathogen-inducible promoters such as, for example, the alfalfa PR10 promoter (Coutos-Thevenot et al., Journal of Experimental Botany 52: 901-910, 2001 and the promoters described by Marineau et al., Plant Mol. Biol. 9:335-342, 1987; Matton et al. Molecular Plant-Microbe Interactions 2:325-331, 1989; Somsisch et al., Proc. Natl. Acad. Sci. USA 83:2427-2430, 1986: Somsisch et al., Mol. Gen. Genet. 2:93-98, 1988; and Yang, Proc. Natl. Acad. Sci. USA 93:14972-14977, 1996.

Suitable tissue-specific promoters include, but not limited to, leaf-specific promoters such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993.

The nucleic acid construct of the present invention may also include at least one selectable marker such as, for example, nptII. Preferably, the nucleic acid construct is a shuttle vector, which can propagate both in *E. coli* (wherein the construct comprises an appropriate selectable marker and origin of replication) and be compatible for propagation in cells. The construct according to the present invention can be, for example, a plasmid, a bacmid, a phagemid, a cosmid, a phage, a virus or an artificial chromosome, preferably a plasmid.

The nucleic acid construct of the present invention can be utilized to stably transform banana cells. The principle methods of causing stable integration of exogenous DNA into banana genome include two main approaches:

(i) Agrobacterium-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990)

79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The Agrobacterium system includes the use of plasmid vectors that contain defined DNA segments that integrate into the plant genomic DNA. Methods of inoculation of the plant tissue vary depending upon the plant species and the Agrobacterium delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the Agrobacterium delivery system in combination with vacuum infiltration. Suitable Agrobacterium-mediated procedures for introducing exogenous DNA to banana cells is described by Dougale et al. (Journal of General Virology, 79:2301-2311, 1998) and in U.S. Pat. No. 6,395,962.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Alternatively, the nucleic acid construct of the present invention can be introduced into banana cells by a microprojectiles bombardment. In this technique, tungsten or gold particles coated with exogenous DNA are accelerated toward the target cells. Suitable banana transformation procedures by microprojectiles bombardment are described by Sagi et al. (Biotechnology 13:481-485, 1995) and by Dougale et al. (Journal of General Virology, 79:2301-2311, 1998). Preferably, the nucleic acid construct of the present invention is introduced into banana cells by a microprojectiles bombardment procedure as described in Example 4 herein below.

Following transformation, the transformed cells are micropropagated to provide a rapid, consistent reproduction of the transformed material.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Thus, transformed banana cells can be micropropagated and regenerated into plants using methods known in the art such as described, for example in U.S. Pat. No. 6,133,035 and by Novak et al., 1989; Dhed'a et al., 1991; Cote et al., 1996; Becker et al., 2000; Sagi et al. Plant Cell Reports 13:262-266, 1994; Grapin et al., Cell Dev. Biol. Plant. 32:66-71, 1996; Marroquin et al., In Vivo Cell. Div. Biol. 29P:43-46, 1993; and Escalant et al., In Vivo Cell Dev. Biol. 30:181-186, 1994).

Stable integration of exogenous DNA sequence in the genome of the transformed plants can be determined using standard molecular biology techniques well known in the art such as PCR and Southern blot hybridization.

Although stable transformation is presently preferred, transient transformation of cultured cells, leaf cells, meristematic cells or the whole plant is also envisaged by the present invention.

Transient transformation can be effected by any of the direct DNA transfer methods described above or by viral infection using modified plant viruses.

Viral infection is preferred since is enables circumventing micropropagation and regeneration of a whole plant from cultured cells. Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman et al. (Communications in Molecular Biology: Viral Vectors, Cold Spring Harbor Laboratory, New York, pp. 172-189, 1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson et al. (Virology 172:285-292, 1989; Takamatsu et al. EMBO J. 6:307-311, 1987; French et al. (Science 231:1294-1297, 1986); and Takamatsu et al. (FEBS Letters 269:73-76, 1990).

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA.

If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that the sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

In addition to the above, the nucleic acid molecule of the present invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

In case that the exogenous polypeptide confers disease resistance to the plant, the expression can be determined based on increased in resistance or tolerance to pathogens, preferably in comparison with similar wild-type (non-transformed) plant. Comparative evaluation of plants for their resistance or tolerance to pathogens can be effected using in vitro or in vivo bioassays well known in the art of plant pathology such as described, for example by Agrios, G. N., ed. (Plant Pathology, Third Edition, Academic Press, New York, 1988).

Evaluating plant resistance or tolerance to pathogens can be effected by exposing a pathogen to an extract obtained from plant tissue and determining the effect of the extract on the pathogen growth in vitro. In some embodiments, evaluating plant resistance or tolerance to pathogens is effected by exposing a pathogen to a plant tissue (e.g., a leaf tissue).

In other embodiments, evaluating plant resistance or tolerance to pathogens is effected by exposing a pathogen to a whole plant. For example, evaluating plant resistance or tolerance to *Fusarium oxysporum* f. sp. *Cubense* (Foc) (the causal agent of Panama disease) can be effected by planting transformed banana plants in an open field in a close proximity to non-transformed plants which are infected with the pathogen (used as a source of inoculum). The disease severity which subsequently develops in transformed plants is evaluated comparatively to non-transformed plants. The disease severity is preferably evaluated visually (the damage usually appears on suckers which have at least 5-12 leaves) and statistically analyzed to determine significant differences in resistance or tolerance between plant lines to the Panama disease.

Hence, the present invention provides nucleic acid constructs including one or more polynucleotides encoding disease resistance polypeptides, transformed banana cells and transformed banana plants expressing exogenous disease resistance traits, and methods of producing same.

VI. Breeding Methods

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988). For population improvement methods specific for soybean see, e.g., J. R. Wilcox, editor (1987) SOYBEANS: Improvement, Production, and Uses, Second Edition, American Society of Agronomy, Inc., Crop Science Society of America, Inc., and Soil Science Society of America, Inc., publishers, 888 pages.

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enters a synthetic varies widely. In practice, numbers of parental lines range from 10 to several hundred, with 100-200 being the average. Broad based synthetics formed from 100 or more clones would be expected to be more stable during seed multiplication than narrow based synthetics.

Hybrids. As discussed above, hybrid is an individual plant resulting from a cross between parents of differing genotypes. Commercial hybrids are now used extensively in many crops, including corn (maize), sorghum, sugar beet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

Bulk Segregation Analysis (BSA). BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markers in specific genomic regions by using segregating populations. *Proceedings of the National Academy of Sciences*, USA, 99:9828-9832) and Quarrie et al. (Quarrie et al., Bulk segregant analysis with molecular markers and its use for improving drought resistance in maize, 1999, *Journal of Experimental Botany*, 50(337):1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to pathogen), and the other from the individuals having reversed phenotype (e.g., susceptible to pathogen), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs). Markers linked to the phenotype can be identified and used for breeding or QTL mapping.

Gene Pyramiding. The method to combine into a single genotype a series of target genes identified in different parents is usually referred as gene pyramiding. The first part of a gene pyramiding breeding is called a pedigree and is aimed at cumulating one copy of all target genes in a single genotype (called root genotype). The second part is called the fixation steps and is aimed at fixing the target genes into a homozygous state, that is, to derive the ideal genotype (ideotype) from the root genotype. Gene pyramiding can be combined with marker assisted selection (MAS, see Hospital et al., 1992, 1997a, and 1997b, and Moreau et al, 1998) or marker based recurrent selection (MBRS, see Hospital et al., 2000).

Banana breeding programs, especially for edible bananas, is hampered by high sterility, triploidy and seedlessness. Few diploid banana clones produce viable pollen, and the germplasm of commercial banana clones is both male- and female-sterile. In spite of these problems and challenges, important progress has been made in the genetic improvement of *Musa* in recent years, and new varieties are not becoming available from banana breeding programs (Escalant and Jain, Chapter 30, Banana improvement with cellular and molecular biology, and induced mutations: future and perspectives, 8 pages, In Jain and Swennan, editors, Banana Improvement: Cellular, Molecular Biology, and Induced Mutations, 2004, Food and Agriculture Organization of the United Nations, Science Publishers, Inc.).

For information on banana breeding see, for example, Heslop-Harrison and Schwarzacher, Annals of Botany 100: 1073-1084, 2007; Bakry et al., Chapter 1, Genetic Improvement in Banana, 50 pages, In Breeding Plantation Tree Crops: Tropical Species, 2009; Heslop-Harrison et al., Genomics, Banana Breeding and Superdomestication, Acta Hort. 897:55-62, 2011; Jenny et al., In Jacome et al., editors, *Mycosphaerella* leaf spot diseases of banana: present status and outlook, Proceedings of the 2$^{nd}$ International Workshop on *Mycosphaerella* leaf spot diseases held in San José, Costa Rica, 20-23 May 2002, Session 4, pages 199-208; Ortiz et al., Banana and Plantain Breeding, Chapter 10, pages 110-146, In Gowen et al., editors, Bananas and Plantains, World Crop Series, Springer Link, 1995; Batte et al., Frontiers in Plant Science, Volume 10, Article 81, 9 pages, February 2019.

VII. Gene Editing

As used herein, the term "gene editing system" refers to a system comprising one or more DNA-binding domains or components and one or more DNA-modifying domains or components, or isolated nucleic acids, e.g., one or more vectors, encoding said DNA-binding and DNA-modifying domains or components. Gene editing systems are used for modifying the nucleic acid of a target gene and/or for modulating the expression of a target gene. In known gene editing systems, for example, the one or more DNA-binding domains or components are associated with the one or more DNA-modifying domains or components, such that the one or more DNA-binding domains target the one or more DNA-modifying domains or components to a specific nucleic acid site. Methods and compositions for enhancing gene editing is well known in the art. See example, U.S. Patent Application Publication No. 2018/0245065, which is incorporated by reference in its entirety.

Certain gene editing systems are known in the art, and include but are not limited to, zinc finger nucleases, transcription activator-like effector nucleases (TALEN5); clustered regularly interspaced short palindromic repeats (CRISPR)/Cas systems, meganuclease systems, and viral vector-mediated gene editing.

In some embodiments, the present disclosure teaches methods for gene editing/cloning utilizing DNA nucleases. CRISPR complexes, transcription activator-like effector nucleases (TALEN5), zinc finger nucleases (ZFNs), and FokI restriction enzymes, which are some of the sequence-specific nucleases that have been used as gene editing tools. These enzymes are able to target their nuclease activities to desired target loci through interactions with guide regions engineered to recognize sequences of interest. In some embodiments, the present disclosure teaches CRISPR-based gene editing methods to genetically engineer the genome of banana species of the present disclosure in order to stimulate, enhance, or modulate disease resistance to pathogens.

(i) CRISPR Systems

CRISPR (Clustered Regularly Interspaced Short Palindromic Repeats) and CRISPR-associated (cas) endonucleases were originally discovered as adaptive immunity systems evolved by bacteria and archaea to protect against viral and plasmid invasion. Naturally occurring CRISPR/Cas systems in bacteria are composed of one or more Cas genes and one or more CRISPR arrays consisting of short palindromic repeats of base sequences separated by genome-targeting sequences acquired from previously encountered viruses and plasmids (called spacers). (Wiedenheft, B., et. al. Nature. 2012; 482:331; Bhaya, D., et. al., Annu. Rev. Genet. 2011; 45:231; and Terms, M. P. et. al., Curr. Opin. Microbiol. 2011; 14:321). Bacteria and archaea possessing one or more CRISPR loci respond to viral or plasmid challenge by integrating short fragments of foreign sequence (protospacers) into the host chromosome at the proximal end of the CRISPR array. Transcription of CRISPR loci generates a library of CRISPR-derived RNAs (crRNAs) containing sequences complementary to previously encountered invading nucleic acids (Haurwitz, R. E., et. al., Science. 2012:329; 1355; Gesner, E. M., et. al., Nat. Struct. Mol. Biol. 2001:18; 688; Jinek, M., et. al., Science. 2012:337; 816-21). Target recognition by crRNAs occurs through complementary base pairing with target DNA, which directs cleavage of foreign sequences by means of Cas proteins. (Jinek et. al. 2012 "A Programmable dual-RNA-guided DNA endonuclease in adaptive bacterial immunity." Science. 2012:337; 816-821).

There are at least five main CRISPR system types (Type I, II, III, IV and V) and at least 16 distinct subtypes (Makarova, K. S., et al., Nat Rev Microbiol. 2015. Nat. Rev. Microbiol. 13, 722-736). CRISPR systems are also classified based on their effector proteins. Class 1 systems possess multi-subunit crRNA-effector complexes, whereas in Class 2 systems all functions of the effector complex are carried out by a single protein (e.g., Cas9 or Cpf1). In some embodiments, the present disclosure provides using type II and/or type V single-subunit effector systems.

As these naturally occur in many different types of bacteria, the exact arrangements of the CRISPR and structure, function and number of Cas genes and their product differ somewhat from species to species. Haft et al. (2005) *PLoS Comput. Biol.* 1: e60; Kunin et al. (2007) *Genome Biol.* 8: R61; Mojica et al. (2005) *J. Mol. Evol.* 60: 174-182; Bolotin et al. (2005) *Microbiol.* 151: 2551-2561; Pourcel et al. (2005) *Microbiol.* 151: 653-663; and Stern et al. (2010) *Trends. Genet.* 28: 335-340. For example, the Cse (Cas subtype, *E. coli*) proteins (e.g., CasA) form a functional complex, Cascade, which processes CRISPR RNA transcripts into spacer-repeat units that Cascade retains. Brouns et al. (2008) Science 321: 960-964. In other prokaryotes, Cas6 processes the CRISPR transcript. The CRISPR-based phage inactivation in *E. coli* requires Cascade and Cas3, but not Cas1 or Cas2. The Cmr (Cas RAMP module) proteins in *Pyrococcus furiosus* and other prokaryotes form a functional complex with small CRISPR RNAs that recognizes and cleaves complementary target RNAs. A simpler CRISPR system relies on the protein Cas9, which is a nuclease with two active cutting sites, one for each strand of the double helix. Combining Cas9 and modified CRISPR locus RNA can be used in a system for gene editing. Pennisi (2013) Science 341: 833-836.

(ii) CRISPR/Cas9

In some embodiments, the present disclosure provides methods of gene editing using a Type II CRISPR system. Type II systems rely on a i) single endonuclease protein, ii) a transactivating crRNA (tracrRNA), and iii) a crRNA where a ~20-nucleotide (nt) portion of the 5' end of crRNA is complementary to a target nucleic acid. The region of a CRISPR crRNA strand that is complementary to its target DNA protospacer is hereby referred to as "guide sequence."

In some embodiments, the tracrRNA and crRNA components of a Type II system can be replaced by a single guide RNA (sgRNA), also known as a guide RNA (gRNA). The sgRNA can include, for example, a nucleotide sequence that comprises an at least 12-20 nucleotide sequence complementary to the target DNA sequence (guide sequence) and can include a common scaffold RNA sequence at its 3' end. As used herein, "a common scaffold RNA" refers to any RNA sequence that mimics the tracrRNA sequence or any RNA sequences that function as a tracrRNA.

Cas9 endonucleases produce blunt end DNA breaks, and are recruited to target DNA by a combination of a crRNA and a tracrRNA oligos, which tether the endonuclease via complementary hybridization of the RNA CRISPR complex.

In some embodiments, DNA recognition by the crRNA/endonuclease complex requires additional complementary base-pairing with a protospacer adjacent motif (PAM) (e.g., 5'-NGG-3') located in a 3' portion of the target DNA, downstream from the target protospacer. (Jinek, M., et. al., Science. 2012, 337:816-821). In some embodiments, the PAM motif recognized by a Cas9 varies for different Cas9 proteins.

In some embodiments the Cas9 disclosed herein can be any variant derived or isolated from any source. In other embodiments, the Cas9 peptide of the present disclosure can include one or more of the mutations described in the literature, including but not limited to the functional mutations described in: Fonfara et al. Nucleic Acids Res. 2014 February; 42(4):2577-90; Nishimasu H. et al. Cell. 2014 Feb. 27,156(5):935-49; Jinek M. et al. Science. 2012 337: 816-21; and Jinek M. et al. Science. 2014 Mar. 14, 343 (6176); see also U.S. patent application Ser. No. 13/842,859, filed Mar. 15, 2013, which is hereby incorporated by reference; further, see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, which are all hereby incorporated by reference. Thus, in some embodiments, the systems and methods disclosed herein can be used with the wild type Cas9 protein having double-stranded nuclease activity, Cas9 mutants that act as single stranded nickases, or other mutants with modified nuclease activity.

According to the present disclosure, Cas9 molecules of, derived from, or based on the Cas9 proteins of a variety of species can be used in the methods and compositions described herein. For example, Cas9 molecules of, derived from, or based on, e.g., *S. pyogenes, S. thermophilus, Staphylococcus aureus* and/or *Neisseria meningitidis* Cas9 molecules, can be used in the systems, methods and compositions described herein. Additional Cas9 species include: *Acidovorax avenae, Actinobacillus pleuropneumonias, Actinobacillus succinogenes, Actinobacillus suis, Actinomyces* sp., *Cycliphilus denitrificans, Aminomonas paucivorans, Bacillus cereus, Bacillus smithii, Bacillus thuringiensis, Bacteroides* sp., *Blastopirellula marina, Bradyrhiz obium* sp., *Brevibacillus latemsporus, Campylobacter coli, Campylobacter jejuni, Campylobacter lad, Candidatus Puniceispirillum, Clostridiu cellulolyticum, Clostridium perfringens, Corynebacterium accolens, Corynebacterium diphtheria, Corynebacterium matruchotii, Dinoroseobacter sliibae, Eubacterium dolichum, Gamma proteobacterium, Gluconacetobacler diazotrophicus, Haemophilus parainfluenzae, Haemophilus sputorum, Helicobacter canadensis, Helicobacter cinaedi, Helicobacter mustelae, Ilyobacler polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica. Neisseria* sp., *Neisseria wadsworthii, Nitrosomonas* sp *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus lugdunensis, Streptococcus* sp., *Subdoligranulum* sp., *Tislrella mobilis, Treponema* sp., or *Verminephrobacter eiseniae*.

In some embodiments, the present disclosure teaches the use of tools for genome editing techniques in plants such as crops and methods of gene editing using CRISPR-associated (cas) endonucleases including SpyCas9, SaCas9, St1Cas9. These powerful tools for genome editing, which can be applied to plant genome editing are well known in the art. See example, Song et al. (2016), CRISPR/Cas9: A powerful tool for crop genome editing, *The Crop Journal* 4:75-82, Mali et al. (2013) RNA-guided human genome engineering via cas9, Science 339: 823-826; Ran et al. (2015) In vivo genome editing using *Staphylococcus aureus* cas9, Nature 520: 186-191; Esvelt et al. (2013) Orthogonal cas9 proteins for ma-guided gene regulation and editing, Nature methods 10(11): 1116-1121, each of which is hereby incorporated by reference in its entirety for all purposes.

(iii) CRISPR/Cpf1

In other embodiments, the present disclosure provides methods of gene editing using a Type V CRISPR system. In some embodiments, the present disclosure provides methods of gene editing using CRISPR from *Prevotella, Francisella, Acidaminococcus, Lachnospiraceae,* and *Moraxella* (Cpf1).

The Cpf1 CRISPR systems of the present disclosure comprise i) a single endonuclease protein, and ii) a crRNA, wherein a portion of the 3' end of crRNA contains the guide sequence complementary to a target nucleic acid. In this system, the Cpf1 nuclease is directly recruited to the target DNA by the crRNA. In some embodiments, guide sequences for Cpf1 must be at least 12 nt, 13 nt, 14 nt, 15 nt, or 16 nt in order to achieve detectable DNA cleavage, and a minimum of 14 nt, 15 nt, 16 nt, 17 nt, or 18 nt to achieve efficient DNA cleavage.

The Cpf1 systems of the present disclosure differ from Cas9 in a variety of ways. First, unlike Cas9, Cpf1 does not require a separate tracrRNA for cleavage. In some embodiments, Cpf1 crRNAs can be as short as about 42-44 bases long—of which 23-25 nt is guide sequence and 19 nt is the constitutive direct repeat sequence. In contrast, the combined Cas9 tracrRNA and crRNA synthetic sequences can be about 100 bases long.

Second, certain Cpf1 systems prefer a "TTN" PAM motif that is located 5' upstream of its target. This is in contrast to the "NGG" PAM motifs located on the 3' of the target DNA for common Cas9 systems such as *Streptococcus pyogenes* Cas9. In some embodiments, the uracil base immediately preceding the guide sequence cannot be substituted (Zetsche, B. et al. 2015. "Cpf1 Is a Single RNA-Guided Endonuclease of a Class 2 CRISPR-Cas System" Cell 163, 759-771, which is hereby incorporated by reference in its entirety for all purposes).

Third, the cut sites for Cpf1 are staggered by about 3-5 bases, which create "sticky ends" (Kim et al., 2016. "Genome-wide analysis reveals specificities of Cpf1 endonucleases in human cells" published online Jun. 6, 2016). These sticky ends with 3-5 nt overhangs are thought to facilitate NHEJ-mediated-ligation, and improve gene editing of DNA fragments with matching ends. The cut sites are in the 3' end of the target DNA, distal to the 5' end where the PAM is. The cut positions usually follow the 18th base on the non-hybridized strand and the corresponding 23rd base on the complementary strand hybridized to the crRNA.

Fourth, in Cpf1 complexes, the "seed" region is located within the first 5 nt of the guide sequence. Cpf1 crRNA seed regions are highly sensitive to mutations, and even single base substitutions in this region can drastically reduce cleavage activity (see Zetsche B. et al. 2015 "Cpf1 Is a Single RNA-Guided Endonuclease of a Class 2 CRISPR-Cas System" Cell 163, 759-771). Critically, unlike the Cas9 CRISPR target, the cleavage sites and the seed region of Cpf1 systems do not overlap. Additional guidance on designing Cpf1 crRNA targeting oligos is available on Zetsche B. et al. 2015. ("Cpf1 Is a Single RNA-Guided Endonuclease of a Class 2 CRISPR-Cas System" Cell 163, 759-771).

(iv) Guide RNA (gRNA)

In some embodiments, the guide RNA of the present disclosure comprises two coding regions, encoding for crRNA and tracrRNA, respectively. In other embodiments, the guide RNA is a single guide RNA (sgRNA) synthetic crRNA/tracrRNA hybrid. In other embodiments, the guide RNA is a crRNA for a Cpf1 endonuclease.

Persons having skill in the art will appreciate that, unless otherwise noted, all references to a single guide RNA (sgRNA) in the present disclosure can be read as referring to a guide RNA (gRNA). Therefore, embodiments described in the present disclosure which refer to a single guide RNA (sgRNA) will also be understood to refer to a guide RNA (gRNA).

The guide RNA is designed so as to recruit the CRISPR endonuclease to a target DNA region. In some embodiments, the present disclosure teaches methods of identifying viable target CRISPR landing sites, and designing guide RNAs for targeting the sites. For example, in some embodiments, the present disclosure teaches algorithms designed to facilitate the identification of CRISPR landing sites within target DNA regions.

In some embodiments, the present disclosure teaches use of software programs designed to identify candidate CRISPR target sequences on both strands of an input DNA sequence based on desired guide sequence length and a CRISPR motif sequence (PAM, protospacer adjacent motif) for a specified CRISPR enzyme. For example, target sites for Cpf1 from *Francisella novicida* U112, with PAM sequences TTN, may be identified by searching for 5'-TTN-3' both on the input sequence and on the reverse-complement of the input. The target sites for Cpf1 from Lachnospiraceae bacterium and Acidaminococcus sp., with PAM sequences TTTN, may be identified by searching for 5'-TTTN-3' both on the input sequence and on the reverse complement of the input. Likewise, target sites for Cas9 of *S. thermophilus* CRISPR, with PAM sequence NNAGAAW, may be identified by searching for 5'-Nx-NNAGAAW-3' both on the input sequence and on the reverse-complement of the input. The PAM sequence for Cas9 of *S. pyogenes* is 5'-NGG-3'.

Since multiple occurrences in the genome of the DNA target site may lead to nonspecific genome editing, after identifying all potential sites, sequences may be filtered out based on the number of times they appear in the relevant reference genome or modular CRISPR construct. For those CRISPR enzymes for which sequence specificity is determined by a 'seed' sequence (such as the first 5 bp of the guide sequence for Cpf1-mediated cleavage) the filtering step may also account for any seed sequence limitations.

In some embodiments, algorithmic tools can also identify potential off target sites for a particular guide sequence. For example, in some embodiments Cas-Offinder can be used to identify potential off target sites for Cpf1 (see Kim et al., 2016. "Genome-wide analysis reveals specificities of Cpf1 endonucleases in human cells" Nature Biotechnology 34, 863-868). Any other publicly available CRISPR design/identification tool may also be used, including for example the Zhang lab crispr.mit.edu tool (see Hsu, et al. 2013 "DNA targeting specificity of RNA guided Cas9 nucleases" Nature Biotech 31, 827-832).

In some embodiments, the user may be allowed to choose the length of the seed sequence. The user may also be allowed to specify the number of occurrences of the seed: PAM sequence in a genome for purposes of passing the filter. The default is to screen for unique sequences. Filtration level is altered by changing both the length of the seed sequence and the number of occurrences of the sequence in the genome. The program may in addition or alternatively provide the sequence of a guide sequence complementary to the reported target sequence(s) by providing the reverse complement of the identified target sequence(s).

In the guide RNA, the "spacer/guide sequence" sequence is complementary to the "proto spacer" sequence in the DNA target. The gRNA" scaffold" for a single stranded gRNA structure is recognized by the Cas9 protein.

In some embodiments, the transgenic plant, plant part, plant cell, or plant tissue culture taught in the present disclosure comprise a recombinant construct, which comprises at least one nucleic acid sequence encoding a guide RNA. In some embodiments, the nucleic acid is operably linked to a promoter. In other embodiments, a recombinant construct further comprises a nucleic acid sequence encoding a Clustered regularly interspaced short palindromic repeats (CRISPR) endonuclease. In other embodiments, the guide RNA is capable of forming a complex with said CRISPR endonuclease, and said complex is capable of binding to and creating a double strand break in a genomic target sequence of said plant genome. In other embodiments, the CRISPR endonuclease is Cas9.

In further embodiments, the target sequence is a nucleic acid for FusR1, homologs of FusR1, orthologs of FusR1 and/or paralogs of FusR1, and/or fragments and variations thereof. In some embodiments, the present disclosure teaches the gene editing of FusR1 in FW-sensitive banana varieties susceptible to Fusarium pathogens using genetic engineering techniques described herein.

The present disclosure teaches the targeted gene-editing techniques for modulating, stimulating, and enhancing disease resistance by turning FW-sensitive alleles to FW-resistant alleles based on sequence information given in the present disclosure. The present disclosure teaches sequence information of both FW-resistant alleles and FW-sensitive alleles. Using CRISPR/Cas system, FW-resistant traits are introduced into FW-sensitive banana varieties.

In some embodiments, FW-sensitive FusR1 alleles are to be targeted for knock-out. In some embodiments, sequences of conserved regions responsible for FW sensitivity trait can be used to make gene editing machineries (such as CRISPR-associated effector proteins, ZFN, TALEN etc.) to target one or more FusR1 orthologs.

In some embodiments, the disrupting of expression of the endogenous FW-sensitive alleles is carried out by a gene-editing technology. In some embodiments, the knock-out of FW-sensitive alleles is carried out by gene-editing technology. In some embodiments, the base-editing of FW-sensitive alleles into FW-resistant alleles is carried out by gene-editing technology. In some embodiments, the gene-editing technology is a ZFN. In other embodiments, the gene-editing technology is a TALEN. In further embodiments, the gene-editing technology is a CRISPR/Cas system. In further embodiments, said CRISPR system comprises a nucleic acid molecule and an enzymatic protein, wherein the nucleic acid molecule is a guide RNA (gRNA) molecule and the enzymatic protein is a Cas protein or Cas ortholog. In further embodiments, at least two expression cassettes are stacked in tandem in the expression vector.

In some embodiments, the modified plant cells comprise one or more modifications (e.g., insertions, deletions, or mutations of one or more nucleic acids) in the genomic DNA sequence of an endogenous target gene resulting in the altered function the endogenous gene, thereby modulating, stimulating, or enhancing disease resistance. In such embodiments, the modified plant cells comprise a "modified endogenous target gene." In some embodiments, the modifications in the genomic DNA sequence cause mutation, thereby altering the function of FW-sensitive FUSR1 protein to FW-resistant FUSR1 protein. In some embodiments, the modifications in the genomic DNA sequence results in amino acid substitutions, thereby altering the normal function of the encoded protein. In some embodiments, the modifications in the genomic DNA sequence encode a modified endogenous protein with modulated, altered, stimulated or enhanced function of disease/pathogen resistance compared to the unmodified (i.e., FW-sensitive) version of the endogenous protein in the FW-sensitive banana accessions.

In some embodiments, the modified plant cells described herein comprise one or more modified endogenous target genes, wherein the one or more modifications result in an altered function of a gene product (i.e., a protein) encoded by the endogenous target gene compared to an unmodified plant cell. For example, in some embodiments, a modified plant cell demonstrates expression of a FW-resistant FUSR1 protein or an upregulated expression of said protein. In some embodiments, the expression of the gene product (such as genetically-engineered FW-resistant FusR1 from FW-sensitive FusR1) in a modified plant cell is enhanced by at least 0.5%, 1%, 2%, 3%, 4%, 5% or higher compared to the expression of the gene product (such as FW-sensitive FusR1) in an unmodified plant cell. In other embodiments, the expression of the gene product (such as genetically-engineered FW-resistant FusR1) in a modified plant cell is enhanced by at least 10%, 20%, 30%, 40%, 50%, 60%, 70%, 80%, 90%, or more compared to the expression of the gene product (such as FW-sensitive FusR1) in an unmodified plant cell. In some embodiments, the modified plant cells described herein demonstrate enhanced expression and/or function of gene products encoded by a plurality (e.g., two or more) of endogenous target genes compared to the expression of the gene products in an unmodified plant cell. For example, in some embodiments, a modified plant cell demonstrates enhanced expression and/or function of gene products from 2, 3, 4, 5, 6, 7, 8, 9, 10, or more endogenous target genes compared to the expression of the gene products in an unmodified plant cell.

In some embodiments, the modified plant cells described herein comprise one or more modified endogenous target genes, wherein the one or more modifications to the target DNA sequence results in expression of a protein with reduced or altered function (e.g., a "modified endogenous protein") compared to the function of the corresponding protein expressed in an unmodified plant cell (e.g., a "unmodified endogenous protein"). In some embodiments, the modified plant cells described herein comprise 2, 3, 4, 5, 6, 7, 8, 9, 10, or more modified endogenous target genes encoding 2, 3, 4, 5, 6, 7, 8, 9, 10, or more modified endogenous proteins. In some embodiments, the modified endogenous protein demonstrates enhanced or altered binding affinity for another protein expressed by the modified plant cell or expressed by another cell; enhanced or altered signaling capacity; enhanced or altered enzymatic activity; enhanced or altered DNA-binding activity; or reduced or altered ability to function as a scaffolding protein.

EXAMPLES

The present invention is further illustrated by the following examples that should not be construed as limiting. The contents of all references, patents, and published patent applications cited throughout this application, as well as the Figures, are incorporated herein by reference in their entirety for all purposes.

Example 1: Methods and Materials for Sequencing (1) Material

Fresh and lyophilized banana leaf tissues were obtained from Bioversity International (Leuven, Belgium), Inter-TROP CRB Plantes Tropicales (Guadeloupe), and the IITA Genebank (Ibadan, Nigeria), Plant Delights Nursery (Raleigh, NC), and The Flower Bin (Longmont, CO).

(2) RNA

Total RNA was extracted from fresh, frozen, and lyophilized banana leaves using a modified Ishihara protocol (Ishihara et al., 2016). Approximately 100 mg of fresh or frozen banana tissue was ground to a powder using a clean, dry-ice cooled mortar and pestle that was treated with RNase Away™ (Invitrogen, Carlsbad, CA). Approximately 20-30 mg of lyophilized banana tissue was homogenized in a Lysing Matrix D Tube (MP Bio, Santa Ana, CA) without liquid. One milliliter of polyphenol lysis buffer (800 µl RLT buffer (Qiagen, Germantown, MD), 200 µl of Fruit-mate (Takara, Mountain View, CA), and 10 µl of β-mercaptoethanol) was added to each sample. Fresh and frozen samples were homogenized for 40 seconds on the speed 6 setting of a FastPrep 120 (ThermoFisher Scientific, Waltham, MA), while lyophilized samples were vortexed on high for 1 minute. All samples were incubated on ice for 4 minutes, then centrifuged for 2 minutes at 8000× g. The supernatant was transferred to a new 2.0 ml tube and another 1.0 ml of polyphenol lysis buffer was added to the supernatant. Samples were vortexed on high for 1 minute, incubated on ice for 4 minutes, and centrifuged for 2 minutes at 8000×g. The supernatant was split between two QIAshredder columns (Qiagen, Germantown, MD) and centrifuged on maximum speed for 2 minutes until all supernatant had been processed. The remaining steps of RNA extraction were carried out according to the Ishihara protocol. The optional in-solution DNase digestion and RNA cleanup protocol was also performed as detailed in the RNeasy Mini protocol (Qiagen, Germantown, MD). Sample concentration and purity was determined using the NanoDrop™ One (ThermoFisher Scientific, Waltham, MA) spectrophotometer.

(3) DNA

Total DNA was extracted from fresh, frozen, and lyophilized banana leaves using a modified PowerPlant Pro DNA Isolation Kit protocol (MO BIO, Carlsbad, CA). Approximately 40 mg of fresh or frozen banana tissue was ground to a powder using a cleaned, dry-ice cooled mortar and pestle that was treated with RNase Away™ (Invitrogen, Carlsbad, CA). Approximately 10-20 mg of lyophilized banana tissue was homogenized in a Lysing Matrix D Tube (MP Bio, Santa Ana, CA) without liquid. The remaining steps of DNA extraction were carried out according to the MO BIO protocol. Phenolic Separation Solution was added to the lysis buffer and 250 µl of PD3 buffer was used. Sample concentration and purity was determined using the NanoDrop™ One (ThermoFisher Scientific, Waltham, MA) spectrophotometer.

(4) cDNA cDNA was synthesized from 1.0 µg of total RNA using the 1st Strand cDNA Synthesis Kit (Epicentre, Madison, WI). The adapter primer (AP) from Invitrogen's 3'-RACE kit (Invitrogen, Carlsbad, CA) was used in place of the poly dT primer.

(5) Primers

Primer sequences were designed against homologous regions of putative target genes with annealing temperatures of 57°-64° C. using the OligoAnalyzer Tool (IDT, Coralville, IA) program. Primers were purchased from IDT.

(6) PCR

PCR reactions were performed in 25 µl reactions containing a final concentration of 1× Phusion® HF buffer, 300 µM each dNTP, 0.3 µM each forward and reverse primer, 0.5 Units 1× Phusion® High-Fidelity DNA Polymerase (ThermoFisher Scientific, Waltham, MA) in a Veriti Thermal Cycler (Applied Biosystems, Carlsbad, CA). General PCR conditions were 98° C. for 2 minutes, followed by 35 cycles of 98° C. for 10 seconds, 55°-62° C. for 30 seconds (depending on primer Ta), and 72° C. for 30 seconds, before a final extension at 72° C. for 10 minutes and a hold at 4° C. PCR products were run on a 1.5% agarose gel and visualized using GelRed® Nucleic Acid Stain (Biotium, Hayward, CA) on an Alpha Imager EC (Alpha Innotech, San Leandro, CA).

(7) Cloning

PCR fragments were cloned using the Zero Blunt TOPO PCR Cloning Kit (Invitrogen, Carlsbad, CA) using 4 µl of PCR product, according to the manufacturer's protocol. The ligated vector was transformed into Top10 One Shot chemically competent cells (Invitrogen, Carlsbad, CA) using the chemical transformation protocol. The transformed E. coli cells were plated onto LB agar plates containing 50 µg/ml kanamycin and the plates were cultured overnight at 37° C.

(8) Colony PCR

Colonies containing recombinant plasmids were screened using PCR with M13 forward and reverse primers. PCR reactions were performed in 15 µl volumes containing 60 mM Tris-SO4 (pH 8.9), 18 mM Ammonium Sulfate, 2.0 mM Magnesium Sulfate, 0.2 mM each dNTP, 0.2 µM each forward and reverse primer, 0.3 Units Platinum Taq Hi Fidelity (Invitrogen, Carlsbad, CA) in a Veriti Thermal Cycler (Applied Biosystems, Carlsbad, CA). Colonies were picked and inoculated into the PCR reaction, followed by an inoculation of 50 µl of LB-kanamycin. The colony PCR conditions were 94° C. for 2 minutes, followed by 35 cycles of 94° C. for 30 seconds, 50° C. for 30 seconds, and 68° C. for 1 minute, before a final extension at 68° C. for 10 minutes and a hold at 4° C. PCR products were run on a 1.5% agarose gel and visualized using GelRed® Nucleic Acid Stain (Biotium, Hayward, CA) on an Alpha Imager EC (Alpha Innotech, San Leandro, CA). Colony PCR reactions producing products of the expected size were sequenced.

(9) Sequencing

Five microliters of each PCR product was prepared for sequencing by enzymatic treatment using 2 µl of High-Throughput ExoSAP-IT (Affymetrix, Santa Clara, CA). Reactions were incubated at 37° C. for 15 minutes, followed by 15 minutes at 80° C. Template was labeled for sequencing using the BigDye Terminator v3.1 Cycle Sequencing Kit (Applied Biosystems, Carlsbad, CA) as follows: 2 µl of the template and 2 µl of a 0.8 µM sequencing primer was added to a mixture of BigDye Terminator sequencing buffer, BigDye Terminator v3.1 Ready Reaction Mix, and water, in a 10 µl reaction. The BigDye sequencing reaction conditions were as follows: 96° C. for 1 minute, followed by 25 cycles of 96° C. for 10 seconds, 50° C. for 5 seconds, and 60° C. for 75 seconds. Unincorporated BigDye terminators were removed using the BigDye XTerminator Purification Kit (Applied Biosystems, Carlsbad, CA). The reactions were sequenced using the Applied Biosystems 3500 Genetic Analyzer (Applied Biosystems, Carlsbad, CA).

(10) Sequence Alignment

Sequence files from the ABI 3500 Genetic Analyzer were imported into Sequencher v4.8 Build 3767 (Gene Codes, Ann Arbor, MI). Vector sequence was trimmed using the Trim Vector tool. Sequences were then automatically aligned and manually edited for sequencing artifacts.

Example 2: Identifying Structural Differences Between Fusarium Wilt (FW)-Resistant Gene(s) and Fusarium Wilt (FW)-Sensitive Gene(s)

In this example, Fusarium Wilt resistance genes were discovered by analysis, as described below, of DNA sequences retrieved from GenBank. Nucleotide sequences from several banana species (i.e. *Musa itinerans, Musa acuminata, Musa basjoo, Musella lasiocarpa, Musa balbisiana*) were downloaded. The *M. itinerans* FusR1 sequence was obtained from multiple accessions (ITC1526, ITC1571, and PT-BA-00223), all of which are FW-resistant. The *M. acuminata* FusR1 sequence labeled 'W-resistant' was obtained from multiple FW-resistant accessions, including ITC0896 (*M. a.* subspecies *banksii*) and PT BA-00281 (Pisang Bangkahulu). The *M. acuminata* sequence labeled 'sensitive' is from the FW-sensitive accessions (ITC0507, ITC0685, PT-BA-00304, PT-BA-00310, and PT-BA-00315). These accessions include multiple samples from banana cultivars such as Pisang Madu, Pisang Pipit, and Pisang Rojo Uter, all of which have been well-characterized as FW-sensitive (Chen et al, 2019). The *M. balbisiana* sequence was obtained from several FW-sensitive accessions, including ITC1016, ITC0545, ITC0080, and ITC0565. FusR1 from *M. basjoo* is from FW-resistant accessions (ITC0061 and PD #3064). Automated bioinformatics analysis was then applied to each pairwise comparison and only those sequences that contain a nucleotide change (or changes) that yield evolutionarily significant change(s) were retained for further analysis. This enabled the identification of genes that have evolved to confer some evolutionary advantage as well as the identification of the specific evolved changes.

Any of several different molecular evolution analyses or Ka/Ks-type methods can be employed to evaluate quantitatively and qualitatively the evolutionary significance of the identified nucleotide changes between homologous gene sequences from related species (Kreitman and Akashi, 1995; Li, 1997). For example, positive selection on proteins (i.e., molecular-level adaptive evolution) can be detected in protein-coding genes by pairwise comparisons of the ratios of nonsynonymous nucleotide substitutions per nonsynonymous site (Ka) to synonymous substitutions per synonymous site (Ks) (Li et al., 1985; Li, 1993). Any comparison of Ka and Ks may be used, although it is particularly convenient and most effective to compare these two variables as a ratio. Sequences are identified by exhibiting a statistically significant difference between Ka and Ks using standard statistical methods.

In some aspects, the Ka/Ks analysis by Li et al. (1993) is used to carry out the present disclosure, although other analysis programs that can detect positively selected genes between species can also be used (Li et al. 1985; Li, 1993; Messier and Stewart, 1997; Nei, 1987).

The Ka/Ks method, which comprises a comparison of the rate of non-synonymous substitutions per non-synonymous site with the rate of synonymous substitutions per synonymous site between homologous protein-coding regions of genes in terms of a ratio, is used to identify sequence substitutions that may be driven by adaptive selection as opposed to neutral substitutions during evolution. A synonymous ('silent') substitution is one that, owing to the degeneracy of the genetic code, makes no change to the amino acid sequence encoded; a non-synonymous substitution results in an amino acid replacement. The extent of each type of change can be estimated as Ka and Ks, respectively, the numbers of synonymous substitutions per synonymous site and non-synonymous substitutions per non-synonymous site. Calculations of Ka/Ks may be performed manually or by using software. An example of suitable programs are Li93 (Li, 1993), or MEGA X: Molecular Evolutionary Genetics Analysis Across Computing Platforms (Kumar et al., 2018)

For the purpose of estimating Ka and Ks, either complete or partial protein-coding sequences are used to calculate total numbers of synonymous and non-synonymous substitutions, as well as non-synonymous and synonymous sites. The length of the polynucleotide sequence analyzed can be any appropriate length. Preferably, the entire coding sequence is compared in order to determine any and all significant changes. Publicly available computer programs, such as Li93 (Li, 1993), or MEGA X: Molecular Evolutionary Genetics Analysis Across Computing Platforms (Kumar et al., 2018) can be used to calculate the Ka and Ks values for all pairwise comparisons.

This analysis can be further adapted to examine sequences in a "sliding window' fashion such that small numbers of important changes are not masked by the whole sequence. "Sliding window' refers to examination of consecutive, overlapping subsections of the gene (the subsections can be of any length).

The comparison of non-synonymous and synonymous substitution rates is commonly represented by the Ka/Ks ratio. Ka/Ks has been shown to be a reflection of the degree to which adaptive evolution has been at work in the sequence under study. Full length or partial segments of a coding sequence can be used for the Ka/Ks analysis. The higher the Ka/Ks ratio, the more likely that a sequence has undergone adaptive evolution and the non-synonymous substitutions are evolutionarily significant. See, for example, Messier and Stewart (1997).

Ka/Ks ratios significantly greater than one (1.0) strongly suggest that positive selection has fixed greater numbers of amino acid replacements than can be expected as a result of chance alone and is in contrast to the most commonly observed pattern in which the ratio is less than or equal to one (Nei, 1987; Hughes and Nei, 1988; Messier and Stewart, 1994; Kreitman and Akashi, 1995; Messier and Stewart, 1997). Ratios less than one generally signify the role of negative, or purifying selection indicating that there is strong pressure on the primary structure of functional, effective proteins to remain unchanged.

All methods for calculating Ka/Ks ratios are based on a pairwise comparison of the number of nonsynonymous substitutions per nonsynonymous site to the number of synonymous substitutions per synonymous site for the protein-coding regions of homologous genes from related species. Each method implements different corrections for estimating "multiple hits" (i.e., more than one nucleotide substitution at the same site). Each method also uses different models for how DNA sequences change over evolutionary time. Thus, preferably, a combination of results from different algorithms is used to increase the level of sensitivity for detection of positively-selected genes and confidence in the result.

It is understood that the methods described herein could lead to the identification of banana polynucleotide sequences that are functionally related to banana protein coding sequences. Such sequences may include, but are not limited to, non-coding sequences or coding sequences that do not encode proteins. These related sequences can be, for example, physically adjacent to the banana protein-coding sequences in the banana genome, such as introns or 5'- and 3'-flanking sequences (including control elements such as promoters and enhancers). These related sequences may be obtained via searching a public genome database such as GenBank or, alternatively, by screening and sequencing an appropriate genomic library with a protein-coding sequence as a probe.

After candidate genes were identified, the nucleotide sequences of the genes in each orthologous gene pair were carefully verified by standard DNA sequencing techniques and then Ka/Ks analysis was repeated for each carefully sequenced candidate gene pair. More specifically, the software ran through all possible pairwise comparisons between putative orthologs of every gene from cultivated banana, *Musa acuminata* (AAA subgr. Cavendish) compared to the orthologs from the wild species, looking for high Ka/Ks ratios. The software BLASTed (in automated fashion) every mRNA sequence from cultivated banana against every sequence in the transcriptome that was sequenced from a wild relative, for example, *M. balbisiana*. The software then performed Ka/Ks analysis for each gene pair (i.e., each set of orthologs), flagging the gene pairs with high Ka/Ks scores.

The software then compared every cultivated banana sequence against every sequence of another wild relative, for example, *M. basjoo*, again by doing a series of BLASTs and then sifting through for high Ka/Ks scores. It thus does this for the transcriptome sequence of all the wild species in succession. This gives a set of candidates (see below) for subsequent analysis. The software next compared every gene sequence in the transcriptome of *M. balbisiana* against every sequence of *M. basjoo*, again by doing a series of BLASTs, and then sifting through for high Ka/Ks scores. It thus ultimately compared all of the expressed genes represented in the utilized cDNA libraries of every banana species against all the genes of every other banana species, both wild and cultivated, with the goal of finding every gene that shows evidence of positive selection.

The flagged gene pairs that emerged were then individually and carefully re-sequenced in the lab to check the accuracy of the original high-throughput reads to eliminate false positives.

Next, every remaining candidate gene pair with a high Ka/Ks score was examined to determine if the comparison was truly orthologous or just an artifactual false positive caused by a paralogous comparison.

Using the methodology described above, banana gene sequences available in GenBank were analyzed to identify a positively-selected gene that has not been linked to FW-resistance trait in banana species in the art. Inventor identified and selected this gene to be expected to give rise to FW-resistance and then named it as *Fusarium* Resistance 1 (FusR1). Remarkably, inventor found an unusually high Ka/Ks ratio of 3.6 between the FusR1 ortholog from the highly resistant wild banana relative *M. itinerans* and FusR1 from FW-sensitive Cavendish (*M. acuminata*).

Inventor obtained accessions of a number of types of bananas, including both banana cultivars and landraces, as well as wild (undomesticated) banana species from the genera *Musa, Musella*, and *Ensete*. These three genera comprise the banana family Musaceae. Inventor made substantial efforts to obtain multiple samples of both *Musa acuminata* ("A"-genome) and *M. balbisiana* ("B"-genome) accessions, in order to adequately sample both the taxonomic and geographic diversity of bananas. Inventor obtained accessions of most of the *acuminata* subspecies. In addition, for outgroup analysis, inventor obtained plant accessions from plant families known to be closely related to Musaceae.

It is well recognized that some B-group banana species/varieties are highly susceptible to Foc-TR4 (Chen et al., 2019), even while sometimes displaying desirable agronomic traits such as drought tolerance. The bananas of the A-genome display a range of *Fusarium*-resistance, tolerance, and sensitivity, depending upon the particular species or cultivated variety. As a consequence, many wild banana species and cultivated banana varieties have been carefully and rigorously characterized for resistance, tolerance, or sensitivity to TR4 (Li et al., 2012, Ssali et al., 2013, Li et al., 2015, Wu et al., 2016, Ribeiro et al., 2018, Niu et al., 2018, and Zuo et al. 2018).

Whenever possible inventor chose to prepare both RNA (for conversion to cDNA) and genomic DNA (gDNA). Most accessions were obtained as either fresh, frozen, or lyophilized samples, and this usually permitted successful RNA extraction. For some samples, particularly when older or partially degraded, only gDNA could be isolated. mRNA sequences and/or coding sequence only), intron sequence, and some sequences (see Sequence Listing) for a number of *Musa, Musella, Ensete*, and outgroup species are provided herewith as described in Table 1 and in the sequence listings. Detailed descriptions of the methods are given in Methods and Materials section of Example 1.

Cultivated bananas are the product of hybridization events between B-genome bananas (the *Musa balbisiana* group) and A-genome bananas (the *M. acuminata* group). It is well recognized that some B-group banana species/varieties are susceptible to Foc-TR4 (Chen et al., 2019), even while sometimes possessing desirable agronomic traits such as drought tolerance (REF). In contrast, the bananas of the A-genome display a range of *Fusarium*-resistance, tolerance, and sensitivity, depending upon the particular species or cultivated variety. Some A-genome group species, such as *Musa itinerans* and *M. basjoo*, have been shown to be extremely resistant to Foc-TR4 (Li et al., 2015; Wu et al., 2016), while some A-genome cultivars like Cavendish are exquisitely sensitive to *Fusarium*.

Analysis of these sequences revealed an important result; which is that all "A"-genome banana species (or cultivated banana varieties) that have been characterized as *Fusarium*-resistant share FusR1 sequences that fall into a common group, while *Fusarium*-sensitive banana species/varieties fall into a different group. Strikingly, every B-genome accession inventor examined is 'FW-sensitive', and all the FusR1 sequences from B-genome accessions are broken and/or damaged in some fashion with some combination of coding-sequence base pair deletions. Often the deletion is either long in size such as 82 or 85 bp, however inventor also found a consistent single base deletion. These deletions alter the inferred protein sequence by destroying reading frame, usually resulting in a truncated protein. In addition, all B-genome FusR1 coding sequences contain an unspliced 84 bp intron, often appearing together with the 85-bp deletion.

As to A-genome bananas, inventor found that A-genome accessions that are known to be Foc-TR4 resistant all share a common FusR1 sequence group, while Foc-TR4-sensitive A-genome accessions all share a different FusR1 sequence group.

This is strong evidence that FusR1 is responsible for the observed disease-resistance patterns between *Fusarium*-resistant vs. *Fusarium*-sensitive species. The analyses in this example suggest that differing resistance from sensitivity to *Fusarium* race 4 is strongly linked with FusR1 sequence differences.

Further support for this comes from our examination of the few banana species that have been characterized as 'Fusarium Wilt-tolerant'. These species all have FusR1 sequences that fall into a third sequence group, all are intermediate between the *Fusarium*-resistant and *Fusarium*-sensitive sequence groups.

The banana industry was forced in the 1950s to convert from its primary cultivar, Gros Michel, to the Cavendish cultivar when *Fusarium* (Panama Disease) race 1 posed a critical threat to Gros Michel. Cavendish, which is a half-sib to Gros Michel (both are "A" genome species), was found to be resistant to race 1. Thus, the closely related Cavendish and Gros Michel cultivars show differing profiles of resistance to the various *Fusarium* races. (Both are sensitive to Foc-TR4, the current threat to the banana industry.)

Inventor sequenced FusR1 from a number of *Musa acuminata* accessions. In each case, inventor cloned, as described in Example 1, the FusR1 gene and then sequenced multiple clones of the FusR1 gene. Some of these *M. acuminata* accessions have been well-characterized for Fusarium Wilt resistance/sensitivity. Inventor found three alleles for *M. acuminata* FusR1. The critical observation is that all Fusarium Wilt-resistant accessions share similar FusR1 sequences. The two FusR1 alleles from FW-resistant *M. acuminata* accessions are the Fusarium Wilt-resistant FusR1 allele or simply, the "Resistant Alleles" (SEQ ID NO: 8 and SEQ ID NO: 10). In contrast, all FW-sensitive *M. acuminata* accessions share a different allele, named the Fusarium Wilt Sensitive FusR1 Allele (SEQ ID NO: 13). The FW-resistant FusR1 alleles differ in just a few critical nucleotide substitutions from the FW-sensitive allele. (See FIG. 1). This strongly suggests that Fusarium Wilt resistance/sensitivity is controlled by the particular FusR1 allele that a banana plant carries.

Example 3: Resistance Breeding of Banana

Tetraploid versions of FW-sensitive Cavendish cultivars (*M. acuminata*; AAAA) are available or can be developed via large pollination/breeding programs focused on creating, identifying and isolating the relatively low percentage of tetraploid progeny that are produced (e.g., Aguilar Moran, J. F., 2013, Improvement of Cavendish Banana cultivars through conventional breeding, Acta Hortic. 986:205-208; Jenny et al., In Jacome et al., editors, *Mycosphaerella* leaf spot diseases of banana: present status and outlook, Proceedings of the 2$^{nd}$ International Workshop on *Mycosphaerella* leaf spot diseases held in San Jose, Costa Rica, 20-23 May 2002, Session 4, pages 199-208) or by subjecting diploid AA genotypes to in vitro polyploidization (Amah et al., November 2019, Frontiers in Plant Science, Vol. 10, Article 1450, 12 pages).

Diploid versions of FW-resistant FusR1 (AA) of *M. acuminata* ssp. *banksia* can be identified or developed using methods known to those skilled in the art (e.g., Bakry et al., Chapter 1, Genetic Improvement in Banana, 50 pages, In Breeding Plantation Tree Crops: Tropical Species, 2009). The resultant diploids are screened for the presence of SEQ ID NO: 8 and/or SEQ ID NO: 10 (mRNA sequences).

A tetraploid FW-sensitive Cavendish plant, such as a tetraploid of the 'Naine' or 'Williams' cultivar, can be used a male parent in crosses with a diploid FW-resistant FusR1 *M. acuminata* ssp. *Banksia* plant, such as a diploid 'ITC0896,' used as the female parent.

A large number of the resultant progeny are screened for triploid plants (AAA) comprising SEQ ID NO: 8 and/or SEQ ID NO: 10 (mRNA sequences) and subsequently evaluated for agronomic traits.

All resulting/selected banana plants with resistance to TR4 can be maintained via asexual reproduction and used for production or in subsequent breeding programs.

Example 4: Materials and Methods for Plant Transformation

Banana transformation systems will use sterile material of selected banana strains. *A* variety of tissue culture and transformation methodologies will be used to increase the likelihood of success. See, for example, the transformation protocols described in Ploetz (2015, Phytopathology 105: 1512-1521), U.S. Pat. Nos. 7,534,930; 6,133,035; Sagi et al., Bio/Technology 13, 481-485, 1995; May et al., Bio/Technology 13, 485-492, 1995; Vishnevetsky et al., Transgenic Res. 20(1):61-71, 2011; Paul et al. (2011); Zhong et al., Plant Physiol. 110, 1097-1107, 1996; Dugdale et al., Journal of General Virology 79:2301-2311, 1998; Mohan and Swennen (editors), 2004, Banana improvement: cellular, molecular biology, and induced mutations, Science Publishers, Inc.; and, Remy et al., 2013, Genetically modified bananas: Past, present and future, Acta Horticulturae 974:71-80, each of which is expressly incorporated herein by reference in their entireties.

These methodologies will focus on tissue culture conditions, identifying different tissue types for regeneration/shooting, media formulations, *agrobacterium* strains, selection cassettes, constructing control and delivery vectors, gene delivery, selectable markers, and target tissue/cell substrates for DNA delivery and transformation. Initial experiments will deploy control vectors using visual markers and selection cassettes to rapidly optimize experimental direction and screen potential transgenic events. Parallel experiments will be directed at optimizing transformation efficiency and using genes of interest (GOI).

Modifications to media formulations, vectors, and transformation processes will be done to improve process and transformation efficiency. Transformation vectors that contain key genes of interest will continue to be transformed to produce additional overexpression or knock-out events. Vectors to be used as necessary include but are not limited to multi-gene stacked vectors, polycistronic gene vectors, and multi gRNA CRISPR editing vectors for testing efficacy in banana. Testing will be done on TO events to show presence and copy number of the selectable marker gene or the GOI. In addition, mRNA expression analysis will be used as needed for any key GOIs. Putative transformed plant material will be used for subsequent testing or analysis.

CRISPR technologies are described in detail elsewhere herein, including references to the compositions and procedures for using CRISPR to edit plant genomes, such as the banana genome. Detailed compositions and procedures for utilizing CRISPR to knock-out a gene in plants that gives rise to a phenotype of interest (e.g., resistance to fungal pathogens such as *Fusarium*) are provided in WO 2019/118342 (PCT/US2018/064735), WO 2018/220581 (PCT/IB2018/053903) and US 2019/0032070 (U.S. Ser. No. 16/072,706), each of which is specifically and entirely incorporated by reference herein.

Once target sites for knocking out a candidate gene (e.g. endogenous FW-sensitive FusR1 gene(s)) are screened in silico and selected, CRISPR/Cas9 vectors for the targeted mutation(s) in the candidate gene found in plants of interest will be constructed for the transformation of the vectors into the plant of interest (i.e. FW-sensitive banana varieties, such as the widely-grown triploid, sterile Cavendish variety and its progeny).

The CRISPR/Cas9 vectors will be transformed into plants of interest such as banana varieties, especially FW-sensitive bananas using *agrobacterium*-mediated protocols that are known in the art (see for example, Ma et al., 2015) and/or developed or refined by inventor. Tissue culture and regeneration of transformed plants will be performed accordingly.

The transformed plants with the CRISPR/Cas9 vectors will be regenerated and tested to verify the introduction of CRISPR/Cas9 vectors into the plant cells of interest. As a control for the induction of indels, a construct expressing wild-type Cas9 will also be used in this experiment.

The knock-out of the candidate gene(s) will be examined in all transformed plants. The knock-out will be studied by (1) quantitative PCR to check suppression and/or silencing of the candidate gene or (2) PCR amplification and subsequent Sanger sequencing and/or high-throughput deep sequencing. Also, the amino acid substitution(s) caused by the introduced frame-shift to the target genome region will be analyzed by protein sequencing with mass spectrometry.

The transformed plants obtained will be grown in the controlled green house and/or field conditions. The transformed plants, verified with amino acid insertion, deletion, or substitution of interest, will be observed for enhanced resistance to FW, Panama Disease, or infection by *Fusarium oxysporum* f. sp. *cubense* Tropical Race 4.

Example 5: Banana Transformation

Banana plants susceptible to *Fusarium oxysporum* race 4 (aka Tropical Race 4 or TR4) can be transformed into TR4-resistant plants by transforming them with a nucleotide sequence coding for resistance using the banana transformation technologies provided in Example 4 and the FusR1 nucleotide sequences coding for TR4 resistance as provided herein. For example, a TR4-susceptible Cavendish banana cultivar can be transformed with one of the FusR1 alleles coding for TR4-resistance as provided herein. As a further example, a TR4-susceptible Cavendish banana cultivar can be transformed with one or more of the following nucleotide coding sequences coding for TR4 resistance: SEQ ID NO: 2, SEQ ID NO: 5, SEQ ID NO: 9 SEQ ID NO: 11, SEQ ID NO:18, SEQ ID NO: 21, and/or SEQ ID NO:24.

For example, the Cavendish banana cultivar 'Grand Nain' (AAA) can be transformed with SEQ ID NO 2, SEQ ID NO 5, SEQ ID NO 9 and/or SEQ ID NO 11 using the transformation protocols set forth in U.S. Pat. No. 7,534,930 ('Transgenic Disease Resistant Banana'), which is incorporated herein in its entirety for everything it discloses.

In summary, immature male flowers of a Cavendish banana cultivar, such 'Grand Nain' or 'Williams,' are used to produce embryogenic calli. A nucleic acid construct comprising SEQ ID NO: 2, SEQ ID NO: 5, SEQ ID NO: 9, SEQ ID NO 11, SEQ ID NO:18, SEQ ID NO: 21, and/or SEQ ID NO:24, operably linked to a 35S promoter sequence is constructed. Or, alternatively, the promoter sequence of the FW-resistant allele 1 of FusR1 from *M. acuminata* (SEQ ID NO 31) could be used to drive expression of the resistance alleles. This construct is introduced into the embryogenic calli using microprojectile bombardment. Bombarded plantlets are regenerated from the embryogenic calli and the plantlets undergo PCR analyses to determine which plantlets were transformed with the TR4-resistance gene(s). Tissue culture extracts from the resulting plants which positively express the TR4-resistance gene(s) are tested for their ability to suppress growth of TR4. In addition, the putative transformed plants are tested for resistance to TR4. TR4 resistant plants are isolated and cloned. The TR4 resistant plants can be used in breeding programs to transfer the resistant genes as set forth in Example 3.

Where a transformed plant expresses SEQ ID NO 2 or SEQ ID NO 5; and, also expresses SEQ ID NO: 9 or SEQ ID NO: 11, that transformed plant would have stacked resistance genes to TR4 given it comprises two different nucleic acids coding for TR4 resistance. As discussed above and presented in Table 1, SEQ ID NO: 2 and SEQ ID NO: 5 are FusR1 allele 1 and allele 2 coding sequences, respectively, coding for resistance as obtained from *M. itinerans*. In contrast, SEQ ID NO: 9 and SEQ ID NO: 11 are FusR1 allele 1 and allele 2 coding sequences, respectively, coding for resistance obtained from *M. acuminata* ssp. *banksia*. Thus, a transformed plant expressing both types of resistance genes would have stacked, or pyramidal, resistance to Panama Disease Tropical Race 4.

All resulting/selected banana plants with resistance to TR4 can be maintained via asexual reproduction and used for production or in subsequent breeding programs.

Example 6: Banana Transformation Starting with a Cultivar Comprising Resistance

Transformed banana plants resistant to Panama Disease Tropical Race 4 can be produced using the procedures outlined in Example 5 where the initial, untransformed plant also has resistance to TR4 and/or to one or more additional diseases. In this way the resultant transformed plant can have multiple, or stacked, resistance genes. For example, the starting cultivar used in the transformation procedures of Example 5 can be a Cavenish cultivar with the resistance gene RGA2 (Dale et al., 2017). Thus, a Cavendish cultivar comprising the RGA2 coding sequence can be transformed to express SEQ ID NO: 2, SEQ ID NO: 5, SEQ ID NO: 9 and/or SEQ ID NO: 11, SEQ ID NO:18, SEQ ID NO: 21, and/or SEQ ID NO:24 and thereby have stacked resistance genes to TR4.

All resulting/selected banana plants with resistance to TR4 can be maintained via asexual reproduction and used for production or in subsequent breeding programs.

Example 7: Knocking Out Expression of FusR1-Susceptibility Genes

In addition to or, alternatively instead of, transforming the plants according to Example 5 or Example 6, the nucleotide sequences of FusR1 alleles coding for susceptibility to TR4 in *M. acuminata* (e.g., SEQ ID NO: 14) can be knocked-out using a TALEN, a meganuclease, a zinc finger nuclease, a CRISPR-associated nuclease or other appropriate gene editing tools.

In one such method, a guide RNA may be utilized along with an appropriate CRISPR-associated nuclease, including wherein the guide RNA comprises a variable targeting domain that is complementary to all or a partial sequence of SEQ ID NO: 14. For example, a double-strand break can be introduced into an endogenous sequence coding for a FW-sensitive FusR1 allele in *M. acuminata* (SEQ ID NO: 14) in a banana cell using a modified SEQ ID NO: 14, wherein the modified SEQ ID NO 14 comprises a nucleic acid alteration that knocks out the gene function of SEQ ID NO: 14.

For details on how to construct and use such a CRISPR-associated nuclease and Guide RNA in plants, see, for example, U.S. Patent Application Publication No. 2019/0032070 A1 and WO 2019/118342 A1, each of which is incorporated by reference in its entirety. For using CRISPR as a gene editing tool in banana, including to silence disease susceptibility genes, see, for example, WO 2018/220581 A1 (Compositions and Methods for Increasing Shelf-Life of Banana); Tripahi et al., 2019, CRISPR/Cas9 editing of endogenous banana streak virus in the B genome of *Musa* spp. overcomes a major challenge in banana breeding, Communications Biology 2, Article 46, 11 pages; and, Ntui et al., January 2020, Robust CRISPR/Cas9 mediated genome editing tool for banana and plantain (*Musa* spp.), Vol. 21, 10 pages.

The modified plant cell can be generated/regenerated into a banana plant which can be maintained via asexual reproduction.

All resulting/selected banana plants with the knock out for susceptibility to TR4 can be maintained via asexual reproduction and used for production or in subsequent breeding programs.

Example 8: Gene Editing of Bananas Susceptible to TR4

Banana plants susceptible to *Fusarium oxysporum* race 4 (aka Tropical Race 4 or TR4) can be modified into TR4- resistant plants by using gene targeting/gene editing tools to change their endogenous nucleic acid sequences coding for susceptibility into nucleotide sequences coding for resistance using the banana gene editing technologies provided in Example 4 and the FusR1 nucleotide sequences coding for TR4 resistance as provided herein. For example, the endogenous nucleic acid sequence coding for TR4-susceptibility in a Cavendish banana cultivar can be altered based on the nucleic acid sequence of one of the FusR1 alleles coding for TR4-resistance as provided herein. As a further example, the nucleic acid sequence coding for TR4-susceptibility in a Cavendish banana cultivar can be altered based on one or more of the following nucleotide coding sequences coding for TR4 resistance: SEQ ID NO 2, SEQ ID NO 5, SEQ ID NO 9, SEQ ID NO 11, SEQ ID NO:18, SEQ ID NO: 21, and/or SEQ ID NO:24.

For example, the Cavendish banana cultivar 'Grand Nain' (AAA) can be modified based on the nucleic acid sequences coding for resistance to TR4 as set forth herein (i.e., based upon SEQ ID NO 2, SEQ ID NO 5, SEQ ID NO 9, SEQ ID NO 11, SEQ ID NO:18, SEQ ID NO: 21, and/or SEQ ID NO:24) using modern gene editing tools. See FIG. 1.

In some general examples, the endogenous FW-susceptibility FusR1 gene of SEQ ID NO 14 is modified by one or more of the following changes based on its alignment with FW-resistant FusR1 genes of SEQ ID NO 2, SEQ ID NO 5, SEQ ID NO, SEQ ID NO 11, SEQ ID NO:18, SEQ ID NO: 21, and/or SEQ ID NO:24. See FIG. 1.

In some specific examples, SEQ ID NO 14 is modified by the following changes based on its alignment with SEQ ID NO 9 (see sequence alignment, FIG. 1): the T corresponding to position 148 is replaced with G (148T>G); the T corresponding to position 323 is replaced with A (323T>A); the G corresponding to position 344 is replaced with C (344G>C); and/or, the A corresponding to position 347 is replaced with T (347A>T). In one example, the only substitution made is 344G>C. In one example, the following three substitutions are made: 323T>A, 344G>C and 347A>T. In yet another example, all four substitutions are made: 148T>G, 323T>A, 344G>C and 347A>T. See FIG. 1.

In some general examples, any and all nucleic acid substitutions are made to the nucleic acid sequences coding for FW-susceptible FUSR1 proteins so that the resulting, modified nucleic acids code for FW-resistant FUSR1 proteins. See FIG. 1 and FIG. 2.

In some specific examples, the endogenous nucleic acid sequence coding for the FW-susceptible FUSR1 protein of SEQ ID NO: 15 is modified by one or more nucleic acid changes based on its alignment with FW-resistant FUSR1 protein of SEQ ID NO: 12 to produce the following protein changes: the Leucine corresponding to position 50 is replaced with Valine (50L>V); the Valine corresponding to position 108 is replaced with Glutamic Acid (108V>E); the Arginine at position 115 is replaced with Proline (115R>P); and/or, the Aspartic Acid at position 116 is replaced with Valine (116D>V). In one example, the only protein substitution that is made is 115R>P. In another example, the only protein substitutions that are made are 108V>E, 115R>P and 116D>V. In yet another example, all four protein substitutions are made: 50L>V, 108V>E, 115R>P and 116D>V. See FIG. 2.

The banana-specific gene editing protocols from the following publications provide the protocols for making the necessary nucleotide base pair substitutions in banana: Shao et al., 2020, Using CRISPR/Cas9 genome editing system to create MaGA20ox2 gene-modified semi-dwarf banana, Plant Biotechnology Journal, 18:17-19; Kaur et al., 2017, CRISPR/Cas9-mediated efficient editing in phytoene desaturase (PDS) demonstrates precise manipulation in banana cv. Rasthali genome, Functional & Integrative Genomics, 18(1):89-99; Otang et al., 2020, Robust CRISPR/Cas9 mediated genome editing tool for banana and plantain (*Musa* spp.), Current Plant Biology, 21, 10 pages; Tripathi et al., 2019, CRISPR/Cas9 editing of endogenous banana streak virus in the B genome of *Musa* spp. Overcomes a major challenge in banana breeding, Communications Biology, 2:46, 11 pages; and, U.S. Pat. No. 7,381,556, each of which is entirely incorporated by reference herein for everything it teaches.

In summary, immature male flowers of a Cavendish banana cultivar, such 'Grand Nain' or 'Williams,' is used to produce embryogenic calli and/or an embryogenic cell suspension. A CRISPR/Cas9 construct is prepared following the procedures outline in any one or more of the above-listed scientific and patent publications, wherein the construct is constructed based upon the sequence alignments provided in FIG. 1. The construct is delivered into the embryogenic calli or embryogenic cell suspension and well-rooted plantlets are generated. Random regenerates are selected and screened for the presence of the Cas9 gene by PCR using primers. The well-rooted plantlets of Cas9 PCR-positive events and control plants are acclimatized and potted in the greenhouse. Molecular analyses are conducted to confirm gene editing in the endogenous FusR1 genes.

The genome edited plants and the control plants are evaluated for agronomic traits and evaluated for TR4 resistance. The resulting gene-edited plants which positively express the TR4-resistance protein(s) and display resistance to TR4 are cloned. The gene-edited TR4 resistant plants can be used in breeding programs to transfer the resistant genes as set forth in Example 3.

All resulting/selected banana plants with resistance to TR4 can be maintained via asexual reproduction and used for production or in subsequent breeding programs.

Further Numbered Embodiments of the Disclosure

Other subject matter contemplated by the present invention is set out in the following numbered embodiments:

1. An isolated nucleic acid molecule comprising nucleic acid sequence SEQ ID NO: 14 coding for susceptibility to *Fusarium oxysporum* race 4 when expressed in a plant, wherein SEQ ID NO: 14 is modified by one, two, three or four nucleic acid substitutions so that the resulting nucleic acid sequence codes for resistance to *Fusarium oxysporum* race 4 when expressed in a plant.
2. The isolated nucleic acid molecule of embodiment 1, wherein the nucleic acid substitutions comprise replacing a T corresponding to position 148 of SEQ ID NO: 14 with a G (148T>G).
3. The isolated nucleic acid molecule of embodiment 1, wherein the nucleic acid substitutions comprise replacing a T corresponding to position 323 of SEQ ID NO: 14 with an A (323T>A).
4. The isolated nucleic acid molecule of embodiment 1, wherein the nucleic acid substitutions comprise replacing a G corresponding to position 344 of SEQ ID NO: 14 with a C (344G>C).
5. The isolated nucleic acid molecule of embodiment 1, wherein the nucleic acid substitutions comprise replacing an A corresponding to position 347 of SEQ ID NO: 14 with a T (347A>T).
6. The isolated nucleic acid molecule of embodiment 1, wherein the nucleic acid substitutions comprise replacing a T corresponding to position 323 with an A (323T>A), replacing a G corresponding to position 344 with a C (344G>C), and replacing an A corresponding to position 347 with a T (347A>T), and wherein all positions are based on SEQ ID NO: 14.

7. The isolated nucleic acid molecule of embodiment 1, wherein SEQ ID NO: 14 codes for an amino acid sequence of SEQ ID NO: 15 and wherein the nucleic acid substitutions result in replacing a Leucine corresponding to position 50 of SEQ ID NO: 15 with a Valine (50L>V).

8. The isolated nucleic acid molecule of embodiment 1, wherein SEQ ID NO: 14 codes for an amino acid sequence of SEQ ID NO: 15 and wherein the nucleic acid substitutions result in replacing a Valine corresponding to position 108 of SEQ ID NO: 15 with a Glutamic Acid (108V>E).

9. The isolated nucleic acid molecule of embodiment 1, wherein SEQ ID NO: 14 codes for an amino acid sequence of SEQ ID NO: 15 and wherein the nucleic acid substitutions result in replacing an Arginine corresponding to position 115 of SEQ ID NO: 15 with a Proline (115R>P).

10. The isolated nucleic acid molecule of embodiment 1, wherein SEQ ID NO: 14 codes for an amino acid sequence of SEQ ID NO: 15 and wherein the nucleic acid substitutions result in replacing an Aspartic Acid corresponding to position 116 of SEQ ID NO: 15 with a Valine (116D>V).

11. The isolated nucleic acid molecule of embodiment 1, wherein SEQ ID NO: 14 codes for an amino acid sequence of SEQ ID NO: 15 and wherein the nucleic acid substitutions result in replacing a Valine corresponding to position 108 of SEQ ID NO: 15 with a Glutamic Acid (108V>E), an Arginine corresponding to position 115 of SEQ ID NO: 15 with a Proline (115R>P), and an Aspartic Acid corresponding to position 116 of SEQ ID NO: 15 with a Valine (116D>V).

12. The isolated nucleic acid molecule of embodiments 1-11, wherein the expression occurs in a plant cell, plant tissue, plant cell culture, plant tissue culture, or whole plant.

13. The isolated nucleic acid molecule of embodiment 12, wherein the expression occurs in a *Musa* cell, tissue, cell culture, tissue culture, or whole plant.

14. The isolated nucleic acid molecule of embodiment 13, wherein the expression occurs in a *Musa acuminata* cell, tissue, cell culture, tissue culture or whole plant.

15. A nucleic acid construct comprising the isolated nucleic acid molecule of embodiments 1-11, wherein the nucleic acid sequence is operably linked to a promoter capable of driving expression of the nucleic acid sequence.

16. The nucleic acid construct of embodiment 15, wherein the promoter is a plant promoter.

17. The nucleic acid construct of embodiment 15, wherein the promoter is a 35S promoter.

18. The nucleic acid construct of embodiment 15, wherein the promoter is coded by SEQ ID NO: 31.

19. A transformation vector comprising the nucleic acid construct of embodiments 15-18.

20. A method of transforming a plant cell comprising introducing the transformation vector of embodiment 19 into a plant cell, whereby the transformed plant cell expresses the nucleic acid sequence coding for resistance to *Fusarium oxysporum* race 4.

21. The method of embodiment 20, wherein the plant cell is a *Musa* plant cell.

22. The method of embodiment 20, wherein the plant cell is a *Musa acuminata* plant cell.

23. The method of embodiments 20-22 further comprising producing transformed plant tissue from the transformed plant cell.

24. The method of embodiment 23 further comprising producing a transformed plantlet from the transformed plant tissue.

25. The method of embodiment 24 further comprising producing a clone of the transformed plantlet.

26. The method of embodiments 24 or 25 further comprising growing the transformed plantlet or clone of the transformed plantlet into a mature transformed plant.

27. The method of embodiment 26, wherein the mature transformed plant is a *Musa* plant and the mature transformed *Musa* plant is capable of producing fruit.

28. The method of embodiment 27 further comprising producing clones of the mature transformed *Musa* plant.

29. The method of embodiment 27 or 28 further comprising using the mature transformed *Musa* plant or clone of the mature transformed *Musa* plant in a breeding method.

30. An isolated amino acid molecule comprising an amino acid sequence of SEQ ID NO: 15 coding for a protein that when produced in a plant results in susceptibility to *Fusarium oxysporum* race 4, wherein SEQ ID NO: 15 is modified by one, two, three or four amino acid substitutions so that it codes for a protein which when produced in a plant results in resistance to *Fusarium oxysporum* race 4.

31. The isolated amino acid molecule of embodiment 30, wherein the amino acid substitutions comprise replacing a Leucine corresponding to position 50 of SEQ ID NO: 15 with a Valine (50L>V).

32. The isolated amino acid molecule of embodiment 30, wherein the amino acid substitutions comprise replacing a Valine corresponding to position 108 of SEQ ID NO: 15 with a Glutamic Acid (108V>E)

33. The isolated amino acid molecule of embodiment 30, wherein the amino acid substitutions comprise replacing an Arginine corresponding to position 115 of SEQ ID NO: 15 with a Proline (115R>P).

34. The isolated amino acid molecule of embodiment 30, wherein the amino acid substitutions comprise replacing an Aspartic Acid corresponding to position 116 of SEQ ID NO: 15 with a Valine (116D>V).

35. The isolated amino acid molecule of embodiment 30, wherein the amino acid substitutions comprise replacing a Valine corresponding to position 108 of SEQ ID NO: 15 with a Glutamic Acid (108V>E), an Arginine corresponding to position 115 of SEQ ID NO: 15 with a Proline (115R>P), and an Aspartic Acid corresponding to position 116 of SEQ ID NO: 15 with a Valine (116D>V).

36. The isolated amino acid molecule segment of embodiments 30-35, wherein the production occurs in a plant cell, plant tissue, plant cell culture, plant tissue culture, or whole plant.

37. The isolated amino acid molecule segment of embodiment 36, wherein the production occurs in a *Musa* cell, tissue, cell culture, tissue culture, or whole plant.

38. The isolated amino acid molecule segment of embodiment 36, wherein the production occurs in a *Musa acuminata* cell, tissue, cell culture, tissue culture or whole plant.
39. A nucleic acid construct comprising a nucleic acid sequence coding for resistance to *Fusarium oxysporum* race 4 when expressed in a plant, wherein said nucleic acid sequence is selected from the group consisting of SEQ ID NO: 2, SEQ ID NO: 5, SEQ ID NO: 9, SEQ ID NO: 11, SEQ ID NO: 18, SEQ ID NO: 21, and SEQ ID NO: 24, and wherein the nucleic acid sequence is operably linked to a promoter capable of driving expression of the nucleic acid sequence.
40. The nucleic acid construct of embodiment 39, wherein the promoter is a plant promoter.
41. The nucleic acid construct of embodiment 39, wherein the promoter is a 35S promoter.
42. The nucleic acid construct of embodiment 39, wherein the promoter is coded by SEQ ID NO: 31.
43. A transformation vector comprising the nucleic acid construct of embodiments 39-42.
44. A method of transforming a plant cell comprising introducing the transformation vector of embodiment 43 into a plant cell, whereby the transformed plant cell expresses the nucleic acid sequence coding for resistance to *Fusarium oxysporum* race 4.
45. The method of embodiment 44, wherein the plant cell is a *Musa* plant cell.
46. The method of embodiment 44, wherein the plant cell is a *Musa acuminata* plant cell.
47. The method of embodiments 44-46 further comprising producing transformed plant tissue from the transformed plant cell.
48. The method of embodiment 47 further comprising producing a transformed plantlet from the transformed plant tissue.
49. The method of embodiment 48 further comprising producing a clone of the transformed plantlet.
50. The method of embodiments 48 or 49 further comprising growing the transformed plantlet or clone of the transformed plantlet into a mature transformed plant.
51. The method of embodiment 50, wherein the mature transformed plant is a *Musa* plant and the mature transformed *Musa* plant is capable of producing fruit.
52. The method of embodiment 51 further comprising producing clones of the mature transformed *Musa* plant.
53. The method of embodiments 51 or 52 further comprising using the mature transformed *Musa* plant or clone of the mature transformed *Musa* plant in a breeding method.
54. A banana breeding method comprising crossing a first *Musa* plant comprising a nucleic acid sequence coding for resistance to *Fusarium oxysporum* race 4 with a second *Musa* plant that is susceptible to *Fusarium oxysporum* race 4 and selecting resultant progeny of the cross based on their resistance to *Fusarium oxysporum* race 4, wherein said nucleic acid sequence coding for resistance to *Fusarium oxysporum* race 4 is selected from the group consisting of SEQ ID NO: 2, SEQ ID NO: 5, SEQ ID NO: 9, SEQ ID NO: 11, SEQ ID NO: 18, SEQ ID NO: 21, and SEQ ID NO: 24.
55. The banana breeding method of embodiment 54 further comprising producing clones of the resultant progeny of the cross wherein the clones are selected based on their resistance to *Fusarium oxysporum* race 4.
56. The banana breeding method of embodiment 54, wherein the first and second *Musa* plants are from different *Musa* species. The banana breeding method of embodiment 54, wherein the first and second *Musa* plants are from the same *Musa* species. The banana breeding method of embodiment 54, wherein the first and/or second *Musa* plant is a *Musa acuminata* plant.
57. The banana breeding method of embodiment 54, wherein the progeny of the cross that display resistance to *Fusarium oxysporum* race 4 are selected using molecular markers that are designed based on the nucleic acid sequence coding for resistance to *Fusarium oxysporum* race 4 that is present in the first *Musa* plant used in the cross.
58. A method for obtaining a *Musa acuminata* plant cell with a silenced endogenous gene coding for susceptibility to *Fusarium oxysporum* race 4, the method comprising introducing a double-strand break to at least one site in an exogenous gene coded by SEQ ID NO: 14 to produce a *Musa acuminata* plant cell with a silenced endogenous gene coding for susceptibility to *Fusarium oxysporum* race 4.
59. The method of embodiment 58 further comprising generating a *Musa acuminata* plant from the *Musa acuminata* plant cell with a silenced endogenous gene coding for susceptibility to *Fusarium oxysporum* race 4 to produce a *Musa acuminata* plant with a silenced endogenous gene coding for susceptibility to *Fusarium oxysporum* race 4.
60. The method of embodiment 59 further comprising using the *Musa acuminata* plant with a silenced endogenous gene coding for susceptibility to *Fusarium oxysporum* race 4 in a banana breeding program.
61. The method of embodiment 20 or 44, wherein the plant cell is the *Musa acuminata* plant cell of embodiment 59 with a silenced endogenous gene coding for susceptibility to *Fusarium oxysporum* race 4.
62. The method of embodiment 58, wherein the double-strand break is induced by a nuclease selected from the group consisting of a TALEN, a meganuclease, a zinc finger nuclease, and a CRISPR-associated nuclease.
63. The method of claim 62, wherein the double-strand break is induced by a CRISPR-associated nuclease and where a guide RNA is provided.
64. A method for producing a plant cell resistant to *Fusarium oxysporum* race 4 comprising introducing at least one genetic modification into one or more endogenous nucleic acid sequences coding for susceptibility to *Fusarium oxysporum* race 4, wherein the genetic modification confers resistance to *Fusarium oxysporum* race 4 to the plant cell.
65. The method of embodiment 64 wherein the at least one genetic modification is introduced by a TALEN, a meganuclease, a zinc finger nuclease or a CRISPR-associated nuclease.
66. The method of claim 64, wherein the at least one genetic modification is introduced by a CRISPR-associated nuclease and an associated guide RNA.
67. The method of embodiment 64, wherein the at least one genetic modification is selected from the list consisting of replacing a T corresponding to position 148 of SEQ ID NO: 14 with a G (148T>G), replacing a T corresponding to position 323 of SEQ ID NO: 14 with an A (323T>A), replacing a G corresponding to position 344 of SEQ ID NO: 14 with a C (344G>C), and replacing an A corresponding to position 347 of SEQ ID NO: 14 with a T (347A>T).

68. The method of embodiment 64, wherein the at least one genetic modification results in a change in an amino acid selected from the group consisting of replacing a Leucine corresponding to position 50 of SEQ ID NO: 15 with a Valine (50L>V), replacing a Valine corresponding to position 108 of SEQ ID NO: 15 with a Glutamic Acid (108V>E), replacing an Arginine corresponding to position 115 of SEQ ID NO: 15 with a Proline (115R>P), and replacing an Aspartic Acid corresponding to position 116 of SEQ ID NO: 15 with a Valine (116D>V).

69. The method of embodiments 64-68, wherein the plant cell is a *Musa* plant cell.

70. The method of embodiments 64-68, wherein the plant cell is a *Musa acuminata* plant cell.

71. The method of embodiments 64-70 further comprising producing transformed plant tissue from the transformed plant cell.

72. The method of embodiment 71 further comprising producing a transformed plantlet from the transformed plant tissue.

73. The method of embodiment 72 further comprising producing a clone of the transformed plantlet.

74. The method of embodiments 71 or 72 further comprising growing the transformed plantlet or clone of the transformed plantlet into a mature transformed plant.

75. The method of embodiment 74, wherein the mature transformed plant is a *Musa* plant and the mature transformed *Musa* plant is capable of producing fruit.

76. The method of embodiment 75 further comprising producing clones of the mature transformed *Musa* plant.

77. The method of embodiments 75 or 76 further comprising using the mature transformed *Musa* plant or clone of the mature transformed *Musa* plant in a breeding method.

INCORPORATION BY REFERENCE

All references, articles, publications, patents, patent publications, and patent applications cited herein within the above text and/or cited below are incorporated by reference in their entireties for all purposes. However, mention of any reference, article, publication, patent, patent publication, and patent application cited herein is not, and should not be taken as acknowledgment or any form of suggestion that they constitute valid prior art or form part of the common general knowledge in any country in the world.

U.S. PATENT DOCUMENTS 7,534,930 B2 5/2009 Vishnevetsky et al.
6,274,319 8/2001 Messier and Sikela
9,834,783 12/2017 Messier

OTHER PUBLICATIONS

Armenteros, J. J. A. A. 2017. DeepLoc: prediction of protein subcellular localization using deep learning. *Bioinformatics* 33(21): 3387-3395.

Armenteros et al. 2019. SignalP 5.0 improves signal peptide predictions using deep neural networks. *Nat Biotechnol* 37:420-423.

Bai, T-T. et al. 2013. Transcriptome and Expression Profile Analysis of Highly Resistant and Susceptible Banana Roots Challenged with *Fusarium oxysporum* f sp. *cubense* Tropical Race 4. *PLOS|One* Published: Sep. 23, 2013.

Barbosa, J. A. R. G. et al., 2007. Crystal Structure of the Bowman-Birk Inhibitor from *Vigna unguiculata* Seeds in Complex with β-Trypsin at 1.55 Å Resolution and Its Structural Properties in Association with Proteinases. *Biophysical Journal*. 92(5): 1638-1650.

Chen, A., et al. 2019. Assessing Variations in Host Resistance to *Fusarium oxysporum* f sp. *cubense* Race 4 in *Musa* Species, With a Focus on the Subtropical Race 4. *Front. Microbiol.* 10.

Christelová, P. et al. 2017. Molecular and cytological characterization of the global *Musa* germplasm collection provides insights into the treasure of banana diversity. *Biodivers. Conserv.* 26: 801.

Dale, J. et al. 2017. Transgenic Cavendish bananas with resistance to Fusarium wilt tropical race 4. *Nature Communications*. 8: Article number 1496.

Davey, M. W. et al. 2013. A draft *Musa balbisiana* genome sequence for molecular genetics in polyploid, inter- and intra-specific *Musa* hybrids. *BMC Genomics* 14: 683.

D'Hont, A. et al. 2012. The banana (*Musa acuminata*) genome and the evolution of monocotyledonous plants. *Nature* 488:213-217.

Dita, M. et al. 2018. Fusarium Wilt of banana: current knowledge on epidemiology and research needs toward sustainable disease management. *Front Plant Sci.* 9:1468.

Heslop-Harrison, J. S. and Schwarzacher, T. 2007. Domestication, Genomics and the Future for Banana. *Annals of Botany* 100(5):1073-1084.

Hiller, K, et al. 2004. PrediSi: prediction of signal peptides and their cleavage positions. *Nucleic Acids Res.* 32 (Web Server issue):W375-9.

Hippolyte, I. et al. 2012. Foundation characteristics of edible *Musa* triploids revealed from allelic distribution of SSR markers. *Annals of Botany* 109(5):937-951.

Hughes, A. L and Nei, M. 1988 *Nature* 335:167-170.

Ishihara et al. 2016. An improved method for RNA extraction from woody legume species *Acacia koa* A. Gray and *Leucaena leucocephala* (Lam.) de Wit. *Int. J. For. Wood Sci.* 3(1): 31-35.

Kreitman, M. and Akashi, H. 1995. Molecular evidence for natural selection. *Annu. Rev. Ecol. Syst.* 26:403-422.

Kumar, S., et al. 2018. MEGA X: Molecular Evolutionary Genetics Analysis across computing platforms. *Molecular Biology and Evolution* 35:1547-1549.

Li, C.-Y. et al. 2012. Transcriptome profiling of resistant and susceptible Cavendish banana roots following inoculation with *Fusarium oxysporum* f. sp. *cubense* tropical race 4. *BMC Genomics* 13:374.

Li, W.-H. et al. 1985. A new method for estimating synonymous and nonsynonymous rates of nucleotide substitution considering the relative likelihood of nucleotide and codon changes. *Mol. Biol. Evol.* 2: 150-174.

Li, W.-H. 1993. Unbiased estimation of the rates of synonymous and nonsynonymous substitution. *J. Mol. Evol.* 36: 9699.

Li, W.-H., 1997. *Molecular Evolution*. Sunderland, Massachusetts: Sinauer Associates.

Li, W. M. et al. 2015. Resistance sources to *Fusarium oxysporum* f sp. *cubense* tropical race 4 in banana wild relatives. *Plant Pathology* 64:1061-1067.

Ma, X, et al. 2015 A Robust CRISPR/Cas9 System for Convenient, High-Efficiency Multiplex Genome Editing in Monocot and Dicot Plants. *Mol. Plant.* 8:1274-1284.

Messier, W. and Stewart, C.-B. 1994 *Current Biol.* 4:911-913.

Messier, W. and Stewart, C-B. 1997. *Nature* 385:151-154.

Nei M. and Kumar S. 2000. *Molecular Evolution and Phylogenetics.* Oxford University Press, New York.

Paul, J.-Y. et al. 2011. Apoptosis-related genes confer resistance to Fusarium wilt in transgenic 'Lady Finger' bananas. *Plant Biotechnology Journal.*

Niu, Y. et al. 2018. Comparative digital gene expression analysis of tissue-cultured plantlets of highly resistant and susceptible banana cultivars in response to *Fusarium oxysporum. Int. J. Mol. Sci.* 19. doi: 10.3390/ijms19020350.

Peraza-Echeverria, S. et al. 2009. Molecular cloning and in silico analysis of potential *Fusarium* resistance genes in banana. *Mol. Breeding.* 23(3): 431-443.

Ploetz, R. C. 2015. Fusarium Wilt of banana. *Phytopathology Review.*

Raboin, L-M. et al. 2005. Diploid Ancestors of Triploid Export Banana Cultivars: Molecular Identification of 2n Restitution Gamete Donors and n Gamete Donors. *Mol Breeding* 16:333.

Reese M. G. 2001. Application of a time-delay neural network to promoter annotation in the *Drosophila melanogaster* genome. *Comput. Chem.* 26(1): 51-56.

Ribeiro, L. R. et al. 2018. Sources of resistance to *Fusarium oxysporum* f sp. *cubense* in banana germplasm. *Rev. Bras. Frutic.* 40:1. Epub Feb. 8, 2018.

Rouard, M. et al. 2018. Three New Genome Assemblies Support a Rapid Radiation in *Musa acuminata* (Wild Banana). *Genome Biology and Evolution* 10(12): 3129-3140.

Solovyev V. V. and Salamov A. A. 1997. The Gene-Finder computer tools for analysis of human and model organisms genome sequences. In *Proceedings of the Fifth International Conference on Intelligent Systems for Molecular Biology* (eds. Rawling C., Clark D., Altman R., Hunter L., Lengauer T., Wodak S.), Halkidiki, Greece, AAAI Press, 294-302.

Solovyev V. V. 2001. Statistical approaches in Eukaryotic gene prediction. In *Handbook of Statistical Genetics* (eds. Balding D. et al.), John Wiley & Sons, Ltd., p. 83-127.

Solovyev V. V. and Shahmuradov I. A. 2003. PromH: Promoters identification using orthologous genomic sequences. *Nucleic Acids Res.* 31(13): 3540-3545.

Stokstad, E. 2019. Banana fungus puts Latin America on alert. *Science* 365(6450): 207-208.

Ssali, R. et al. 2013. Inheritance of resistance to *Fusarium oxysporum* f sp. *cubense* race 1 in bananas. *Euphytica* 194: 425. Van der Berg, N. et al. 2007. Tolerance in banana to Fusarium wilt is associated with early up-regulation of cell wall-strengthening genes in the roots. *Molecular Plant Pathology.* 8(3): 333-341.

Venkataramana, R. K. et al. 2015. Insights into *Musa balbisiana* and *Musa acuminata* species divergence and development of genic microsatellites by transcriptomics approach. *Plant Gene* 4: 78-82.

Wang, Y. et al. 2017. Differential gene expression in banana roots in response to Fusarium wilt. *Canadian Journal of Plant Pathology* 39(2): 163-175. doi.org/10.1080/07060661.2017.1342693.

Wu, W. et al. 2016. Whole genome sequencing of a banana wild relative *Musa itinerans* provides insights into lineage-specific diversification of the *Musa* genus. *Scientific Reports* 6: Article number: 31586.

Zhang, L. et al. (2018) Identification and evaluation of resistance to *Fusarium oxysporum* f. sp. *cubense* tropical race 4 in *Musa acuminata* Pahang. *Euphytica* 214: 106.

Zuo, C. et al. 2018. Germplasm screening of *Musa* spp. for resistance to *Fusarium oxysporum* f. sp. *cubense* tropical race 4 (Foc-TR4). *Eur J Plant Pathol.* 151:723.

What is claimed is:

1. A nucleic acid construct comprising a nucleic acid sequence coding a peptide conferring resistance to *Fusarium oxysporum* race 4 when expressed in a banana plant, wherein said nucleic acid sequence is selected from the group consisting of a nucleic acid sequence having at least 97% sequence identity to SEQ ID NO: 9 and SEQ ID NO: 11 wherein nucleotide positions 148, 323, 344, and 347 of the nucleic acid sequence are G, A, C, and T, respectively, and wherein the nucleic acid sequence is operably linked to a promoter capable of driving expression of the nucleic acid sequence.

2. The nucleic acid construct of claim 1, wherein the promoter is a plant promoter.

3. A transgenic banana plant, plant part, plant cell, or plant tissue culture comprising a nucleic acid construct comprising a nucleic acid sequence coding a peptide conferring resistance to *Fusarium oxysporum* race 4 when expressed in a plant, wherein said nucleic acid sequence is selected from the group consisting of a nucleic acid sequence having at least 97% sequence identity to SEQ ID NO: 9 and SEQ ID NO: 11, wherein nucleotide positions 148, 323, 344, and 347 of the nucleic acid sequence are G, A, C, and T, respectively, and wherein the nucleic acid sequence is operably linked to a promoter capable of driving expression of the nucleic acid sequence.

4. A method of transforming a banana plant cell comprising introducing the nucleic acid construct of claim 1 into a plant cell, whereby the transformed plant cell expresses the nucleic acid sequence coding a peptide conferring resistance to *Fusarium oxysporum* race 4.

5. The method of claim 4, wherein the banana plant cell is a Cavendish plant cell.

6. The method of claim 4, wherein the plant cell is a *Musa acuminata* plant cell.

7. The method of claim 4, further comprising producing a transformed banana plant tissue from the transformed banana plant cell.

8. The method of claim 7, further comprising producing a transformed banana plantlet from the transformed banana plant tissue.

9. The method of claim 8, further comprising producing a banana clone of the transformed banana plantlet, wherein the clone expresses the nucleic acid sequence coding a peptide conferring resistance to *Fusarium oxysporum* race 4.

10. The method of claim 8, further comprising growing the transformed banana plantlet into a mature transformed banana plant, wherein the mature transformed plant expresses the nucleic acid sequence coding a peptide conferring resistance to *Fusarium oxysporum* race 4.

11. The method of claim 10, wherein the mature transformed banana plant is a *Musa acuminata* plant and the mature transformed *Musa acuminata* plant is capable of producing fruit.

12. The method of claim 11, further comprising producing clones of the mature transformed *Musa acuminata* plant.

13. The transgenic plant of claim 3, wherein the promoter is a plant promoter.

14. A method for producing and selecting a banana plant resistant to *Fusarium oxysporum* race 4, said method comprising:
   a) crossing the mature transformed banana plant of claim 10 with another different banana plant,
   b) harvesting the resultant banana seed,
   c) growing the seed from step b) to produce progeny banana plants, and
   d) screening the progeny banana plants from step c) for resistance to *Fusarium oxysporum* race 4, and e) selecting progeny banana plants resistant to *Fusarium oxysporum* race 4.

15. A nucleic acid construct comprising a nucleic acid sequence coding a peptide conferring resistance to *Fusarium oxysporum* race 4 when expressed in a banana plant, wherein the nucleic acid sequence is operably linked to a promoter capable of driving expression of the nucleic acid sequence, wherein amino acid positions 50, 108, 115, and 116 of the peptide are Valine, Glutamic Acid, Proline, and Valine, respectively, and wherein said peptide has an amino acid sequence having at least 97% sequence identity to SEQ ID NO: 12.

16. The nucleic acid construct of claim 15, wherein the plant is a *Musa acuminata* plant.

17. The nucleic acid construct of claim 1, wherein the nucleic acid sequence has at least 98% sequence identity to SEQ ID NO: 9, and SEQ ID NO: 11.

18. The nucleic acid construct of claim 1, wherein the nucleic acid sequence has at least 99% sequence identity to SEQ ID NO: 9, and SEQ ID NO: 11.

19. The transgenic banana plant, plant part, plant cell, or plant tissue culture of claim 3, wherein the nucleic acid sequence has at least 98% sequence identity to SEQ ID NO: 9, and SEQ ID NO: 11.

20. The transgenic banana plant, plant part, plant cell, or plant tissue culture of claim 3, wherein the nucleic acid sequence has at least 99% sequence identity to SEQ ID NO: 9, and SEQ ID NO: 11.

21. The nucleic acid construct of claim 15, wherein the amino acid sequence has at least 98% sequence identity to SEQ ID NO: 12.

22. The nucleic acid construct of claim 15, wherein the amino acid sequence has at least 99% sequence identity to SEQ ID NO: 12.

* * * * *

SEQUENCE LISTING

<160> NUMBER OF SEQ ID NOS: 32

<210> SEQ ID NO 1
<211> LENGTH: 553
<212> TYPE: DNA
<213> ORGANISM: Musa itinerans

<400> SEQUENCE: 1

```
gtaagcaatg gctggaggag gcaaaagagg tgaagcgtcg tctcttctac ttgtgacgct      60
gctcgtgatg ttgttggcct tcttcgccac cgactcctcg gcggcccgtg tcacaccccg     120
tccgcactcc ctcgccagag cggtactgag tgcgttggag gcaagggcag atgggccgtg     180
ttgcagatgc atctgtcctc tcatttaccc acctacttgg tgcgtttgca gcggcgtatg     240
gcaaggctcc tgcccttccg cctgcaccaa ctgcgagtgt ctcctcaacg agtgcacttg     300
cctcgatcac gtggactaca aggcctgcca ggccgactcc tgtggctggc ttgatggcgt     360
ccccaaacta gagccgtcgc agcagtgggc gatcgaagaa accggtggga aattagcgat     420
gatggtgtga tccaattgtg tttgtgatcg cctgtcgtct tctctcgctc cgtcccatcc     480
atctatccat ccatctactt ataatctatg tcgtgtaccg tcgtgcggcg ttgctttgct     540
tcggtaataa aat                                                       553
```

<210> SEQ ID NO 2
<211> LENGTH: 423

<212> TYPE: DNA
<213> ORGANISM: Musa itinerans

<400> SEQUENCE: 2

```
atggctggag gaggcaaaag aggtgaagcg tcgtctcttc tacttgtgac gctgctcgtg    60
atgttgttgg ccttcttcgc caccgactcc tcggcggccc gtgtcacacc cgtccgcac    120
tccctcgcca gagcggtact gagtgcgttg gaggcaaggg cagatgggcc gtgttgcaga    180
tgcatctgtc ctctcattta cccacctact tggtgcgttt gcagcggcgt atggcaaggc    240
tcctgccctt ccgcctgcac caactgcgag tgtctcctca cgagtgcac ttgcctcgat    300
cacgtggact acaaggcctg ccaggccgac tcctgtggct ggcttgatgg cgtccccaaa    360
ctagagccgt cgcagcagtg ggcgatcgaa gaaaccggtg gaaattagc gatgatggtg    420
tga                                                                 423
```

<210> SEQ ID NO 3
<211> LENGTH: 140
<212> TYPE: PRT
<213> ORGANISM: Musa itinerans

<400> SEQUENCE: 3

```
Met Ala Gly Gly Gly Lys Arg Gly Glu Ala Ser Ser Leu Leu Leu Val
1               5                   10                  15
Thr Leu Leu Val Met Leu Leu Ala Phe Phe Ala Thr Asp Ser Ser Ala
            20                  25                  30
Ala Arg Val Thr Pro Arg Pro His Ser Leu Ala Arg Ala Val Leu Ser
        35                  40                  45
Ala Leu Glu Ala Arg Ala Asp Gly Pro Cys Cys Arg Cys Ile Cys Pro
    50                  55                  60
Leu Ile Tyr Pro Pro Thr Trp Cys Val Cys Ser Gly Val Trp Gln Gly
65                  70                  75                  80
Ser Cys Pro Ser Ala Cys Thr Asn Cys Glu Cys Leu Leu Asn Glu Cys
                85                  90                  95
Thr Cys Leu Asp His Val Asp Tyr Lys Ala Cys Gln Ala Asp Ser Cys
            100                 105                 110
Gly Trp Leu Asp Gly Val Pro Lys Leu Glu Pro Ser Gln Gln Trp Ala
        115                 120                 125
Ile Glu Glu Thr Gly Gly Lys Leu Ala Met Met Val
    130                 135                 140
```

<210> SEQ ID NO 4
<211> LENGTH: 534
<212> TYPE: DNA
<213> ORGANISM: Musa itinerans

<400> SEQUENCE: 4

```
ggtaagcaat ggctggagga ggcaaaagag gtgaagcgtc gtctcttcta cttgtgacgc    60
tgctcgtgat gttgttggcc ttcttcgcca ccgactcctc ggcggccgt gtcacacccc    120
gtccgcactc cctcgccaga gcggtactga gtgcgttgga gggaagggcc gatgggccgt    180
gttgcagatg catctgtcct ctcatttacc cacctacttg gtgcatttgc agcggcgtat    240
ggcaaggctc ctgcccttcc gcctgcacca actgcgagtg tctcctcaac gagtgcactt    300
gcctcgatca cgtggactac aaggcctgcg aggccgactc ctgtggctgg cttgatggcg    360
tccccaaact agagccgtcg cagcagtggg cgatcgaaga aaccggtggg aaattagcgg    420
cgatggtgtg atccaaatgt gtttgtgttc gcctgtcgtc ttctctcgcg ccgtcctatc    480
```

```
catctatcca tccatctact tataatctat gtcgtgtacc gtcgtgtggt gttg        534
```

```
<210> SEQ ID NO 5
<211> LENGTH: 423
<212> TYPE: DNA
<213> ORGANISM: Musa itinerans

<400> SEQUENCE: 5
atggctggag gaggcaaaag aggtgaagcg tcgtctcttc tacttgtgac gctgctcgtg    60
atgttgttgg ccttcttcgc caccgactcc tcggcggccc gtgtcacacc ccgtccgcac   120
tccctcgcca gagcggtact gagtgcgttg gagggaaggg ccgatgggcc gtgttgcaga   180
tgcatctgtc ctctcattta cccacctact tggtgcattt gcagcggcgt atggcaaggc   240
tcctgccctt ccgcctgcac caactgcgag tgtctcctca cgagtgcact tgcctcgat    300 cacgtggact acaaggcctg cgaggccgac tcctgtggct ggcttgatgg cgtccccaaa   360
ctagagccgt cgcagcagtg ggcgatcgaa gaaaccggtg gaaattagc ggcgatggtg    420 tga                                                                423
```

```
<210> SEQ ID NO 6
<211> LENGTH: 140
<212> TYPE: PRT
<213> ORGANISM: Musa itinerans

<400> SEQUENCE: 6

Met Ala Gly Gly Gly Lys Arg Gly Glu Ala Ser Ser Leu Leu Leu Val
1               5                   10                  15

Thr Leu Leu Val Met Leu Leu Ala Phe Phe Ala Thr Asp Ser Ser Ala
            20                  25                  30

Ala Arg Val Thr Pro Arg Pro His Ser Leu Ala Arg Ala Val Leu Ser
        35                  40                  45

Ala Leu Glu Gly Arg Ala Asp Gly Pro Cys Cys Arg Cys Ile Cys Pro
    50                  55                  60

Leu Ile Tyr Pro Pro Thr Trp Cys Ile Cys Ser Gly Val Trp Gln Gly
65                  70                  75                  80

Ser Cys Pro Ser Ala Cys Thr Asn Cys Glu Cys Leu Leu Asn Glu Cys
                85                  90                  95

Thr Cys Leu Asp His Val Asp Tyr Lys Ala Cys Glu Ala Asp Ser Cys
            100                 105                 110

Gly Trp Leu Asp Gly Val Pro Lys Leu Glu Pro Ser Gln Gln Trp Ala
        115                 120                 125

Ile Glu Glu Thr Gly Gly Lys Leu Ala Ala Met Val
    130                 135                 140
```

```
<210> SEQ ID NO 7
<211> LENGTH: 398
<212> TYPE: DNA
<213> ORGANISM: Musa itinerans

<400> SEQUENCE: 7
acgttgtgat agaaagttca gcggtaagca atggctggag gaggcaaaag aggtgaagcg    60
tcgtctcttc tacttgtgac gctgctcgtg atgttgttgg ccttcttcgc caccgactcc   120
tcggcggccc gtgtcacacc ccgtccgcac tccctcgcca gagcggcgta tggcaaggct   180 cctgccttc cgcctgcacc aactgcgagt gtctcctcaa cgagtgcact tgcctcgatc    240
acgtggacta caaggcctgc caggccgact cctgtggctg gcttgatggc gtccccaaac   300
```

```
tagagccgtc gcagcagtgg gcgatcgaag aaaccggtgg gaaattagcg atgatggtgt    360
gatccaattg tgtttgtgat cgcctgtcgt cttctctc                           398

<210> SEQ ID NO 8
<211> LENGTH: 616
<212> TYPE: DNA
<213> ORGANISM: Musa acuminata

<400> SEQUENCE: 8
actccctcat acttgcacag gtacgttgtg atagaaagtt cagaggtaag cgatggctgg    60
aggaggcaaa agaggtgaag cgtcgtctct tctacttgtg acgctgctcg tgacgttgtt   120
ggctttcttc gccaccaact cctcggcagc ccgtgtcaca ccccgtccgc aatccctcgc   180
cagagcggca ctgagtgcgg tggggcaagg caagatgag ccgtgctgca gatgcgcgtg    240
tcctctcatt tacccaccta cttggtgcat ttgcggcggc atatggcaag gctcctgccc   300
ttccgcctgc aacaactgcc agtgtgtcct caacgagtgc acttgcctcg atcttatgga   360
ccccaaggtc tgcgaggcca actcctgtcc ctggcctgtt gcagccccca agtagagcc    420 ggcgcagcag tgggctatcg aagaaaccgg tgggaaatta gcgatgatgg tgtgatccaa   480
ttgtgtttgt gatcgcctgt cgtcttctct cgctccgtcc tatccatcta tccatccatc   540
tacttataat ctatgtcgtg taccgtcgtg tggtgttgct ttgcttcagt aataaaaata   600
aaatgcttct gctttt                                                   616

<210> SEQ ID NO 9
<211> LENGTH: 423
<212> TYPE: DNA
<213> ORGANISM: Musa acuminata

<400> SEQUENCE: 9
atggctggag gaggcaaaag aggtgaagcg tcgtctcttc tacttgtgac gctgctcgtg    60
acgttgttgg ctttcttcgc caccaactcc tcggcagccc gtgtcacacc ccgtccgcaa   120
tccctcgcca gagcggcact gagtgcggtg gggcaaggc aagatgagcc gtgctgcaga    180
tgcgcgtgtc ctctcattta cccacctact tggtgcattt gcggcggcat atggcaaggc   240
tcctgccctt ccgcctgcaa caactgccag tgtgtcctca acgagtgcac ttgcctcgat   300
cttatggacc ccaaggtctg cgaggccaac tcctgtccct ggcctgttgc agcccccaaa   360
gtagagccgg cgcagcagtg ggctatcgaa gaaaccggtg ggaaattagc gatgatggtg   420
tga                                                                 423

<210> SEQ ID NO 10
<211> LENGTH: 616
<212> TYPE: DNA
<213> ORGANISM: Musa acuminata

<400> SEQUENCE: 10
actccctcat acttgcacag gtacgttgtg atagaaagtt cagaggtaag cgatggctgg    60
aggaggcaaa agaggtgaag cgtcgtctct tctacttgtg acgctgctcg tgacgttgtt   120
ggctttcttc gccaccaact cctcggcagc ccgtgtcaca ccccgtccgc aatccctcgc   180
cagagcggca ctgagtgcgg tggggcaagg caagatgag ccgtgctgca gatgcgcgtg    240
tcctctcatt tacccaccta cttggtgcat ttgcggcggc atatggcaag gctcctgccc   300
ttccgcctgc aacaactgcc agtgtgtcct gaacgagtgc acttgcctcg atcttatgga   360
```

```
cccaaggtc tgcgaggcca actcctgtcc ctggcctgtt gcagccccca aagtagagcc    420
ggcgcagcag tgggctatcg aagaaaccgg tgggaaatta gcgatgatgg tgtgatccaa    480
ttgtgtttgt gatcgcctgt cgtcttctct cgctccgtcc tatccatcta ccatccatc    540 tacttataat ctatgtcgtg taccgtcgtg tggtgttgct ttgcttcagt aataaaaata    600
aaatgcttct gctttt                                                    616

<210> SEQ ID NO 11
<211> LENGTH: 423
<212> TYPE: DNA
<213> ORGANISM: Musa acuminata

<400> SEQUENCE: 11
atggctggag gaggcaaaag aggtgaagcg tcgtctcttc tacttgtgac gctgctcgtg     60
acgttgttgg ctttcttcgc caccaactcc tcggcagccc gtgtcacacc ccgtccgcaa    120
tccctcgcca gagcggcact gagtgcggtg ggggcaaggc aagatgagcc gtgctgcaga    180
tgcgcgtgtc ctctcattta cccacctact tggtgcattt gcggcggcat atggcaaggc    240
tcctgccctt ccgcctgcaa caactgccag tgtgtcctga acgagtgcac ttgcctcgat    300
cttatggacc ccaaggtctg cgaggccaac tcctgtccct ggcctgttgc agcccccaaa    360
gtagagccgg cgcagcagtg ggctatcgaa gaaaccggtg gaaattagc gatgatggtg    420 tga                                                                  423

<210> SEQ ID NO 12
<211> LENGTH: 140
<212> TYPE: PRT
<213> ORGANISM: Musa acuminata

<400> SEQUENCE: 12

Met Ala Gly Gly Gly Lys Arg Gly Glu Ala Ser Ser Leu Leu Leu Val
1               5                   10                  15

Thr Leu Leu Val Thr Leu Leu Ala Phe Phe Ala Thr Asn Ser Ser Ala
            20                  25                  30

Ala Arg Val Thr Pro Arg Pro Gln Ser Leu Ala Arg Ala Ala Leu Ser
        35                  40                  45

Ala Val Gly Ala Arg Gln Asp Glu Pro Cys Cys Arg Cys Ala Cys Pro
    50                  55                  60

Leu Ile Tyr Pro Pro Thr Trp Cys Ile Cys Gly Gly Ile Trp Gln Gly
65                  70                  75                  80

Ser Cys Pro Ser Ala Cys Asn Asn Cys Gln Cys Val Leu Asn Glu Cys
                85                  90                  95

Thr Cys Leu Asp Leu Met Asp Pro Lys Val Cys Glu Ala Asn Ser Cys
            100                 105                 110

Pro Trp Pro Val Ala Ala Pro Lys Val Glu Pro Ala Gln Gln Trp Ala
        115                 120                 125

Ile Glu Glu Thr Gly Gly Lys Leu Ala Met Met Val
    130                 135                 140

<210> SEQ ID NO 13
<211> LENGTH: 445
<212> TYPE: DNA
<213> ORGANISM: Musa acuminata

<400> SEQUENCE: 13
gtaagcgatg gctggaggag gcaaaagagg tgaagcgtcg tctcttctac ttgtgacgct     60
```

```
gctcgtgacg ttgttggctt tcttcgccac caactcctcg gcagcccgtg tcacacccg      120 tccgcaatcc ctcgccagag cggcactgag tgcgttgggg gcaaggcaag atgagccgtg    180
ctgcagatgc gcgtgtcctc tcatttaccc acctacttgg tgcatttgcg gcggcatatg    240
gcaaggctcc tgcccttccg cctgcaacaa ctgccagtgt gtcctcaacg agtgcacttg    300
cctcgatctt atggacccca aggtctgcgt ggccaactcc tgtccctggc gtgatgcagc    360
ccccaaagta gagccggcgc agcagtgggc gatcgaagaa accggtggga aattagcgat    420
gatggtgtga tccaattgtg tttgt                                           445

<210> SEQ ID NO 14
<211> LENGTH: 423
<212> TYPE: DNA
<213> ORGANISM: Musa acuminata

<400> SEQUENCE: 14
atggctggag gaggcaaaag aggtgaagcg tcgtctcttc tacttgtgac gctgctcgtg     60
acgttgttgg ctttcttcgc caccaactcc tcggcagccc gtgtcacacc ccgtccgcaa    120
tccctcgcca gagcggcact gagtgcgttg ggggcaaggc aagatgagcc gtgctgcaga    180
tgcgcgtgtc ctctcattta cccacctact tggtgcattt gcggcggcat atggcaaggc    240
tcctgccctt ccgcctgcaa caactgccag tgtgtcctca acgagtgcac ttgcctcgat    300
cttatggacc ccaaggtctg cgtggccaac tcctgtccct ggcgtgatgc agcccccaaa    360
gtagagccgg cgcagcagtg ggcgatcgaa gaaaccggtg ggaaattagc gatgatggtg    420
tga                                                                   423

<210> SEQ ID NO 15
<211> LENGTH: 140
<212> TYPE: PRT
<213> ORGANISM: Musa acuminata

<400> SEQUENCE: 15

Met Ala Gly Gly Gly Lys Arg Gly Glu Ala Ser Ser Leu Leu Leu Val
1               5                   10                  15

Thr Leu Leu Val Thr Leu Leu Ala Phe Phe Ala Thr Asn Ser Ser Ala
            20                  25                  30

Ala Arg Val Thr Pro Arg Pro Gln Ser Leu Ala Arg Ala Ala Leu Ser
        35                  40                  45

Ala Leu Gly Ala Arg Gln Asp Glu Pro Cys Cys Arg Cys Ala Cys Pro
    50                  55                  60

Leu Ile Tyr Pro Pro Thr Trp Cys Ile Cys Gly Ile Trp Gln Gly
65                  70                  75                  80

Ser Cys Pro Ser Ala Cys Asn Asn Cys Gln Cys Val Leu Asn Glu Cys
                85                  90                  95

Thr Cys Leu Asp Leu Met Asp Pro Lys Val Cys Val Ala Asn Ser Cys
            100                 105                 110

Pro Trp Arg Asp Ala Ala Pro Lys Val Glu Pro Ala Gln Gln Trp Ala
        115                 120                 125

Ile Glu Glu Thr Gly Gly Lys Leu Ala Met Met Val
    130                 135                 140

<210> SEQ ID NO 16
<211> LENGTH: 525
<212> TYPE: DNA
<213> ORGANISM: Musa acuminata
```

<400> SEQUENCE: 16

```
gtaagcgatg gctggaggag gcaaaagagg tgaagcgtcg tctcttctac ttgtgacgct    60
gctcgtgacg ttgttggctt tcttcgccac caactcctcg gcagcccgtg tcacacccccg  120
tccgcaatcc ctcgccagag gtaggttggt aaatatgcat gcgaacatct atgattgggc  180
tggagatcga ggcatcgtta attccttctt catgctgcag cggcactgag tgcgttgggg  240
gcaaggcaag atgagccgtg ctgcagatgc gcgtgtcctc tcatttaccc acctacttgg  300
tgcatttgcg gcggcatatg gcaaggctcc tgcccttccg cctgcaacaa ctgccagtgt  360
gtcctcaacg agtgcacttg cctcgatctt atggacccca aggtctgcgt ggccaactcc  420
tgtccctggc gtgatgcagc ccccaaagta gagccggcgc agcagtgggc gatcgaagaa  480
accggtggga aattagcgat gatggtgtga tccaattgtg tttgt                  525
```

<210> SEQ ID NO 17
<211> LENGTH: 514
<212> TYPE: DNA
<213> ORGANISM: Musa basjoo

<400> SEQUENCE: 17

```
aggtaagcga tggctggagg aggcaaaaga ggtgaagcgt cgtctcttct acttgtgacg    60
ctgctcgtga cgttgttggc tttcttcgcc accaactcct cagcagcccg tgtcacaccc  120
cgtccgcaat ccctcgccag agcggcactg agtgcggtgg gggcaaggca agatgagccg  180
tgctgcagat gcgcgtgtcc tctcatttac ccacctactt ggtgcatttg cggcggcata  240
tggcaaggct cctgcccttc cgcctgcaac aactgccagt gtgtcctcaa cgagtgcact  300
tgcctcgatc ttatggaccc caaggtctgc gaggccaact cctgtccctg gcctgttgca  360
gcccccaaag tagagccggc gcagcagtgg gctatcgaag aaaccggtgg gaaattagcg  420
atgatggtgt gatccaattg tgtttgtgat cgcctgtcgt cttctctcgc tccgtcctat  480
ccatctatcc atccatctac ttataatcta tgtc                              514
```

<210> SEQ ID NO 18
<211> LENGTH: 423
<212> TYPE: DNA
<213> ORGANISM: Musa basjoo

<400> SEQUENCE: 18

```
atggctggag gaggcaaaag aggtgaagcg tcgtctcttc tacttgtgac gctgctcgtg    60
acgttgttgg cttcttcgc caccaactcc tcagcagccc gtgtcacacc ccgtccgcaa  120
tccctcgcca gagcggcact gagtgcggtg ggggcaaggc aagatgagcc gtgctgcaga  180
tgcgcgtgtc ctctcattta cccacctact tggtgcattt gcggcggcat atggcaaggc  240
tcctgcccttt ccgcctgcaa caactgccag tgtgtcctca acgagtgcac ttgcctcgat  300
cttatggacc ccaaggtctg cgaggccaac tcctgtccct ggcctgttgc agcccccaaa  360
gtagagccgg cgcagcagtg ggctatcgaa gaaaccggtg ggaaattagc gatgatggtg  420
tga                                                                423
```

<210> SEQ ID NO 19
<211> LENGTH: 140
<212> TYPE: PRT
<213> ORGANISM: Musa basjoo

<400> SEQUENCE: 19

Met Ala Gly Gly Gly Lys Arg Gly Glu Ala Ser Ser Leu Leu Leu Val

```
1               5                   10                  15
Thr Leu Leu Val Thr Leu Leu Ala Phe Phe Ala Thr Asn Ser Ser Ala
           20                  25                  30
Ala Arg Val Thr Pro Arg Pro Gln Ser Leu Ala Arg Ala Ala Leu Ser
           35                  40                  45
Ala Val Gly Ala Arg Gln Asp Glu Pro Cys Cys Arg Cys Ala Cys Pro
           50                  55                  60
Leu Ile Tyr Pro Pro Thr Trp Cys Ile Cys Gly Gly Ile Trp Gln Gly
65                  70                  75                  80
Ser Cys Pro Ser Ala Cys Asn Asn Cys Gln Cys Val Leu Asn Glu Cys
                85                  90                  95
Thr Cys Leu Asp Leu Met Asp Pro Lys Val Cys Glu Ala Asn Ser Cys
               100                 105                 110
Pro Trp Pro Val Ala Ala Pro Lys Val Glu Pro Ala Gln Gln Trp Ala
           115                 120                 125
Ile Glu Glu Thr Gly Gly Lys Leu Ala Met Met Val
           130                 135                 140
```

<210> SEQ ID NO 20
<211> LENGTH: 370
<212> TYPE: DNA
<213> ORGANISM: Musa basjoo

<400> SEQUENCE: 20

```
gcactgagtg cggtggggc aagcaaagat gagccgtgct gcagatgcgc gtgtcctctc      60
atttacccac ctacttggtg catttgcagc ggcatatggc aaggctcctg cccttccgcc    120
tgcaacaact gccagtgtgt cctcaacgag tgcacttgcc tcgatcttat ggaccccaag    180
gtctgcgagg ccaactcctg tccctggcct gttgcagccc ccaaagtaga gccggcgcag    240
cagtgggcta tcgaagaaac cggtgggaaa ttagcgatga tggtgtgatc caattgtgtt    300
tgtgatcacc tgtcgtcttc tctcgctccg tcctatccat ctatccatcc atctacttat    360
aatctatgtc                                                            370
```

<210> SEQ ID NO 21
<211> LENGTH: 288
<212> TYPE: DNA
<213> ORGANISM: Musa basjoo

<400> SEQUENCE: 21

```
gcactgagtg cggtggggc aagcaaagat gagccgtgct gcagatgcgc gtgtcctctc      60
atttacccac ctacttggtg catttgcagc ggcatatggc aaggctcctg cccttccgcc    120
tgcaacaact gccagtgtgt cctcaacgag tgcacttgcc tcgatcttat ggaccccaag    180
gtctgcgagg ccaactcctg tccctggcct gttgcagccc ccaaagtaga gccggcgcag    240
cagtgggcta tcgaagaaac cggtgggaaa ttagcgatga tggtgtga                 288
```

<210> SEQ ID NO 22
<211> LENGTH: 95
<212> TYPE: PRT
<213> ORGANISM: Musa basjoo

<400> SEQUENCE: 22

```
Ala Leu Ser Ala Val Gly Ala Ser Lys Asp Glu Pro Cys Cys Arg Cys
1               5                   10                  15
Ala Cys Pro Leu Ile Tyr Pro Pro Thr Trp Cys Ile Cys Ser Gly Ile
           20                  25                  30
```

```
Trp Gln Gly Ser Cys Pro Ser Ala Cys Asn Asn Cys Gln Cys Val Leu
        35                  40                  45

Asn Glu Cys Thr Cys Leu Asp Leu Met Asp Pro Lys Val Cys Glu Ala
 50                  55                  60

Asn Ser Cys Pro Trp Pro Val Ala Ala Pro Lys Val Glu Pro Ala Gln
 65              70                  75                  80

Gln Trp Ala Ile Glu Glu Thr Gly Gly Lys Leu Ala Met Met Val
                85                  90                  95

<210> SEQ ID NO 23
<211> LENGTH: 438
<212> TYPE: DNA
<213> ORGANISM: Musella lasiocarpa

<400> SEQUENCE: 23
ggtaagcaat ggctggagga ggcaaaagag gtgaagcgtc gtctcttctg cttgtgacgc    60
tgctcgtgac gttgttggcc ttcttcgcca ccgactcctc ggcagccgt gtcacgcccc    120 gtccgcaatc cctcgccaga gtggcactga gcgcgttggg cgtaaggcaa gatgagccgt    180
gctgcagatg catctgtcct cgcatttacc caactgcttg gtgcatttgc agcggcgcat    240
ggcaaggctc ctgcccttcc gcctgcacca cctgcaagtg tgacctcaac gagtgcactt    300
gcgacgatat cgtggactac aatgcctgcc tggccgactc ctgtccctgg cttgatgcag    360 cagccccaa ggtagagccg tcgcagcagt gggcgatcga agaaaccggt gggaaattag    420
cgacgatggt gtgatccg                                                  438

<210> SEQ ID NO 24
<211> LENGTH: 426
<212> TYPE: DNA
<213> ORGANISM: Musella lasiocarpa

<400> SEQUENCE: 24
atggctggag gaggcaaaag aggtgaagcg tcgtctcttc tgcttgtgac gctgctcgtg    60
acgttgttgg ccttcttcgc caccgactcc tcggcagccc gtgtcacgcc ccgtccgcaa    120
tccctcgcca gagtggcact gagcgcgttg ggcgtaaggc aagatgagcc gtgctgcaga    180
tgcatctgtc ctcgcattta cccaactgct tggtgcattt gcagcggcgc atggcaaggc    240
tcctgccctt ccgcctgcac cacctgcaag tgtgacctca acgagtgcac ttgcgacgat    300
atcgtggact acaatgcctg cctggccgac tcctgtccct ggcttgatgc agcagccccc    360
aaggtagagc cgtcgcagca gtgggcgatc gaagaaaccg gtgggaaatt agcgacgatg    420
gtgtga                                                                426

<210> SEQ ID NO 25
<211> LENGTH: 141
<212> TYPE: PRT
<213> ORGANISM: Musella lasiocarpa

<400> SEQUENCE: 25

Met Ala Gly Gly Gly Lys Arg Gly Glu Ala Ser Ser Leu Leu Leu Val
 1               5                  10                  15

Thr Leu Leu Val Thr Leu Leu Ala Phe Phe Ala Thr Asp Ser Ser Ala
                20                  25                  30

Ala Arg Val Thr Pro Arg Pro Gln Ser Leu Ala Arg Val Ala Leu Ser
        35                  40                  45

Ala Leu Gly Val Arg Gln Asp Glu Pro Cys Cys Arg Cys Ile Cys Pro
```

```
            50                  55                  60
Arg Ile Tyr Pro Thr Ala Trp Cys Ile Cys Ser Gly Ala Trp Gln Gly
 65                  70                  75                  80

Ser Cys Pro Ser Ala Cys Thr Thr Cys Lys Cys Asp Leu Asn Glu Cys
                 85                  90                  95

Thr Cys Asp Asp Ile Val Asp Tyr Asn Ala Cys Leu Ala Asp Ser Cys
            100                 105                 110

Pro Trp Leu Asp Ala Ala Ala Pro Lys Val Glu Pro Ser Gln Gln Trp
        115                 120                 125

Ala Ile Glu Glu Thr Gly Gly Lys Leu Ala Thr Met Val
        130                 135                 140

<210> SEQ ID NO 26
<211> LENGTH: 521
<212> TYPE: DNA
<213> ORGANISM: Musa balbisiana

<400> SEQUENCE: 26
atggctggag gaggcaaaag gggtgaagcg tcgtctcttc tacttgtgac gctgctcgtg    60
acgttgttgg ccttcttcgc caccgactcc tcggcagccc gtgtcgcacc ccgtccgcac   120
tccctcgcca gaggtaggta gataaatatg catgcgaact tgtatatgat tgggctggag   180
atcgaggcat cgttaattcc gtcttcatgc tgcagcggca ctgagtgcgt tgggggtaag   240
gcaagatgcg ccgtgctgca catgcgtctg tcctctcatt tacccacctc cttttgctt   300 ttgcggcggc gtatggcaag gctcctgccc gtccgcctgc accaactgcg agtgtgtcct   360
caacgagtgc acttgcatcg atcgtgtgga ccccaaggcc tgcgaggccg actcctgtgc   420
cggctcgatg cagcccccaa gtagagccgc tcgcagcagt gggcgaccga agaaaccggt   480
gggaaattag ggacgatggt gtgatccaat tgtgtttgtg a                       521

<210> SEQ ID NO 27
<211> LENGTH: 363
<212> TYPE: DNA
<213> ORGANISM: Musa balbisiana

<400> SEQUENCE: 27
atggctggag gaggcaaaag gggtgaagcg tcgtctcttc tacttgtgac gctgctcgtg    60
acgttgttgg ccttcttcgc caccgactcc tcggcagccc gtgtcgcacc ccgtccgcac   120
tccctcgcca gagcggcact gagtgcgttg ggggtaaggc aagatgcgcc gtgctgcaca   180
tgcgtctgtc ctctcattta cccacctcct ttttgctttt gcggcggcgt atggcaaggc   240
tcctgcccgt ccgcctgcac caactgcgag tgtgtcctca acgagtgcac ttgcatcgat   300
cgtgtggacc ccaaggcctg cgaggccgac tcctgtgccg gctcgatgca gcccccaaag   360
tag                                                                 363

<210> SEQ ID NO 28
<211> LENGTH: 428
<212> TYPE: DNA
<213> ORGANISM: Musa balbisiana

<400> SEQUENCE: 28
atggctggag gaggcaaaag gggtgaagcg tcgtctcttc tacttgtgac gctgctcgtg    60
acgttgttgg ccttcttcgc caccgactcc tcggcagccc gtgtcgcacc ccgtccgcac   120
tccctcgcca gaggtaggta gataaatatg catgcgaact tgtatatgat tgggctggag   180
```

-continued

```
atcgaggcat cgttaatccc gtcttcatgc tgcagcggca ctgagtgcgt tgggggtaaa    240
gccccttccg cctgcaccaa ctgcgagtgt gtcctcaacg agtgcacttg catcgatcgt    300
gtggacccca aggcctgcga ggccgactcc tgtgccggct ggctcgatgc agcccccaaa    360
gtagagccgt cgcagcagtg ggcgaccgaa gaaaccggtg ggaaattagg gacgatggtg    420
tgatccaa                                                            428
```

<210> SEQ ID NO 29
<211> LENGTH: 523
<212> TYPE: DNA
<213> ORGANISM: Musa balbisiana

<400> SEQUENCE: 29

```
atggctggag gaggcaaaag gggtgaagcg tcgtctcttc tacttgtgac gctgctcgtg     60
acgttgttgg ccttcttcgc caccgactcc tcggcagccc gtgtcgcacc ccgtccgcac    120
tccctcgcca gaggtaggta gataaatatg catgcgaaca tgtatatatg attgggctgg    180
agatcgaggc atcgttaatc ccgtcttcat gctgcagcgg cactgagtgc gttgggggta    240
aggcaagatg cgccgtgctg cacatgcgtc tgtcctctca tttacccacc tccttttgc    300 ttttgcggcg gcgtatggca aggctcctgc ccgtccgcct gcaccaactg cgagtgtgtc    360
ctcaacgagt gcacttgcat cgatcgtgtg accccaagg cctgcgtggc cgactcctgt    420
gccggctcga tgcagcccc aaagtagagc cgtcgcagca gtgggcgacc gaagaaaccg    480
gtgggaaatt agggacgatg gtgtgatcca attgtgtttg tga                     523
```

<210> SEQ ID NO 30
<211> LENGTH: 523
<212> TYPE: DNA
<213> ORGANISM: Musa balbisiana

<400> SEQUENCE: 30

```
atggctggag gaggcaaaag gggtgaagcg tcgtctcttc tacttgtgac gctgctcgtg     60
acgttgttgg ccttcttcgc caccgactcc tcggcagccc gtgtcgcacc ccgtccgcac    120
tccctcgcca gaggtaggta gataaatatg catgcgaact tgtatatgat tgggctggag    180
atcgaggcat cgttaatccc gtcttcatgc tgcagcggca ctgagtgcgt tgggggtaag    240
gcaagatgcg ccgtgctgca catgcgtctg tcctctcatt tacccacctc cttttgctt    300 ttgcggcggc gtmtggcaag gctcctgccc gtccgcctgc accaactgcg agtgtgtcct    360
caacgagtgc acttgcatcg atcgtgtgga ccccaaggcc tgcgaggccg actcctgtgc    420
cggctggctc gatgcagccc ccaaagtaga gccgtcgcag cagtgggcga ccgaagaaac    480
cggtgggaaa ttagggacga tggtgtgatc caattgtgtt tgt                     523
```

<210> SEQ ID NO 31
<211> LENGTH: 753
<212> TYPE: DNA
<213> ORGANISM: Musa acuminata

<400> SEQUENCE: 31

```
gtagagacac ttgagttgaa ttctgaatcc attatttctt ctcatgaacg catacgtccc     60
accatacaca ccaaatctta atggctcaag catcgtggca ctataaatag gacaagagga    120
gggatgaggt aaaacgcact ccctcatact tgcacaggta cgttgtgata gaaagttcag    180
aggtaagcga tggctggagg aggcaaaaga ggtgaagcgc gtctcttct acttgtgacg    240 ctgctcgtga cgttgttggc tttcttcgcc accaactcct cggcagcccg tgtcacaccc    300
```

```
cgtccgcaat ccctcgccag agcggcactg agtgcggtgg gggcaaggca agatgagccg    360
tgctgcagat gcgcgtgtcc tctcatttac ccacctactt ggtgcatttg cggcggcata    420
tggcaaggct cctgcccttc cgcctgcaac aactgccagt gtgtcctcaa cgagtgcact    480
tgcctcgatc ttatggaccc caaggtctgc gaggccaact cctgtccctg gcctgttgca    540
gcccccaaag tagagccggc gcagcagtgg gctatcgaag aaaccggtgg gaaattagcg    600
atgatggtgt gatccaattg tgtttgtgat cgcctgtcgt cttctctcgc tccgtcctat    660
ccatctatcc atccatctac ttataatcta tgtcgtgtac cgtcgtgtgg tgttgctttg    720
cttcagtaat aaaaataaaa tgcttctgct ttt                                 753

<210> SEQ ID NO 32
<211> LENGTH: 120
<212> TYPE: PRT
<213> ORGANISM: Musa balbisiana

<400> SEQUENCE: 32

Met Ala Gly Gly Gly Lys Arg Gly Glu Ala Ser Ser Leu Leu Leu Val
1               5                   10                  15

Thr Leu Leu Val Thr Leu Leu Ala Phe Phe Ala Thr Asp Ser Ser Ala
            20                  25                  30

Ala Arg Val Ala Pro Arg Pro His Ser Leu Ala Arg Ala Ala Leu Ser
        35                  40                  45

Ala Leu Gly Val Arg Gln Asp Ala Pro Cys Cys Thr Cys Val Cys Pro
    50                  55                  60

Leu Ile Tyr Pro Pro Pro Phe Cys Phe Cys Gly Val Trp Gln Gly
65                  70                  75                  80

Ser Cys Pro Ser Ala Cys Thr Asn Cys Glu Cys Val Leu Asn Glu Cys
            85                  90                  95

Thr Cys Ile Asp Arg Val Asp Pro Lys Ala Cys Glu Ala Asp Ser Cys
            100                 105                 110

Ala Gly Ser Met Gln Pro Pro Lys
        115                 120
```